US007022677B1

(12) United States Patent
Ishiyama et al.

(10) Patent No.: US 7,022,677 B1
(45) Date of Patent: Apr. 4, 2006

(54) AMIDE DERIVATIVES AS GROWTH HORMONE SECRETAGOGUES

(75) Inventors: Nobuo Ishiyama, Kyoto (JP); Hirohide Ishige, Kyoto (JP); Mitsuo Mimura, Kyoto (JP); Tadashi Okuno, Kyoto (JP); Kiyoharu Ukai, Kyoto (JP); Takeshi Kiyofuji, Kyoto (JP); Shinji Tauchi, Shizuoka (JP); Kiyoshi Inoguchi, Kyoto (JP); Ping Huang, Mountain View, CA (US); Gilda H. Loew, deceased, late of Mountain View, CA (US); by Linda J. Maki, legal representative, Menlo Park, CA (US)

(73) Assignees: Kaken Pharmaceutical Co., Ltd., Tokyo (JP); Molecular Research Institute, Mountain View, CA (US)

( * ) Notice: Subject to any disclaimer, the term of this patent is extended or adjusted under 35 U.S.C. 154(b) by 0 days.

(21) Appl. No.: 09/913,722

(22) PCT Filed: Feb. 17, 2000

(86) PCT No.: PCT/US00/04001

§ 371 (c)(1),
(2), (4) Date: Mar. 12, 2002

(87) PCT Pub. No.: WO00/48623

PCT Pub. Date: Aug. 24, 2000

Related U.S. Application Data

(63) Continuation-in-part of application No. 09/251,734, filed on Feb. 18, 1999, now abandoned.

(51) Int. Cl.
*A61K 38/05* (2006.01)
(52) U.S. Cl. .................. 514/19; 548/517; 548/527; 548/533; 548/537
(58) Field of Classification Search .................. 514/19, 514/866; 546/91, 99, 153, 204, 205; 548/517, 548/527, 537, 533; 530/333, 338, 339, 344; 562/466
See application file for complete search history.

(56) References Cited

U.S. PATENT DOCUMENTS

| 4,093,713 | A | * | 6/1978 | Sestanj et al. | 514/19 |
|---|---|---|---|---|---|
| 4,250,192 | A | * | 2/1981 | Sallmann et al. | 514/533 |
| 4,560,506 | A | * | 12/1985 | Weller et al. | 544/349 |
| 4,626,545 | A | * | 12/1986 | Taub | 514/423 |
| 4,766,110 | A | * | 8/1988 | Ryan et al. | 514/19 |
| 4,927,809 | A | * | 5/1990 | Stuber | 514/20 |
| 5,439,930 | A | * | 8/1995 | Seredenin et al. | 514/423 |
| 5,525,623 | A | * | 6/1996 | Spear et al. | 514/423 |
| 5,869,671 | A | * | 2/1999 | Wang et al. | 546/147 |
| 5,948,887 | A | * | 9/1999 | Evans et al. | 530/333 |
| 5,952,465 | A | * | 9/1999 | Evans et al. | 530/333 |
| 5,965,698 | A | * | 10/1999 | Evans et al. | 530/326 |
| 6,084,066 | A | * | 7/2000 | Evans et al. | 530/333 |
| 6,100,047 | A | * | 8/2000 | Wilkison et al. | 435/7.2 |
| 6,100,069 | A | * | 8/2000 | Biswas et al. | 435/69.3 |
| 6,133,456 | A | * | 10/2000 | Holt et al. | 548/533 |
| 6,147,189 | A | * | 11/2000 | Evans et al. | 530/333 |
| 6,150,527 | A | * | 11/2000 | Holt et al. | 546/189 |
| 2002/0137686 | A1 | * | 9/2002 | Ternansky et al. | 514/19 |
| 2002/0161240 | A1 | * | 10/2002 | Holt et al. | 548/533 |

FOREIGN PATENT DOCUMENTS

WO    WO93/04081    3/1993

OTHER PUBLICATIONS

A Pollak, et al. J. Am. Chem. Soc. (1999) 121, 11593-11594.*
Sarantakis et al, "Solid Phase Synthesis of Sec-Amides and Removal from the Polymeric Support Under Mild Conditions", Tetrahedron Letters, vol. 38, No. 42, pp. 7325-7328, 1997; XP004111205.
Stuerzeberger et al, "Synthetische Inhibitoren der Serinproteasen", Pharmazie, Veb Verlag Volk Und Gesundheit. Berlin, DD, vol. 42, No. 2, 1987, pp. 114-116, XP002169714.
Santamaria et al, "Synthesis of Tryptophan-dehydrobutyrine Diketopiperazines and Analogues", Tetrahedron, vol. 55, No. 4, Jan. 22, 1999, pp. 1173-1186; XP004151339.
Walpole et al, "2-Nitrophenylcarbamoyl-(S)-Prolyl-(S)-3-(2-Nahthyl)Alanyl-N-Benzyl-N-Methylamide (SDZ NKT 343), A Potent Human NK1 Tachykinin Receptor Antagonist with Good Oral Analgesic Activity in Chronic Pain Models", Journal of Medicinal Chemistry, American Chemical Society, vol. 41, No. 17, Aug. 13, 1998, pp. 3159-3173, XP000972902.

(Continued)

*Primary Examiner*—Bruce R. Campell
*Assistant Examiner*—Andrew D. Kosar
(74) *Attorney, Agent, or Firm*—Nixon & Vanderhye P.C.

(57) ABSTRACT

Disclosed are the novel compounds as growth hormone secretagogues represented by structural Formula (I), wherein $R^1$ is, substituted or unsubstituted alkyl, substituted or unsubstituted cycloalkyl, substituted or unsubstituted alkoxy, substituted or unsubstituted aryl, or substituted or unsubstituted amino, X is —CO— or —$SO_2$—, Y is Formula (II), wherein n is an integer from 0–4, $R^4$ is hydrogen, substituted or unsubstituted alkyl, substituted or unsubstituted cycloalkyl, substituted or unsubstituted aryl, $R^5$ and $R^6$ are independently selected from hydrogen, substituted or unsubstituted alkyl, or $R^5$ and $R^6$ or $R^4$ and $R^5$ are taken together to form substituted or unsubstituted alkylene, $R^2$ is hydrogen, or substituted or unsubstituted alkyl, $R^3$ is substituted or unsubstituted alkyl, substituted or unsubstituted cycloalkyl, substituted or unsubstituted aryl, D is substituted or unsubstituted amino, substituted or unsubstituted alkoxy, or substituted or unsubstituted alkylthio, * represents an asymmetric center, and pharmaceutically acceptable salts and individual isomers thereof, which have growth hormone releasing activity in humans or animals.

9 Claims, No Drawings

OTHER PUBLICATIONS

Yang et al, "Tripeptide Growth Hormone Secretagogues", Bioorganic & Medicinal Chemistry Letters, vol. 8, No. 7, Apr. 7, 1998, pp. 759-764, XP004136961.

Nargund et al, "Peptidomimetic growth hormone secretagogues: synthesis and biological activities of analogs varied at the indole nucleus of the prototypical spiropiperidine L-162,752", Bioorganic & Medicinal Chemistry Letters, vol. 6, No. 14, Jul. 23, 1996, pp. 1731-1736, XP004134930.

* cited by examiner

AMIDE DERIVATIVES AS GROWTH HORMONE SECRETAGOGUES

CROSS-REFERENCE TO RELATED APPLICATIONS

This application is the National stage entry of PCT US 00/04001, filed Feb. 17, 2000, which is a CIP of U.S. application Ser. No. 09/251,734, filed Feb. 18, 1999, which is now abandoned.

FIELD OF THE INVENTION

The present invention relates to synthetic peptidomimetics having growth hormone releasing activity in humans or animals, and their use in humans for treating medical disorders resulting from a deficiency in growth hormone, or use in animals for increasing the rate and extent of growth, or for increasing the milk or wool production, or for treatment of ailments.

BACKGROUND OF THE INVENTION

Growth hormone, which is secreted from the pituitary, stimulates growth of all tissues of the body that are capable of growing. In addition, growth hormone is known to have following basic effects on the metabolic process of the body:
1) Increase rate of protein synthesis in the cells of the body,
2) Decrease rate of carbohydrate utilization in the cells of the body;
3) Increase mobilization of the fatty acids and use of the fatty acids for the energy.

Artificial manipulation of growth hormone levels has been demonstrated to have significant therapeutic utility. Human growth hormone supplementation has been shown to be an effective treatment for growth hormone deficiency and their related diseases states in humans, such as short statue (Robinson and Clark., Growth Hormone: Basic and Clinical Aspect, Isaksspn, Binder, Hall and Hokfelt eds., Amsterdam, p 109–127 (1987).

Apart from this application, studies have uncovered new and significant properties of growth hormone which lend further importance to the ability to control growth hormone levels. For example, recent clinical studies indicate that growth hormone supplementation may be useful in combating the maladies of aging in humans. Elevated growth hormone levels in animals also have been shown to result in increase lean mass muscle. One application of this latter observation could results in higher production of leaner meat products or larger and/or stronger animals. However, their clinical and/or animal application, as with recombinant growth hormone, has been limited due to their high cost and lack of oral efficiency (Low, L. C. K., Neuroendocrinology, 1991, 53 (Suppl), 37–40: Thomer, M. O., Acta Pediatr 1993, 388 (Suppl), 2–7).

The release of growth hormone from pituitary organs is under tight control of a second protein, which is also commonly known in the art as somatomedin, growth hormone releasing factor (GRF), growth hormone releasing hormone (GHRH), growth releasing hormone (GRH) and neurotransmitters either directly or indirectly. Growth hormone release can be stimulated by growth hormone releasing hormone and inhibited by somatostatin. In both cases the hormones are released from the hypothalamus but their action is mediated primarily via specific receptors located in the pituitary. As a result, the development of synthetic growth hormone releasing agents and the use of drugs acting through established neurotrasmitter systems in the brain to stimulate growth hormone releasing are being considered as alternative to highly expensive and lack of oral efficiency growth hormone replacement therapy for the restoration on normal serum growth hormone levels (Pharm. Rev., 46, 1–33 (1994)).

Even before the discovery of the endogenous releasing factor GHRH in 1982 (Guillemin, R. et al., Science, 1982, 218:585–587), Bowers and co-workers had reported a series of peptides derived from leu and Met enkephalins which specifically release growth hormone from pituitary (Bowers, C. Y. et al., Molecular Endocrinology. MacIntyne 1 (Ed.) Elsevier/North Holland Biomedical Press, Amsterdam 1977, 287–292). It was later discovered that these growth hormone releasing peptides (GHRPs) act directly on the pituitary through a different signal transduction pathway from that of GHRH. In combination with GHRH, GHRPs act synergistically at the pituitary to release growth hormone. A hypothalamic binding site for GHRPs, which may be partially responsible for their growth hormone releasing in vivo by releasing endogenous GHRH, has been identified (Codd, E. E. et al., Neuropharmacology, 1989, 28, 1139–1144; Howard, D. H. et al., Science, 1996, 273, 974–976). Momany and Bowers employed molecular modeling techniques to discover the growth hormone releasing hexapeptide GHRP-6, which is extremely potent and specific growth hormone secretagogue in human. More potent analogs of GHRP-6 have been discovered and under clinical evaluation (Laron, A. Drugs, 1995, 50, 595–601). While GHRP-6 is a much more smaller peptide than either recombinant growth hormone or growth hormone releasing hormone, it still has low oral bioavailability in human (0.3%). However, GHRP-6 has demonstrated that relatively small molecule, with its possible advantage of lower cost and oral bioavailability, may be a viable alternative to subcutaneous treatment with recombinant growth hormone (DeVita, R. J. et al., Drugs of the Future, 1996, 21 (3), 273–281).

| | |
|---|---|
| His-D-Trp—Ala—Trp-D-Phe—Lys—NH$_2$ | GHRP-6 |
| Ala—His-D-β-Nal—Ala—Trp-D-Phe—Lys—NH$_2$ | GHRP-1 |
| D-Ala-D-β-Nal—Ala—Trp-D-Phe—Lys—NH$_2$ | GHRP-2 (KP-102) |
| His-D-2-MeTrp—Ala—Trp-D-Phe—Lys—NH$_2$ | Hexarelin |

In recent years significant efforts have been taken to develop non-peptidyl analogs of this series of compounds. Such compounds, termed growth hormone secretagogues, should be orally bioavailable, induce production or release of growth hormone, and act synergistically with growth hormone releasing hormone.

Representative growth hormone secretagogues are disclosed in U.S. Pat. No. 3,239,345; U.S. Pat. No. 4,036,979; U.S. Pat. No. 4,411,890; U.S. Pat. No. 4,851,408; U.S. Pat. No. 4,880,777; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,536,716; U.S. Pat. No. 5,545,735; U.S. Pat. No. 5,559,128; U.S. Pat. No. 5,576,301; U.S. Pat. No. 5,583,130; U.S. Pat. No. 5,492,916; U.S. Pat. No. 5,492,920; U.S. Pat. No. 5,494,919; U.S. Pat. No. 5,578,593; U.S. Pat. No. 5,622,973; U.S. Pat. No. 5,652,235; U.S. Pat. No. 5,663,171; U.S. Pat. No. 5,672,596; U.S. Pat. No. 5,721,250; U.S. Pat. No. 5,723,616; U.S. Pat. No. 5,726,307; U.S. Pat. No. 5,726,319; U.S. Pat. No. 5,731,317; U.S. Pat. No. 5,767,085; U.S. Pat.

No. 5,767,118; U.S. Pat. No. 5,767,124; U.S. Pat. No. 5,773,441; U.S. Pat. No. 5,777,112; U.S. Pat. No. 5,783,582; U.S. Pat. No. 5,798,337; U.S. Pat. No. 5,804,578; EP 144, 230; EP 513, 974; WO 9407486; WO 9408583; WO 9411012; WO 9413696; WO 9503290; WO 9509633; WO 9512598; WO 9513069; WO 9514666; WO 9516692; WO 9516675; WO 9517422; WO 9517423; WO 9534311; WO 9602530; WO 9605195; WO 9613265; WO 9615148; WO 9622997; WO 9624580; WO 9624587; WO 9635713; WO 9638471; WO 9700894; WO 9706803; WO 9706809; WO 9707117; WO 9711697; WO 9715191; WO 9722620; WO 9723508; WO 9724369; WO 9734604; WO 9736873; WO 9736878; WO 9740023; WO 9740071; WO 9741878; WO9741879; WO 9803473; WO 9810653; WO 9816527; WO 9818815; WO 9825622; WO 9825897; WO 9846569; WO 9851687; WO 9858947; WO 9858948; WO 9858950; WO 9909991; and Science, 260, 1640–1643 (1993), the entire of all of which are herein incorporated by reference.

U.S. Pat. No. 5,206,235 issued Apr. 27, 1993, describes a series of benzolactam compounds typified by the following structure (L-692, 429). These compounds have demonstrated clinical activity in humans in raising the growth hormone secretory levels (B. J. Gertz., Journal of Clinical Endocrinology and Metabolism, 77, 1393–1397 (1993)).

Second generation of growth hormone secretagogues is described in WO 94/13696 (MK0677), WO 96/15148 (G-7220). These compounds are typified by the following structure.

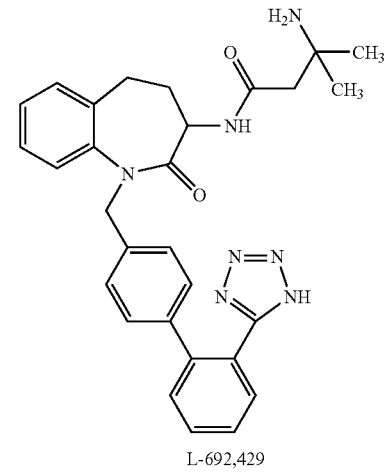

L-692,429

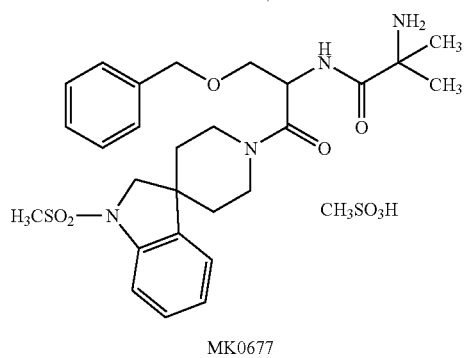

MK0677

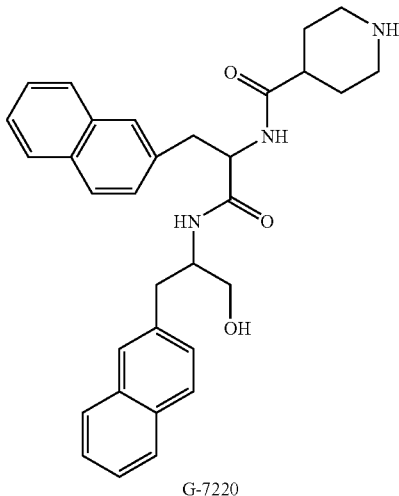

G-7220

A number of these compounds are reported to be more effective in promoting endogenous growth hormone release in humans, however, there remain problem with oral availability, specificity and safety.

Patents cited in the following disclose structurally similar compounds in this invention, but do not describe promotion of growth hormone release: WO9204371, WO9222569, WO9420126, WO9500536, WO9530687, WO9507291, WO9618643, WO9831704, WO9912572, EP443132, EP684257.

SUMMARY OF THE INVENTION

It is an object of this invention to provide novel growth hormone secretagogues that promote the release of endogenous growth hormone in mammals. It is a further object to provide secretagogues allowing synergistic increase in growth hormone secretion when combined with growth hormone releasing hormone. It is still a further object of this invention to provide more potent growth hormone secretagogues than those of the prior, especially "GHRP-6", "GHRP-1", "GHRP-2 (KP-102)", "L-692, 429", "L-692, 585", "MK-0677" and "G-7220. It is a further object to provide growth hormone secretagogues that are specific for growth hormone release and do not cause significant release of other hormones, especially; LH, FSH, TSH, ACTH, prolactin, vasopressin, oxytocin, insulin, and cortisol. These and other objects of the invention will be apparent from the following specification.

The Strategy of Lead Finding and Lead Optimization

It is the object of this invention to provide a novel class of non-peptidyl growth hormone secretagogues using an approach of computer-aided rational drug design and discovery. The computational strategy described below has produced 3D pharmacophores for 3D database search in the lead finding, and provided site-dependent quantitative structure activity relationship (QSAR) for fragment property refinement in the lead optimization, leading to the development of novel potent growth hormone secretagogues. The computational strategy has been implemented through three stages in the invention:

(a) conceptual stage—generation and validation of 3D-pharmacophores (b) discovery stage—database search and compound modification (c) optimization stage—development of QSAR for refinement (1) Conceptual Stage—Pharmacophore Development The structural components of the growth hormone releasing peptides (GHRPs) and non-peptidyl derivatives are important for their growth hormone releasing potency. It is thus the crucial step in rational design to develop 3D pharmacophores, which represent the three dimensional arrangement of functional groups essential for activity, from a number of compounds with known activities, similar mechanism of action, and similar in vivo properties. The seven potent peptides selected for pharmacophore generation in the present invention include "GHRP-6", "[D-Lys$^6$] GHRP-6", "KP-102(GHRP-2)", and its four peptidyl analogs. Non-peptidyl analogs chosen for pharmacophore development include "L-692,429", "L-692,585", "MK-0677", and "L-164,080". In addition, one inactive peptide "[Val$^3$]GHRP-6", and one inactive non-peptide "L-692,428" were used as control.

Conformations of each of these compounds were generated using a strategy of repeated cycles of high (900°K) and low (300°K) temperature molecule dynamics combined with energy minimization of molecule structures. Details of this strategy are described by Chew, C. et al. (Mol. Pharm., 1991, 39, 502). The calculations were performed using Quanta/CHARMm 4.0 (Molecular Simulation, Inc. USA). The search for the form in which flexible molecules such as peptides bind to Receptors is a challenging task because many low-energy conformations are accessible and they coexist in equilibrium. The complexity increases enormously when several diverse families of fairly flexible molecules are included and the goal is to identify the common geometry arrangements of moieties that are determinants of receptor recognition or activation because all low-energy conformations of each molecule should be included in analysis. A novel computer program, DistComp, was thus developed to perform systematic and automated comparisons of molecular conformations in different compounds for the determination of 3D pharmacophores (Huang, P. et al., J. Computer-Aided Molecular Design., 1997, 11, 21–28). DistComp provides a procedure for identifying common spatial arrangements of selected moieties in a given set of molecules. No prior assumption of an active conformation is necessary. There is also need for a rigid template. However, central to this procedure is the selection of sets of common functional moieties assumed to be important for recognition or activation. The validity of these candidate recognition or activation sites was then assessed by the program: for each hypothetical set of recognition or activation moieties selected, the program systematically determines whether any common 3D relationships among them exists in active analogs but are absent in inactive ones. Each set of proposal chemical moieties that satisfies this requirement, together with the common spatial arrangements identified, comprises candidate 3D pharmacophores.

Using the program DistComp, a convergent model termed "Pharmacophore I" which is common to all seven peptides and two non-peptides ("L-692,429", "L-692,585") was successfully developed. "Pharmacophore I" was subsequently validated using two new potent growth hormone secretagogues, "G-7220", "G-7134", developed at Genentech by that time with the results indicating that the two compounds fit well to the pharmacophore. Another convergent model, termed "Pharmacophore II", was developed when "MK-0677" and "L-164,080" were reported by Merck to be potent growth hormone scretagogues. "Pharmacophore II" is common to all seven peptides and two non-peptides, "MK-0677" and "L-164,080". Pharmacophore 1 and II have some common features, but differ in two components.

(2) Discovery Stage-Database Search and Compound Modification

The successful development of the 3D pharmacophores provides a logical framework for the design and discovery of novel growth hormone secretagogues in the present invention. Using these 3D pharmacophores, 3D database search was performed on a number of databases including MDDR, Chapman & Hall Database of Organic Compounds, Maybridge, CAS30K, and NCI Database. Both 3D rigid and flexible search methods were used. While the rigid search does static comparison of the 3D structure stored in database of a compound with the pharmacophore, the flexible search takes into account molecular flexibility. Compounds obtained from database search were then screened and modified using structural and chemical information, with emphasis on scaffold novelty, conformational rigidity, minimum extra components, and chemical aspects such as excluding compounds that are polymeric, clathrate, molecular complex, metal complex, toxic, or peptides.

Modification of compounds was performed mainly on compounds that have novel scaffolds. Subsequent computer modeling studies were then performed on compounds from the database search which had been either modified or obtained from a flexible search, in order to determine the extent to which they conformed either Pharmacophore I or II. Candidates which were found to be consistent with the pharmacophores and easy to synthesize were then selected for synthesis and pharmacological testing. Using these strategies, initial lead compounds in the present invention have been successfully designed and discovered.

(3) Optimization Stage—Development of QSAR for Refinement

The goal in this stage was to enhance the activity of initial lead compounds from, typically, micromolar into the nanomolar range. While experimentalists focused on making various analogs of the leads for SAR studies, computational efforts focused on the development of site-dependent QSAR (Quantitative Structure Activity Relationship) procedure embodied in a working program, for refinement of the lead compounds. The innovative approach is in addition to improving compounds by making them more consistent with the pharmacophores in terms of the three-dimensional arrangement/location of the functional groups.

Preliminary investigations were performed to demonstrate no significant correlation between the overall molecular properties of growth hormone releasing peptides and their activity. Clearly, growth hormone secretion activity cannot be described simply by these molecular descriptors. A possible explanation for this is that the overall molecular descriptors can be significantly modulated by the molecular regions which are not important to the drug-receptor interaction. As we have already experienced in many cases, complex drug interactions cannot be simply described by overall descriptors of a molecule.

A novel site-depended QSAR method was, therefore, developed to specifically identify the function of each pharmacophoric site that comprise the 3D pharmacophores. These supplementary requirements of site-dependent properties were used as additional criteria for optimizing and refining novel compounds on the basis of 3D pharmacophore. The most challenging aspect of this task was to identify and calculate relevant properties of each pharmacophoric site (i.e. site-dependent properties) rather than the properties of the entire molecule. These properties can be used in a regression analysis to identify the ones that modulate activity. Among the library of properties that can be calculated for each site are:

1) regional net atomic charges;
2) polarizability;
3) free energy of solvation;
4) Van der Waals volume;
5) hydrophobicity;
6) proton donating ability;
7) proton accepting ability;
8) molecular flexibility.

A prerequisite to use of this site-dependent QSAR procedure is the definition of the pharmacophoric sites or fragments that comprise an already identified 3D pharmacophore. A pharmacophoric site in a molecule is defined as a fragment consisting of a phamacophore atom (core), which is a component in 3D Phamacophore, together with its immediate neighbors in the molecule and capping atoms. The site-dependent QSAR studies have been performed on eight peptides including "GHRP-6", "[D-Lys$^6$] GHRP-6", "G-7134", "KP-102" and its four peptidyl analogs. The results demonstrated clearly the correlation of some fragment properties, particularly hydrophobicity, in these molecules with their growth hormone secretion activity. These results provided a useful guide for modification of the specific pharmacophoric sites leading to enhanced activity.

(4) Summary

The computational strategies were used here: extensive conformational studies and Distcomp analysis for a small number of known peptide and non-peptide analogs have led to the successful development of 3D pharmacophores for activation of growth hormone secretagogues agonists. These 3D activation pharmacophores have provided the essential, enabling basis for the design and discovery of the novel non-peptidyl growth hormone secretagogues in this invention. Database search using the 3D pharmacophores together with strategies for compound screening and modification have led to the discovery of initial lead compounds. A site-dependent QSAR developed for fragment property refinement has provided guidelines for lead optimization. These three steps-pharmacophore development, lead discovery and optimization together have led to the development of the novel potent growth hormone secretagogues described in this invention.

DETAILED DESCRIPTION OF THE INVENTION

Present invention provides the novel compounds presented by the structural Formula I;

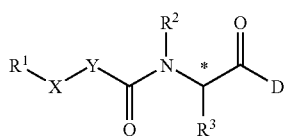

I wherein R$^1$ is, substituted or unsubstituted alkyl, substituted or unsubstituted cycloalkyl, substituted or unsubstituted alkoxy, substituted or unsubstituted aryl, or substituted or unsubstituted amino, X is —CO— or —SO$_2$—

Y is:

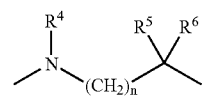

wherein n is an integer from 0–4,

R$^4$ is hydrogen, substituted or unsubstituted alkyl, substituted or unsubstituted cycloalkyl, substituted or unsubstituted aryl, R$^5$ and R$^6$ are independently selected from hydrogen, substituted or unsubstituted alkyl, or R$^5$ and R$^6$ or R$^4$ and R$^5$ are taken together to form substituted or unsubstituted C$_{2-7}$ alkylene, R$^2$ is hydrogen, or substituted or unsubstituted alkyl, R$^3$ is substituted or unsubstituted alkyl, substituted or unsubstituted cycloalkyl, substituted or unsubstituted aryl, D is substituted or unsubstituted amino, substituted or unsubstituted alkoxy, or substituted or unsubstituted alkylthio,

*represents an asymmetric center, and pharmaceutically acceptable salts thereof.

In Formula 1, R$^1$ is preferably C$_{1-11}$ alkyl which may be substituted by substituted or unsubstituted cycloalkyl, substituted or unsubstituted alkoxy, substituted or unsubstituted aryl, and/or hydroxy; C$_{3-6}$ cycloalkyl which may be substituted by substituted or unsubstituted alkyl, substituted or unsubstituted alkoxy, substituted or unsubstituted aryl, and/ or hydroxy; C$_{1-11}$ alkoxy which may be substituted by substituted or unsubstituted cycloalkyl, substituted or unsubstituted aryl and/or hydroxy; aryl which may be substituted by substituted or unsubstituted alkyl, substituted or unsubstituted alkoxy and/or hydroxy; or, amino which may be substituted by substituted or unsubstituted alkyl, and/or substituted or unsubstituted aryl.

In Formula I, R$^1$ is more preferably C$_{1-11}$ alkyl which may be substituted by cycloalkyl, alkoxy, arylalkoxy, aryl and/or halogenated aryl; C$_{3-6}$ cycloalkyl which may be substituted by alkyl; C$_{1-5}$ alkoxy which may be substituted by aryl; aryl which may be substituted by alkyl, alkoxy or/and halogen; or, di(C$_{1-6}$ alkyl)amino.

Examples of preferred R$_1$ include;

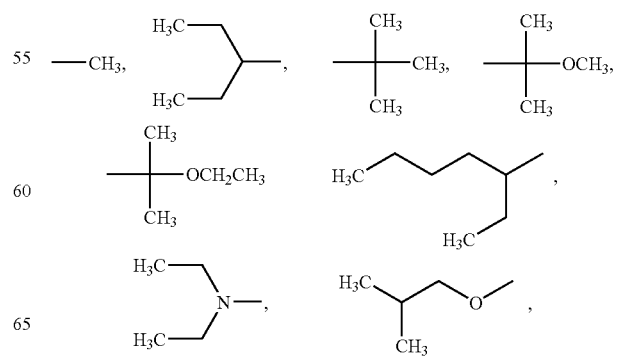

-continued

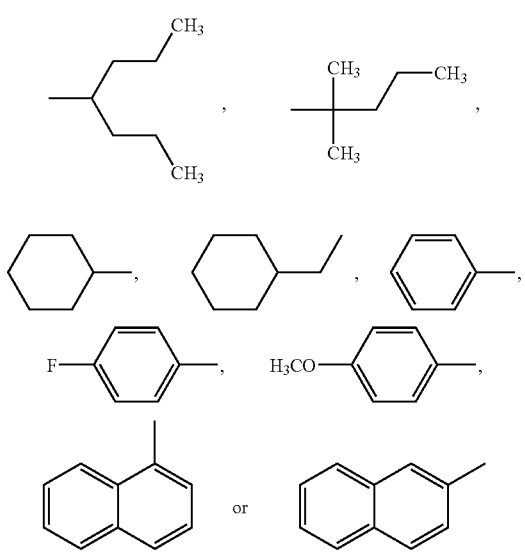

In Formula Y, R⁴ is preferably hydrogen, $C_{1-6}$ alkyl which may be substituted by aryl, $C_{1-6}$ cycloalkyl, or aryl.

Examples of preferred Y include;

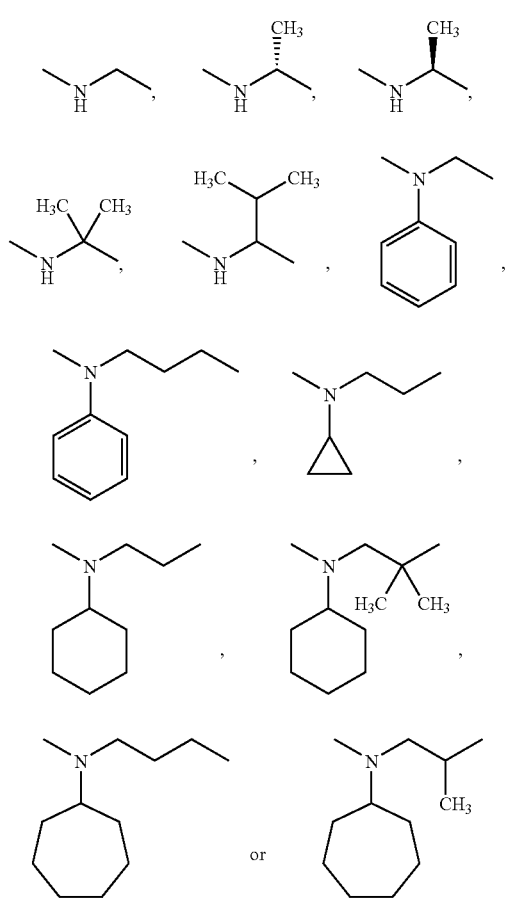

In Formula I, R⁴ and R⁵ are preferably taken together to form —(CH₂)$_m$—, wherein m is an integer from 0–4.

In Formula I, m+n are preferably 3 or 4.

Examples of preferred Y include;

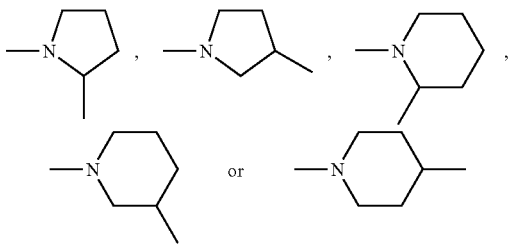

In Formula I, R⁵ and R⁶ are preferably taken together to form alkylene.

Examples of preferred Y include;

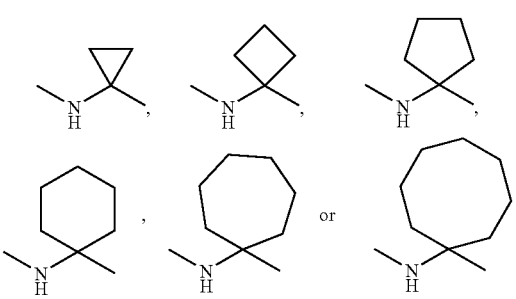

In Formula I, R² is preferably hydrogen,

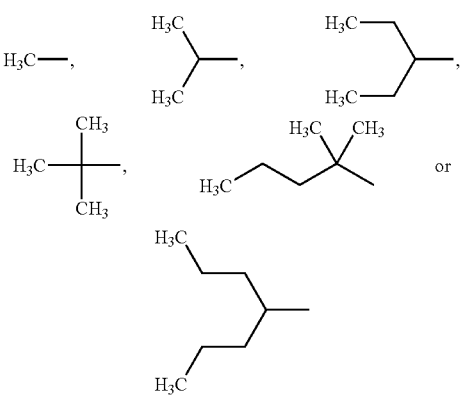

In Formula I, R³ is preferably $C_{1-10}$alkyl, alkoxy$C_{1-5}$alkyl, $C_{3-7}$cycloalkyl, aryl $C_{1-5}$alkyl, heterocycloaryl $C_{1-5}$alkyl, aryl, or heterocycloaryl which may be substituted by halogen, hydroxy, $C_{1-5}$ alkyl, $C_{1-5}$ alkoxy, nitro, cyano, amino, and/or subustituted amino, wherein aryl is monocyclic or bicyclic.

In Formula I, examples of more preferred R³ include;

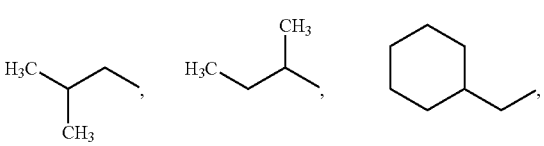

-continued

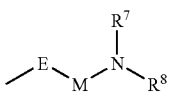

In Formula I, D is preferably

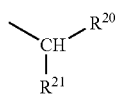

wherein E is —O—, —S—, or —N(R$^9$)— in which R$^9$ is hydrogen, substituted or unsubstituted alkyl, or substituted or unsubstituted cycloalkyl, R$^7$ is hydrogen, or C$_{1-5}$ alkyl, R$^8$ is hydrogen, substituted or unsubstituted C$_{1-8}$ acyl, amidino, C$_{1-6}$ alkoxycarbonyl, or in which R$^{20}$ is hydrogen, or C$_{1-5}$ alkyl, R$^{21}$ is hydrogen, C$_{1-8}$ alkyl, C$_{3-8}$ cycloalkyl, C$_{3-8}$ heterocycloalkyl, aryl, heteroaryl, C$_{1-6}$ hydroxylalkyl, C$_{1-6}$ alkoxylalkyl, aryloxy, or arylalkyloxy which may be substituted by halogen, hydroxy, C$_{1-6}$ alkyl, alkoxy, nitro, amino, substituted amino, cyano, carbonyl, C$_{1-6}$ alkylcarbonyl, or R$^7$ and R$^9$ are taken together to form alkylene, or R$^7$ and R$^8$ are taken together to form alkylene or hetero aromatic ring, M is;

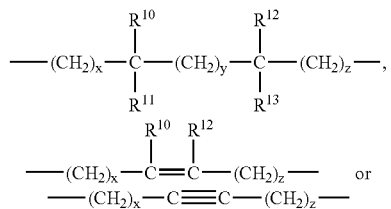

wherein x, y, and z are independently an integral number from 0 to 4,

R$^{10}$, R$^{11}$, R$^{12}$ and R$^{13}$ are independently hydrogen, halogen, [substituted or unsubstituted alkyl], —OR$^{14}$, —SR$^{14}$, —NR$^{14}$R$^{15}$, —NHC(O)R$^{14}$, —C(O)OR$^{14}$, —OC(O)R$^{14}$, —OC(O)OR$^{14}$, or —C(O)NR$^{14}$R$^{15}$, or taken together with R$^7$ or R$^8$ to form alkylene or hetero aromatic ring, R$^{14}$ and R$^{15}$ are independently hydrogen, or [substituted or unsubstituted alkyl], or R$^{14}$ is taken together with R$^7$ or R$^9$ to form alkylene, R$^{10}$ and R$^{12}$, or R$^{11}$ and R$^{13}$ are taken together to form alkylene, or hetero aromatic ring, R$^{10}$ and R$^{11}$, or R$^{12}$ and R$^{13}$ are taken together with carbon atom on each substituent to form carbonyl, thiocarbonyl, or imine.

In Formula I, examples of more preferred R$^{21}$ include;

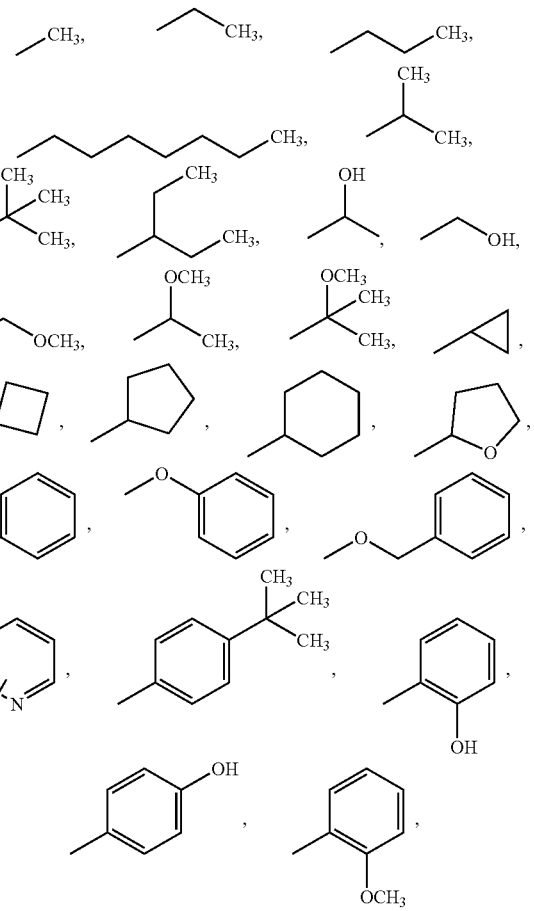

-continued

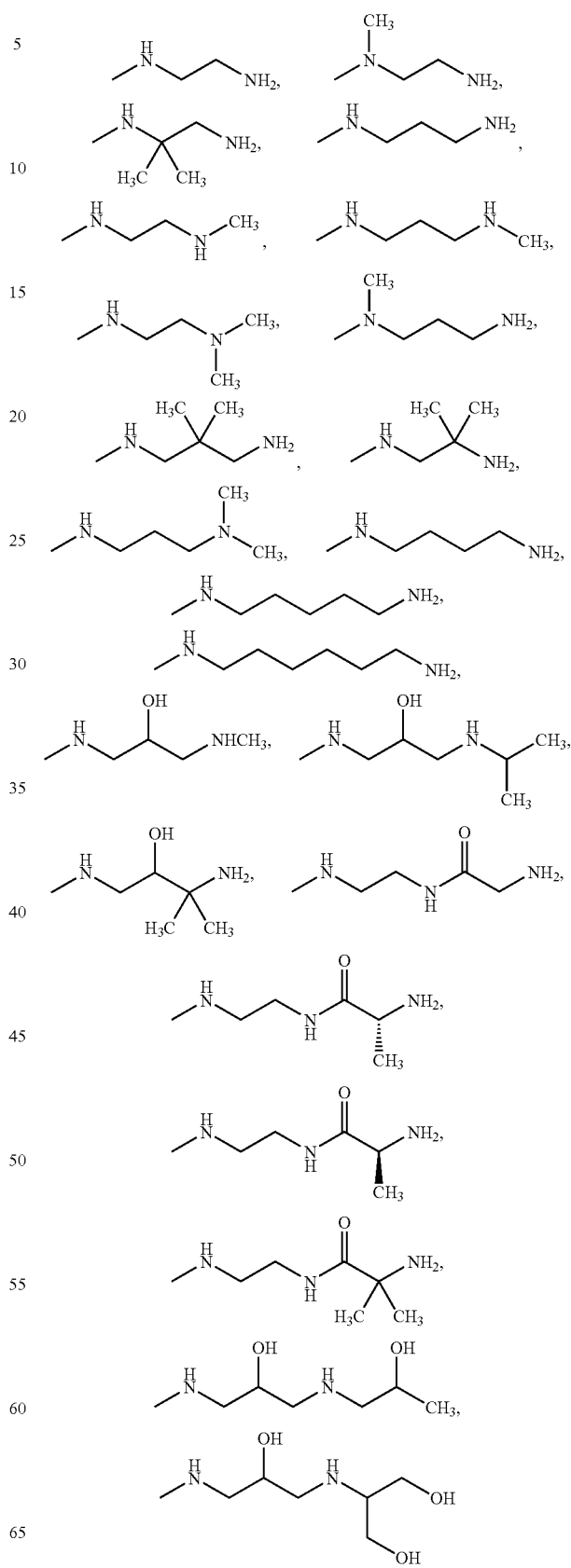

Examples of preferred D include;

In Formula D, $R^9$ is hydrogen, $C_{1-5}$ alkyl, or [$C_{3-8}$ cycloalkyl which may be substituted hydroxy or amino], $R^7$ and $R^8$ are independently hydrogen, [substituted or unsubstituted $C_{1-5}$ alkyl], $C_{1-8}$ acyl, or $C_{1-6}$ alkoxycarbonyl, $R^7$ and $R^8$, or $R^7$ and $R^9$ are taken together to form alkylene, $R^{10}$, $R^{11}$, $R^{12}$ and $R^{13}$ are independently hydrogen, halogen, substituted or unsubstituted $C_{1-5}$ alkyl, —$OR^{14}$, —$SR^{14}$, —$NR^{14}R^{15}$, —$NHC(O)R^{14}$, —$C(O)OR^{14}$, or —$OC(O)OR^{14}$, $R^{10}$ is taken together with $R^7$ or $R^9$ to form alkylene, $R^{14}$ and $R^{15}$ are independently hydrogen or $C_{1-5}$ alkyl, $R^{14}$ is taken together with $R^7$ or $R^9$ to form alkylene.

In Formula D, $R^8$ is preferably

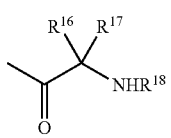

wherein $R^{16}$ and $R^{17}$ are independently hydrogen, or $C_{1-6}$ alkyl, $R^{18}$ is hydrogen, or [substituted or unsubstituted $C_{1-6}$ alkyl], or [substituted or unsubstituted aminoalkylcarbonyl].

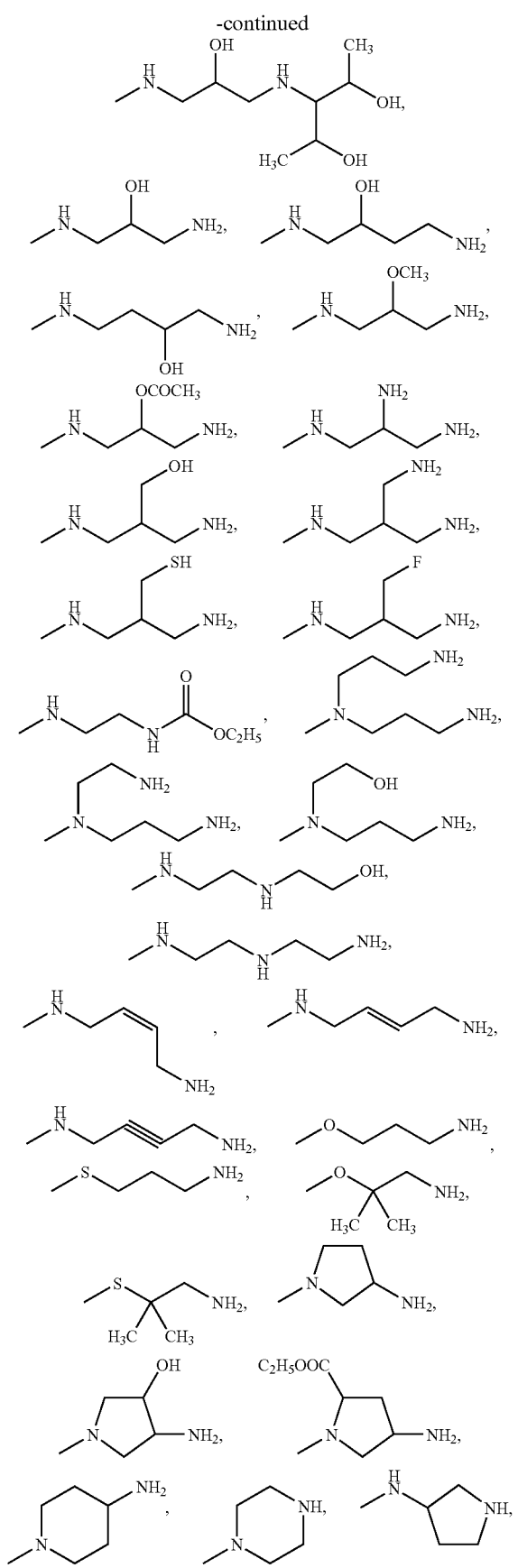
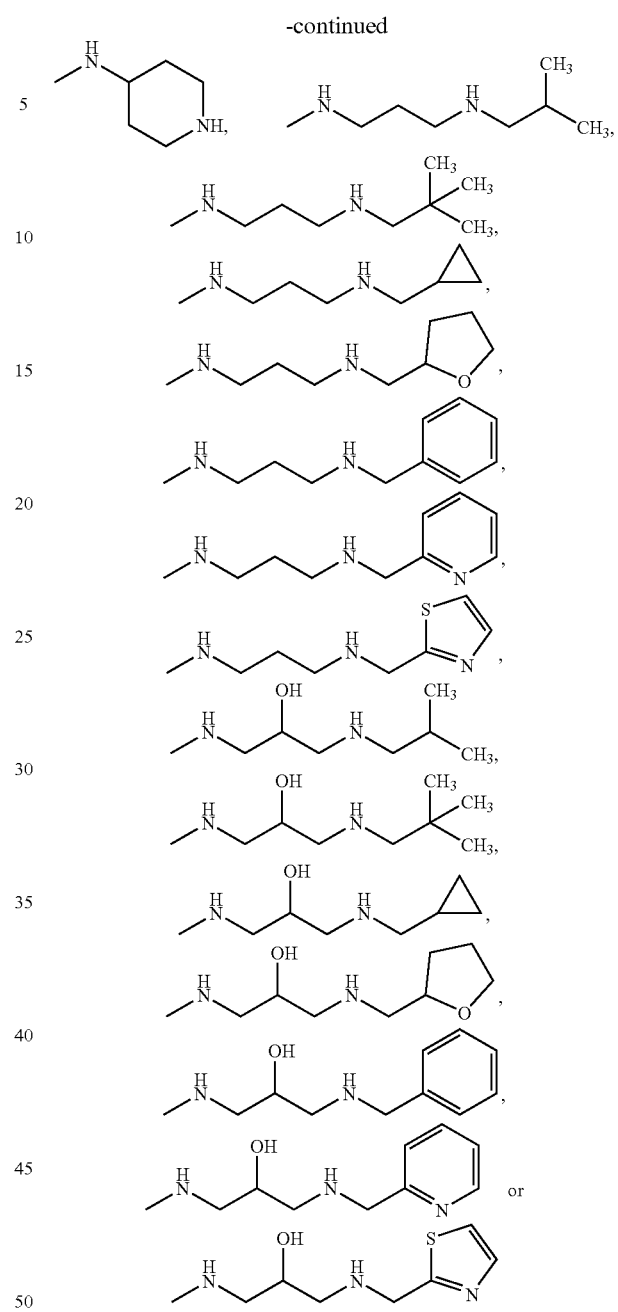

Examples of preferred compounds of Formula include;

N-(3-Amino-2-hydroxypropyl)-2(R)-[1-(2-ethylbutyryl)pyrrolidine-2(S)-carbonyl-amino]-3-naphthalen-2-yl-propionamide hydrochloride, N-(3-Amino-2-hydroxypropyl)-2(R)-[1-(2,2-dimethylpentanoyl)pyrrolidine-2(S)-carbonylamino]-3-naphthalen-2-yl-propionamide hydrochloride, N-(3-Methylamino-2-hydroxypropyl)-2(R)-[1-(2-ethylbutyryl)pyrrolidine-2(S)-carbonylamino]-3-naphthalen-2-yl-propionamide hydrochloride, N-(3-Amino-2-hydroxypropyl)-2(R)-[(2-benzoylamino-2-methyl)propionylamino]-3-naphthalen-2-yl-propionamide hydrochloride, N-(3-Amino-2-hydroxypropyl)-2(R)-[(2-benzensulfonylamino-2-methyl)propionylamino]-3-naphthalen-2-yl-propionamide hydrochloride, N-(3-Amino-2-hydroxypropyl)-2(R)-[(2-benzylcarbonylamino-2-methyl)propionyl]- 3-naphthalen-2-yl-propionamide hydrochloride, N-(3-Amino-2-hydroxypropyl)-2(R)-[2-(3-chloro-3-methylbutyrylamino)-2-methyl-propionylamino]-3-naphthalen-2-yl-propionamide hydrochloride, N-(3-Amino-2-hydroxypropyl)-2(R)-[1-(2,2-dimethylpropionyl)pyrrolidine-2-(S)-carbonylamino]-3-naphthalen-2-yl-propionamide hydrochloride, N-(3-Amino-2-hydroxypropyl)-2(R)-[1-(3,3-dimethylbutyryl)pyrrolidine-2-(S)carbonylamino]-3-naphthalen-2-yl-propionamide hydrochloride, N-(3-Amino-2-hydroxypropyl)-2(R)-[1-(2-propylpentanoyl)pyrrolidine-2(S)-carbonylamino]-3-naphthalen-2-yl-propionamide hydrochloride, N-(3-Amino-2-hydroxypropyl)-2(R)-[1-cyclohexylcarbonylpyrrolidine-2(S)-carbonylamino]-3-naphthalen-2-yl-propionamide hydrochloride, N-(3-Amino-2-hydroxypropyl)-2(R)-[1-cyclohexylacetylpyrrolidine-2(S)-carbonyl-amino]-3-naphthalen-2-yl-propionamide hydrochloride, N-(3-Amino-2-hydroxypropyl)-2(R)-[1-(4-tertbutyl-cyclohexylcarbonyl)-pyrrolidine-2(S)-carbonyl-amino]-3-naphthalen-2-yl-propionamide hydrochloride, N-(3-Amino-2-hydroxypropyl)-2(R)-[1-(benzoyl)pyrrolidine-2(S)-carbonyl-amino]-3-naphthalen-2-yl-propionamide hydrochloride, N-(3-Amino-2-hydroxypropyl)-2(R)-[1-(4-fluorobenzoyl)pyrrolidine-2(S)-carbonyl-amino]-3-naphthalen-2-yl-propionamide hydrochloride, N-(3-Amino-2-hydroxypropyl)-2(R)-[1-(2-ethylbutyryl)pyrrolidine-2(R)-carbonyl-amino]-3-naphthalen-2-yl-propionamide hydrochloride, N-(3-Amino-2-hydroxypropyl)-2(R)-[1-(isobutyloxycarbonyl)pyrrolidine-2(S)-carbonyl-amino]-3-naphthalen-2-yl-propionamide hydrochloride, N-(3-Amino-2-acetyloxypropyl)-2(R)-[1-(2-ethylbutyryl)pyrrolidine-2(S)-carbonyl-amino]-3-naphthalen-2-yl-propionamide hydrochloride, N-(3-Amino-2-hydroxypropyl)-2(R)-[1-(4-fuluorobenzoyl)piperidine-4-carbonyl-amino]-3-naphthalen-2-yl-propionamide hydrochloride, N-(3-Amino-2-hydroxypropyl)-2(R)-[2-(2-ethylbutyrylamino)-2-methyl-propionylamino]-3-naphthalen-2-yl-propionamide hydrochloride, N-(3-Amino-2-hydroxypropyl)-2(R)-[2-(4-fuluorobenzoylamino)-2-methylpropionyl-amino]-3-naphthalen-2-yl-propionamide hydrochloride, N-(3-Amino-2-hydroxypropyl)-2(R)-(1-benzoylamino)cyclohexylcarbonylamino-3-naphthalen-2-yl-propionamide hydrochloride, N-(3-Amino-2-hydroxypropyl)-2(R)-[1-(N-acetyl-N-phenylamino)propionylamino]-3-naphthalen-2-yl-propionamide hydrochloride, N-(3-Aminopropyl)-2(R)-[4-(N-methanesulfonyl-N-phenylamino)butyrylamino]-3-naphthalen-2-yl-propionamide hydrochloride, N-(3-Aminopropyl)-2(R)-[4-(N-phenyl-N-p-toluensulfonylamino)butyrylamino]-3 -naphthalen-2-yl-propionamide hydrochloride, N-(3-Amino-2-hydroxypropyl)-2(R)-[4-(N-cycloheptyl-N-methanesulfonylamino)butyrylamino]-3-naphthalen-2-yl-propionamide hydrochloride, N-(3-Amino-2-hydroxypropyl)-2(R)-[3-(N-cycloheptyl-N-methanesulfonylamino)-2-methylpropionylamino]-3-naphthalen-2-yl-propionamide hydrochloride, N-(3-Amino-2-hydroxypropyl)-2(R)-[3-(N-cyclohexyl-N-methanesulfonylamino)-2-methylpropionylamino]-3-naphthalen-2-yl-propionamide hydrochloride, N-(3-Amino-2-hydroxypropyl)-2(R)-[1-(N-cyclohexyl-N-ethoxycarbonylamino)-2-methylpropionylamino]-3-naphthalen-2-yl-propionamide hydrochloride, N-(3-Amino-2-hydroxypropyl)-2(R)-[1-(isobutyryl)pyrrolidine-2(S)-carbonylamino]-3-naphthalen-2-yl-propionamide hydrochloride, N-(3-Amino-2-hydroxypropyl)-2(R)-[1-(N,N-diethylaminocarbonyl)pyrrolidine-2(S)-carbonylamino]-3-naphthalen-2-yl-propionamide hydrochloride, N-(3-Methylaminopropyl)-2(R)-[1-(2-ethylbutyryl)pyrrolidine-2(S)-carbonylamino]-3-naphthalen-2-yl-propionamide hydrochloride, N-[3-(2-Hydroxypropylamino)-2-hydroxypropyl]-2(R)-[1-(2-ethylbutyryl)-pyrrolidine-2(S)-carbonylamino]-3-naphthalen-2-yl-propionamide hydrochloride, N-[3-(2-methylpropylamino)-2-hydroxypropyl]-2(R)-[1-(2,2-dimethylpropionyl)pyrrolidine-2-(S)-carbonylamino]-3-naphthalen-2-yl-propionamide hydrochloride, N-(3-Amino-2-hydroxypropyl)-2(R)-[1-(4-methyl-2-isobutylpentanoyl)pyrrolidine-2(S)-carbonylamino]-3-naphthalen-2-yl-propionamide hydrochloride, N-(3-Amino-2-hydroxypropyl)-2(R)-[1-(2,2-dimethylbutyryl)pyrrolidine-2(S)-carbonylamino]-3-naphthalen-2-yl-propionamide hydrochloride, N-[3-(2(R)-Benzyloxypropylamino)-2-hydroxypropyl]-2(R)-[1-(2-ethylbutyryl)pyrrolidine-2(S)-carbonylamino]-3-naphthalen-2-yl-propionamide hydrochloride, N-[2-(2-Amino-2-methylpropionylamino)ethyl]-2(R)-[1-(2,2-dimethylpentanoyl)pyrrolidine-2-(S)-carbonylamino]-3-naphthalen-2-yl-propionamide hydrochloride, N-[2-(2-Aminopropionylamino)ethyl]-2(R)-[1-(2-ethylbutyryl)pyrrolidine-2-(S)-carbonylamino]-3-naphthalen-2-yl-propionamide hydrochloride, N-(3-Amino-2-hydroxypropyl)-2(R)-[1-(2-ethylbutyryl)pyrrolidine-2(S)-carbonyl-amino]-3-(5,6,7,8-tetrahydro)naphthalen-2-yl-propionamide hydrochloride, N-[3-(2(R)-Hydroxypropylamino)-2-hydroxypropyl]-2(R)-[1-(4-methyl-2-isobutyl-pentanoyl)pyrrolidine-2(S)-carbonylamino]-3-naphthalen-2-yl-propionamide hydrochloride, N-[3-(2(R)-Hydroxypropylamino)-2-hydroxypropyl]-2(R)-[1-(2,2-dimethylpentanoyl)-pyrrolidine-2(S)-carbonylamino]-3-naphthalen-2-yl-propionamide hydrochloride, N-[3-(2(R)-Hydroxypropylamino)-2-hydroxypropyl]-2(R)-[2-benzoylamino-2-methyl-propionylamino]-3-naphthalen-2-yl-propionamide hydrochloride, N-Methyl-N-(3-aminoethyl)-2(R)-[1-(2,2-dimethylbutyryl)pyrrolidine-2(S)-carbonyl-amino]-3-naphthalen-2-yl-propionamide hydrochloride, N-[3-(2(R)-Benzyloxypropylamino)propyl]-2(R)-[1-(2-ethylbutyryl)pyrrolidine-2(S)-carbonylamino]-3-naphthalen-2-yl-propionamide hydrochloridev N-[3-Benzylaminopropyl]-2(R)-[1-(2-ethylbutyryl)pyrrolidine-2(S)-carbonylamino]-3-naphthalen-2-yl-propionamide hydrochloride, N-[3-(2(R)-Benzyloxypropylamino)-2(R or S)-hydroxypropyl]-2(R)-[1-(2-ethylbutyryl)-pyrrolidine-2(S)-carbonylamino]-3-naphthalen-2-yl-propionamide hydrochloride, N-[3-(2(R)-Benzyloxypropylamino)-2(S or R)-hydroxypropyl]-2(R)-[1-(2-ethylbutyryl)pyrrolidine-2(S)-carbonylamino]-3-naphthalen-2-yl-propionamide hydrochloride, N-[3-Phenethylaminopropyl]-2(R)-[1-(2-ethylbutyryl)pyrrolidine-2(S)-carbonylamino-3-naphthalen-2-yl-propionamide hydrochloride, N-[3-(2-methylpropylamino)propyl]-2(R)-[1-(2-ethylbutyryl)pyrrolidine-2-(S)-carbonyl-amino]-3-naphthalen-2-yl-propionamide hydrochloride, N-[3-(2-Phenoxyethylamino)propyl]-2(R)-[1-(2-ethylbutyryl)pyrrolidine-2-(S)-carbonyl-amino]-3-naphthalen-2-yl-propionamide hydrochloride, N-[3-(2-methylpropylamino)-2-hydroxypropyl]-2(R)-[1-(2-ethylbutyryl)-pyrrolidine-2(S)-carbonylamino]-3-naphthalen-2-yl-propionamide hydrochloride, N-[3-(2(R)-Methoxypropylamino)-2-hydroxypropyl]-2(R)-[1-(2-ethylbutyryl)-pyrrolidine-2(S)-carbonylamino]-3-naphthalen-2-yl-propionamide hydrochloride, N-[3-Aminopropyl]-2(R)-[1-(2,2-dimethylpropionyl)pyrrolidine-2(S)-carbonylamino]-3-naphthalen-2-yl-propionamide hydrochloride, N-[3-(2-methylpropylamino)propyl]-2(R)-[1-(2,2-dimethylpropionyl)pyrrolidine-2(S)-carbonylamino]-3-naphthalen-2-yl-propionamide hydrochloride, N-[3-Amino-2-methoxypropyl]-2(R)-[1-(2-ethylbutyryl)pyrrolidine-2(S)-carbonyl-amino]-3-naphthalen-2-yl-propionamide hydrochloride, N-[3-(2(R)-Methoxypropylamino)propyl]-2(R)-[1-(2,2-dimethylpropionyl)pyrrolidine-2(S)-carbonylamino]-3-naphthalen-2-yl-propionamide hydrochloride, N-[3-(2(R)-Methoxypropylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-(2-Methoxyethylamino)-2-hydroxypropyl]-2(R)-[1-(2-ethylbutyryl)pyrrolidine-2(S)-carbonylamino]-3-naphthalen-2-yl-propionamide hydrochloride, N-[3-(2(R)-Benzyloxypropylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-Aminopropyl]-2(R)-[2-benzoylamino-2-methylpropionylamino]-3-naphthalen-2-yl-propionamide hydrochloride, N-[3-(2-Methoxyethylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-(2,2-dimethylpropylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-Cyclohexylmethylamino-2-hydroxypropyl]-2(R)-[1-(2,2-dimethylpropionyl)-pyrrolidine-2(S)-carbonylamino]-3-naphthalen-2-yl-propionamide hydrochloride, N-[3-Benzylamino-2-hydroxypropyl]-2(R)-[1-(2,2-dimethylpropionyl)pyrrolidine-2-(S)carbonylamino]-3-naphthalen-2-yl-propionamide hydrochloride, N-[3-(2-Chlorobenzylamino)propyl]-2(R)-[1-(2,2-dimethylpropionyl)pyrrolidine-2(S)-carbonylamino]-3-naphthalen-2-yl-propionamide hydrochloride, N-[3-(2-Tetrahydrofuranylmethylamino)-2-hydroxypropyl]-2(R)-[1-(2,2-dimethyl-propionyl)pyrrolidine-2(S)-carbonylamino]-3-naphthalen-2-yl-propionamide hydrochloride, N-[3-Cyclopropylmethylamino-2-hydroxypropyl]-2(R)-[1-(2,2-dimethylpropionyl)-pyrrolidine-2(S)-carbonylamino]-3-naphthalen-2-yl-propionamide hydrochloride, N-[3-(2-Furfurylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-(2-Thenylamino)-2-hydroxypropyl]-2(R)-[1-(2,2-dimethylpropionyl)pyrrolidine-2(S)-carbonylamino]-3-naphthalen-2-yl-propionamide hydrochloride, N-[3-(4-Chlorobenzylamino)propyl]-2(R)-[1-(2,2-dimethylpropionyl)pyrrolidine-2(S)-carbonylamino]-3-naphthalen-2-yl-propionamide hydrochloride, N-[3-(2-Pyridylmethylamino)-2-hydroxypropyl]-2(R)-[1-(2,2-dimethylpropionyl)-pyrrolidine-2(S)-carbonylamino]-3-naphthalen-2-yl-propionamide dihydrochloride, N-[3-(2-Thiazolylmethylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-(2-Fluorobenzylamino)propyl]-2(R)-[1-(2,2-dimethylpropionyl)pyrrolidine-2(S)-carbonylamino]-3-naphthalen-2-yl-propionamide hydrochloride, N-[3-(N-Methyl-2-pyrrolylmethylamino)-2-hydroxypropyl]-2(R)-[1-(2,2-dimethyl-propionyl)pyrrolidine-2(S)-carbonylamino]-3-naphthalen-2-yl-propionamide hydrochloride, N-[3-(2-Fluorobenzylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-Aminopropyl]-2(R)-[1-(2-methoxy-2-methylpropionyl)pyrrolidine-2(S)-carbonylamino]-3-naphthalen-2-yl-propionamide hydrochloride, N-[3-(3-Pyridylmethylamino)-2-hydroxypropyl]-2(R)-[1-(2,2-dimethylpropionyl)-pyrrolidine-2(S)-carbonylamino]-3-naphthalen-2-yl-propionamide dihydrochloride, N-[3-(2-Benzyloxy-2-methylpropylamino)propyl]-2(R)-[1-(2,2-dimethylpropionyl)-pyrrolidine-2(S)-carbonylamino]-3-naphthalen-2-yl-propionamide hydrochloride, N-[3-(2,2-dimethylpropylamino)propyl]-2(R)-[1-(2-methoxy-2-methylpropionyl)-pyrrolidine-2(S)-carbonylamino]-3-naphthalen-2-yl-propionamide hydrochloride, N-[3-Aminopropyl]-2(R)-[1-(cyclopentylcarbonyl)pyrrolidine-2(S)-carbonylamino]-3-naphthalen-2-yl-propionamide hydrochloride, N-[3-(2-methylpropylamino)-2-hydroxypropyl]-2(R)-[1-(2-methoxy-2-methyl-propionyl)pyrrolidine-2(S)-carbonylamino]-3-naphthalen-2-yl-propionamide hydrochloride, N-[3-(2,2-dimethylpropylamino)-2-hydroxypropyl]-2(R)-[1-(2-methoxy-2-methyl-propionyl)pyrrolidine-2(S)-carbonylamino]-3-naphthalen-2-yl-propionamide hydrochloride, N-[3-(2-methylpropylamino)ethyl]-2(R)-[1-(2-ethylbutyryl)pyrrolidine-2(S)-carbonylamino]-3-naphthalen-2-yl-propionamide hydrochloride, N-[3-(2-methylpropylamino)butyl]-2(R)-[1-(2-ethylbutyryl)pyrrolidine-2(S)-carbonylamino]-3-naphthalen-2-yl-propionamide hydrochloride, N-[3-(2-Tetrahydrofuranylmethylamino)propyl]-2(R)-[1-(2,2-dimethylpropionyl)-pyrrolidine-2(S)-carbonylamino]-3-naphthalen-2-yl-propionamide hydrochloride, N-[3-Aminopropyl]-2(R)-1-(3,3-dimethyl-2-oxopentanoyl-carbonyl)pyrrolidine-2(S)-carbonylamino]-3-naphthalen-2-yl-propionamide hydrochloride, N-[3-(2-Ethylbutylamino)-2-hydroxypropyl]-2(R)-[1-(2-ethylbutyryl)-pyrrolidine-2(S)-carbonylamino]-3-naphthalen-2-yl-propionamide hydrochloride, N-[3-Aminopropyl]-2(R)-[1-(2-ethylbutyryl)-4(R)-hydroxypyrrolidine-2(S)-carbonyl-amino]-3-naphthalen-2-yl-propionamide hydrochloride, N-[3-(2-methylpropylamino)propyl]-2(R)-[1-(2-ethylbutyryl)-4(R)-hydroxypyrrolidine-2(S)-carbonylamino]-3-naphthalen-2-yl-propionamide hydrochloride, N-[3-Aminopropyl]-2(R)-[1-(2-isopropyl-3-methylbutyryl) pyrrolidine-2(S)-carbonyl-amino]-3-naphthalen-2-yl-propionamide hydrochloride, N-[3-(3-Bromobenzylamino)propyl]-2(R)-[1-(2,2-dimethylpropionyl)pyrrolidine-2(S)-carbonylamino]-3-naphthalen-2-yl-propionamide hydrochloride, N-[3-(4-Methoxybenzylamino)propyl]-2(R)-[1-(2,2-dimethylpropionyl)pyrrolidine-2(S)-carbonylamino]-3-naphthalen-2-yl-propionamide hydrochloride, N-[3-(2-methylpropylamino)propyl]-2(R)-[1-(2-methoxy-2-methylpropionyl)-pyrrolidine-2(S)-carbonylamino]-3-naphthalen-2-yl-propionamide hydrochloride, N-[2-Aminoethyl]-2(R)-[1-(2,2-dimethylpropionyl)pyrrolidine-2(S)-carbonylamino]-3-naphthalen-2-yl-propionamide hydrochloride, N-[3-Aminopropyl]-2(R)-[1-(2-methoxy-2-methylpropionyl)-4(R)-hydroxypyrrolidine-2(S)-carbonylamino]-3-naphthalen-2-yl-propionamide hydrochloride, N-[3-(2-Methylpropylamino)propyl]-2(R)-[1-(2-methoxy-2-methylpropionyl)-4(R)-hydroxypyrrolidine-2(S)-carbonylamino]-3-naphthalen-2-yl-propionamide hydrochloride, N-[3-Aminopropyl]-2(R)-[1-(2-ethoxy-2-methylpropionyl)pyrrolidine-2(S)-carbonyl-amino]-3-naphthalen-2-yl-propionamide hydrochloride, N-[3-(2-Methylpropylamino)propyl]-2(R)-[1-(2-ethoxy-2-methylpropionyl)pyrrolidine-2(S)-carbonylamino]-3-naphthalen-2-yl-propionamide hydrochloride, N-[3-(2-Methylpropylamino)butyl-2(R)-[1-(2-methoxy-2-methylpropionyl)-4(R)-hydroxypyrrolidine-2(S)-carbonylamino]-3-naphthalen-2-yl-propionamide hydrochloride, N-[3-(2-Methylpropylamino)-2-hydroxypropyl]-2(R)-[1-(2-ethoxy-2-methylpropionyl)-pyrrolidine-2(S)-carbonylamino]-3-naphthalen-2-yl-propionamide hydrochloride, N-[3-(2-Thenylamino)propyl]-2(R)-[1-(2,2-dimethylpropionyl)pyrrolidine-2(S)-carbonylamino]-3-naphthalen-2-yl-propionamide hydrochloride, N-[3-(4-Nitrobenzylamino)propyl]-2(R)-[1-(2,2-dimethylpropionyl)pyrrolidine-2(S)-carbonylamino]-3-naphthalen-2-yl-propionamide hydrochloride, N-[3-(3-Hydroxybenzylamino)propyl]-2(R)-[1-(2,2-dimethylpropionyl)pyrrolidine-2(S)-carbonylamino]-3-naphthalen-2-yl-propionamide hydrochloride, N-[3-Amino-2-hydroxypropyl]-2(R)-[1-(cyclopentylcarbonyl)pyrrolidine-2(S)-carbonylamino]-3-naphthalen-2-yl-propionamide hydrochloride, N-[3-(2-Ethylbutylamino)-2-hydroxypropyl]-2(R)-[1-(2,2-dimethylpropionyl)-pyrrolidine-2(S)-carbonylamino]-3-naphthalen-2-yl-propionamide hydrochloride, N-[3-(2-Hydroxy-2-methylpropylamino)propyl]-2(R)-[1-(2,2-dimethylpropionyl)pyrrolidine-2-(S)-carbonylamino]-3-naphthalen-2-yl-propionamide hydrochloride, N-[3-(4-Hydroxybenzylamino)propyl]-2(R)-[1-(2,2-dimethylpropionyl)pyrrolidine-2(S)-carbonylamino]-3-naphthalen-2-yl-propionamide hydrochloride, N-[3-(2-Methylpropylamino)propyl]-2(R)-[1-(2,2-dimethylbutyrylcarbonyl)pyrrolidine-2(S)-carbonylamino]-3-naphthalen-2-yl-propionamide hydrochloride, N-[2-(2-Hydroxyethylamino)ethyl]-2(R)-[1-(2,2-dimethylpropionyl)pyrrolidine-2(S)-carbonylamino]-3-naphthalen-2-yl-propionamide hydrochloride, N-[3-(2-methylpropylamino)-2-hydroxypropyl]-2(R)-[1-(2,2-dimethlpropionyl)-4(S)-fluoro-pyrrolidine-2(S)-carbonylamino]-3-naphthalen-2-yl-propionamide hydrochloride, N-[3-(2-methylpropylamino)-2(S)-hydroxypropyl]-2(R)-[1-(2,2-dimethylpropionyl)-pyrrolidine-2(S)-carbonylamino]-3-naphthalen-2-yl-propionamide hydrochloride, N-[3-(2-methylpropylamino)-2(R)-hydroxypropyl]-2(R)-[1-(2,2-dimethylpropionyl)-pyrrolidine-2(S)-carbonylamino]-3-naphthalen-2-yl-propionamide hydrochloride, N-[3-(2,2-dimethylropylamino)-2(S)-hydroxypropyl]-2(R)-[1-(2,2-dimethylpropionyl)-pyrrolidine-2(S)-carbonylamino]-3-naphthalen-2-yl-propionamide hydrochloride, N-[3-(2,2-dimethylropylamino)-2(R)-hydroxypropyl]-2(R)-[1-(2,2-dimethylpropionyl)-pyrrolidine-2(S)-carbonylamino]-3-naphthalen-2-yl-propionamide hydrochloride, N-[2-Aminoethyl]-2(R)-[1-(2-methoxy-2-methylpropionyl)pyrrolidine-2(S)-carbonyl-amino]-3-naphthalen-2-yl-propionamide hydrochloride, and N-[3-(2-Ethylbutylamino)propyl]-2(R)-[1-(2-methoxy-2-methylpropionyl)pyrrolidine-2(S)-carbonylamino]-3-naphthalen-2-yl-propionamide hydrochloride.

The compounds of the instant invention all have at least one asymmetric centers as noted by the asterisk in the structural Formula I. Additional asymmetric centers may be present on the molecule depending on the nature of the various substituents on the molecule.

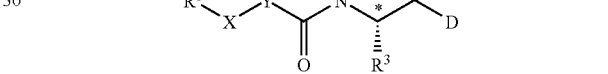

I

As a consequence of these chiral centers, the compounds of the present invention occur as racemates, mixtures of enantiomers and as individual enantiomers, as well as diastereomers and mixtures of diastereomers. Each such asymmetric center will produce two optical isomers and it is intended that all such optical isomers, as separated, pure or partially purified optical isomers or racemic mixtures thereof, be included within the ambit of the instant invention.

The term "R" and "S" are used herein as commonly used in organic chemistry to donate specific configuration of a chiral center. The term "R" (rectus) refers to that configuration of a chiral center with a clockwise relationship of group priorities (highest to second lowest) when viewed along the bond toward the lowest priorities group. The term "S" (sinister) refers to that configuration of a chiral center with a counterclockwise relationship of a group priorities (highest to second lowest) when viewed along the bond toward the lowest priority group. The prioity of groups is based on their atomic number (in order of decreasing atomic number).

In the case of the asymmetric center represented by the asterisk in Formula I, it has been found that the compound in which the $R^3$ is below the plane of the structure, as seen in Formula Ia, is more active and thus more preferred over the compound in which the $R^3$ is above the plane of the structure.

This invention encompasses the pharmaceutically acceptable salts of the compounds defined by Formula I. A compound of this invention can possess a sufficiently acidic, a sufficient basic, or both functional groups, and accordingly react with any of a number of organic or inorganic acids, and organic or inorganic bases, to form pharmaceutically acceptable salts. The term "pharmaceutically acceptable salts" as used herein, refers to salts of the compounds of above Formula I which are substantially non-toxic to live organism.

Typically pharmaceutically acceptable salts include those salts prepared by reaction of the compounds of the present invention with pharmaceutically acceptable mineral or organic acid or an organic or inorganic base. Such salts are of acid addition and base addition.

The instant compounds are generally isolated in the form of their pharmaceutically acceptable acid addition salts, such as the salts derived from using inorganic and organic acids. Examples of such inorganic acids include hydrochloric acid, hydrobromic acid, hydroiodic acid, nitric acid, sulfuric acid, phosphoric acid, and the like. Examples of such organic acids include acetic acid, trifluroacetic acid, propionic acid, maleic acid, succinic acid, maleic acid, oxalic acid, methanesulfonic acid, p-toluenesulfonic acid, and the like. Preferred pharmaceutically acceptable acid addition salts are those formed with mineral acids such as hydrochloric acid and hydrobromic acid, and those formed with organic acids as methanesulfonic acid, trifluroacetic acid and maleic acid.

The instant compounds are also generally isolated in the form of their pharmaceutically acceptable base addition salts, such as salts derived from using inorganic and organic bases. Such bases useful in preparing the salts of this invention thus include sodium hydroxide, potassium hydroxide, ammonium hydroxide, potassium carbonate, sodium carbonate, sodium bicarbonate, potassium bicarbonate, calcium carbonate, and the like. The sodium and potassium salts are particularly preferred.

It should be recognized that the particular counter ion forming a part of any salt of this invention is usually not of a critical nature, so long as the salt as a whole is pharmaceutically acceptable and as long as the counter ion does not contribute undesired qualities to the salt as a whole.

This invention further encompasses the pharmaceutically acceptable solvates of the compounds of Formula I. Most compounds of the Formula I can be combined with solvents such as water, methanol, ethanol, and acetonitrile to form pharmaceutically acceptable solvates such as corresponding hydrate, metanolate, ethanolate, and acetonitrilate.

Throughout the instant application the following abbreviations are used with the following meanings:
Boc: t-butoxycarbonyl
Bop benzotriazole-1-yloxy-tris-(dimethylamino)-phosphonium-hexafluoro-phosphate
CBZ: benzyloxycarbonyl
DCC: dicyclohexyl carbodiimido
DMF: N,N-dimethylformamide
DEAD: Diehtyl azodicarboxylate
EDC: 1-(3-dimethylaminopropyl)-3-ethylcarbodiimide hydrochloride
FAB-MAS: FAB Mass Spectrum
Fmoc: 9-fluorenylmethyloxycarbonyl
HOBt: 1-hydroxybenzotriazole
MHz: Megaherz
NMM: N-Methylmorpholine
Pht: phthaloyl
NMR: Nuclear Magnetic Resonance
Nal: Naphthylalanine
TFA: trifluoroacetic acid The preparation of compounds of Formula I ($R^1$, $R^2$, $R^3$, X, Y, or D are as defined described above) of the present invention may be carried out in sequential or convergent synthetic routes.

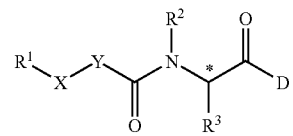

I

Syntheses detailing the preparation of the compounds of Formula I in a sequential or convergent manner are presented in the following Schemes 1–12.

The compounds having a Formula I are prepared from intermediates such as 1 ($R^1$, X, or Y are as defined described above).

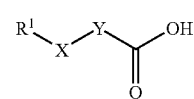

1

Typical intermediates 3 ($R^1$, $R^2$, $R^3$, X, or Y are as defined described above) may be synthesized as shown in Scheme 1. Ester derivatives 2 ($R^2$ and $R^3$ are as defined described above, $R^{19}$ is $C_{1-5}$ alkyl) are, in some cases, commercially available or are prepared by a number of methods well known in the art. Coupling of intermediate 1 with ester derivative 2 is carried out by standard peptide coupling reaction conditions using an acid activating agent such as EDC, DCC, and BOP in an inert solvent such as dichloromethane or DMF, with or without the presence of a catalyst such as HOBt.

The skills required in carrying out the reaction and purification of the resulting reaction products are known to those in the art. Purification procedure includes crystallization, and/or chromatography.

Scheme 1

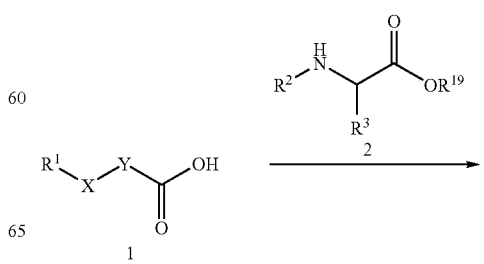

Scheme 2

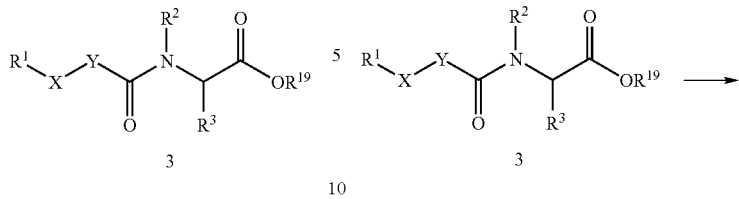

Conversion of typical intermediates 3 to intermediate acids 4 may be accomplished by a number of methods known in the art described in Scheme 2; for example, methyl and ethyl esters can be hydrolyzed with sodium hydroxide, potassium hydroxide, or lithium hydroxide in a protic solvent like aqueous methanol, ethanol, dioxane. In addition, removal of benzyl ester can be achieved by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane. t-Butyl ester can be removed with acid like hydrogen chloride or TFA in a various solvents including dioxane and dichloromethane.

Diamino derivatives 5, 6, 7 ($R^7$, $R^8$, or $R^9$ are as defined described above, Z is protecting Group) are either commercially available or can be synthesized by routine methods. Compounds of Formula $I_a$ and intermediates 8, 9 are synthesized in following scheme 3. Coupling a carboxylic acid 4 with an amine 5, 6 or 7 are carried out using acid activating agent such as EDC, DCC, and Bop in a solvent such as dichloromethane or DMF with or without the presence of such as HOBt. Purification of the resulting reaction products are known to those in the art. Purification procedure includes crystallization, and/or chromatography using as a carrier like a silica gel.

Scheme 3

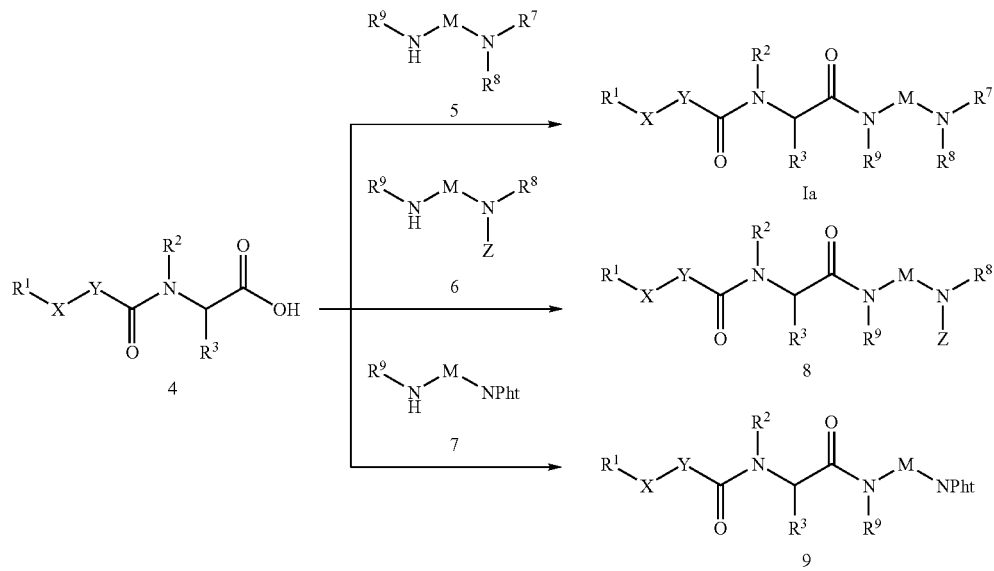

The preparation of compounds of Formula I and intermediate 8, 9 may also be carried out in convergent synthetic route illustrated in Scheme 4, 5, 6, 7, 8, 9, 10, 11 or 12. The protected amino acid derivatives 10 are, in some cases, commercially available, where the protecting $Z^1$ is, for example, Boc or CBZ or Fmoc groups. Other protected amino acid derivatives 10 can be prepared by a number of methods well known in the literature. Intermediate 11, 12, or 13 are prepared by coupling of protecting amino acids derivatives 10 with diamino derivatives 5, 6, or 7.

Scheme 4

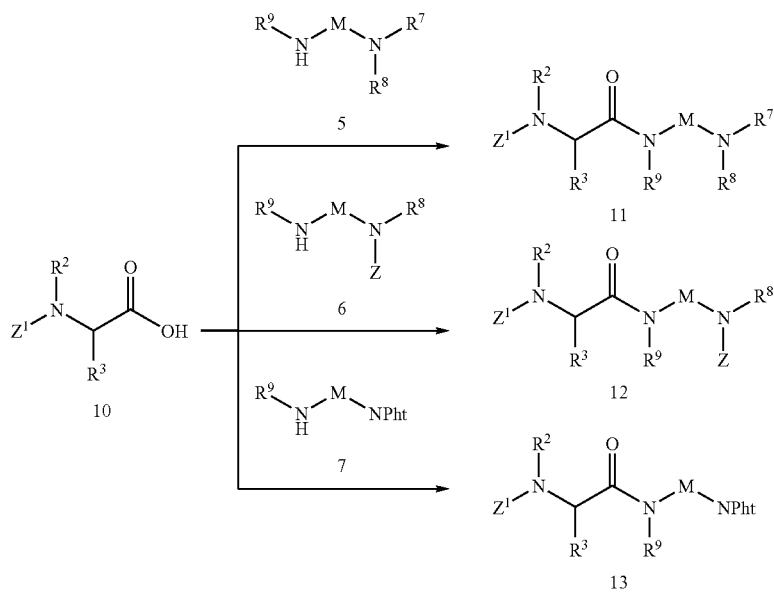

Conversion of 11, 12, or 13 to intermediate 14, 15, or 16 can be achieved as shown in Scheme 5 by removal of the protecting group $Z^1$ (CBZ, Boc, Fmoc, Formyl, etc.). CBZ and Boc are used extensively in the synthesis, and their removal conditions are known to those skilled in the art. For example, removal of CBZ groups can be carried out by a number of methods known in the art; for example, catalytic hydrogenation with hydrogen in the presence of a noble metal or its oxide such as palladium on activated carbon in a protic solvent such as ethanol. In the cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of Boc protecting groups is carried out in a solvent such as ethyl acetate or dioxane or methylene chloride or methanol, with a strong acids, such as TFA or hydrochloric acid or hydrogen chloride gas. Removal of Fmoc groups is carried out with a organic base such as dimethylamine or piperazine. Removal of formyl groups is carried out in solvent such as water or methanol with a acid such as hydrochloric acid or hydrazine-acetic acid. Conditions required to remove other protecting groups which may be present and can be found in Green, T. and Wuts, P. G. M., Protective Group in Organic Synthesis, John Wiley & Sons, Inc., New York, N.Y. 1991. It should be recognized that Z is different from $Z^1$ and is stable to the removal conditions of $Z^1$. For example, when $Z^1$ is CBZ or Fmoc, Boc as L is preferred.

Scheme 5

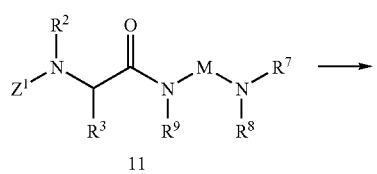

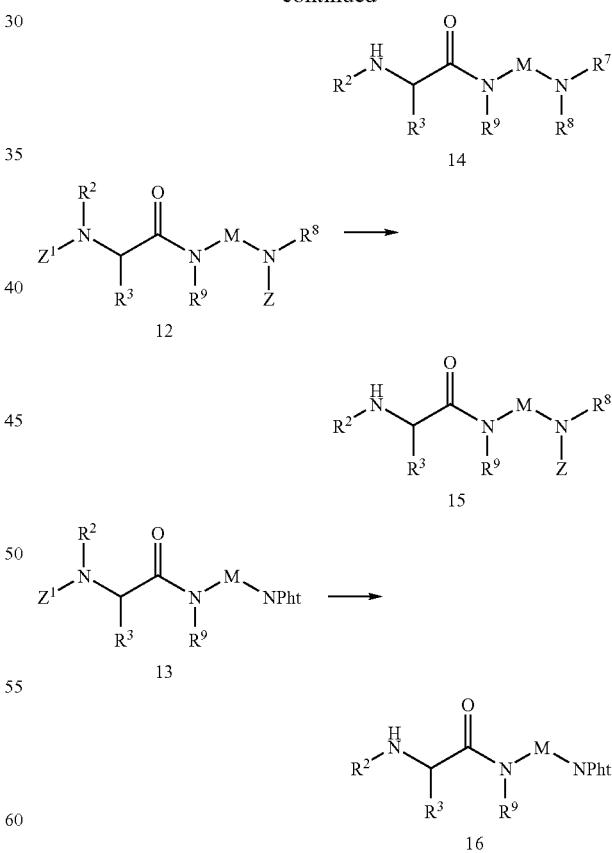

Compounds of Formula $I_a$ in the present invention and intermediates 8, 9 are synthesized as shown in Scheme 6. Coupling a carboxylic acid 1 with an amine 14, 15, or 16 is achieved using a condition described above.

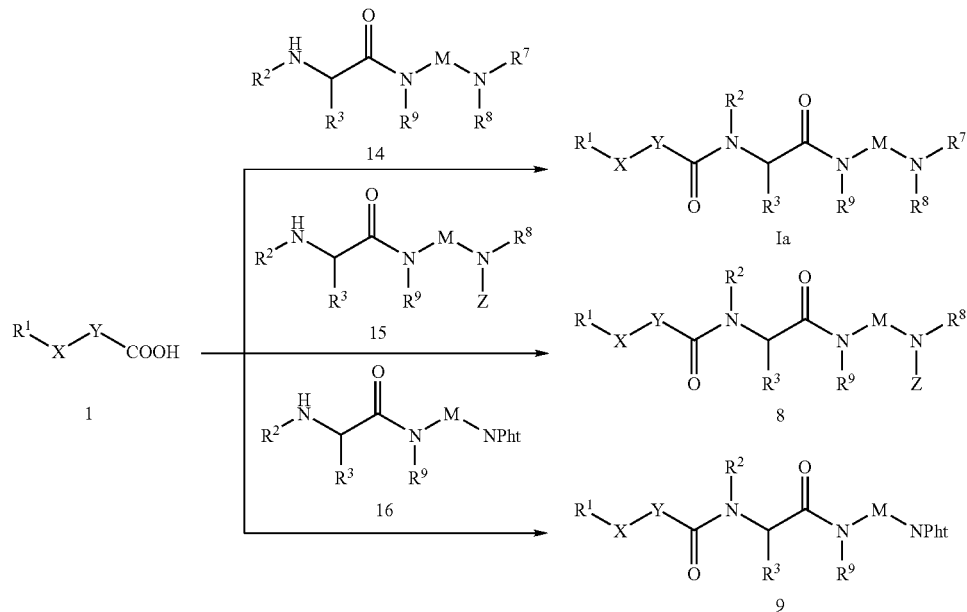

Conversion of intermediates 8, 9 to compounds of Formula $I_b$, $I_c$ may be accomplished as illustrated in Scheme 7. Removal of protecting group Z may be carried out by various conditions. Deprotection of phthaloyl group is achieved in a solvent such as methanol, ethanol, or dioxane with hydrazine.

Compounds of Formula $I_d$ in the present invention and intermediate 19 are synthesized as shown in Scheme 8. Coupling an amide$I_b$ with a carboxylic acid 17 or 18 is achieved using a condition described above.

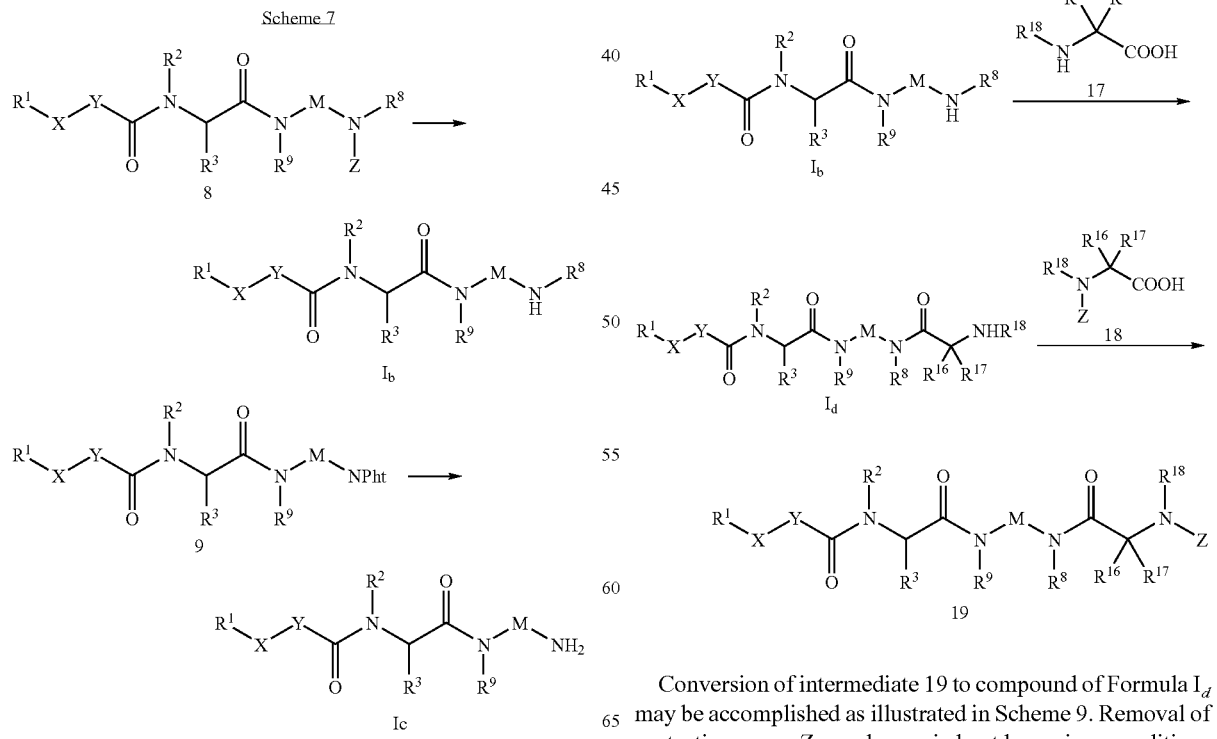

Conversion of intermediate 19 to compound of Formula $I_d$ may be accomplished as illustrated in Scheme 9. Removal of protecting group Z may be carried out by various conditions described above.

Scheme 9

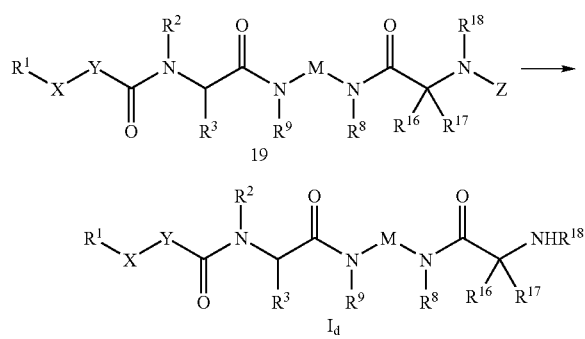

Oxydation of olefin 20, illustrated in Scheme 10, with peroxide, for example, perbenzoic acid, metachloroperbenzoic acid, peracetic acid, monoperphthalic acid, pertrifluoroacetic acid, or hydrogen peroxide in a solvent such as dichloromethane, chloroform, ethyl acetate, methanol, ethanol, acetic acid, DMF or $H_2O$ gives epoxide 21 which is an important intermediate for preparation of compound of Formula $I_e$.

Scheme 10

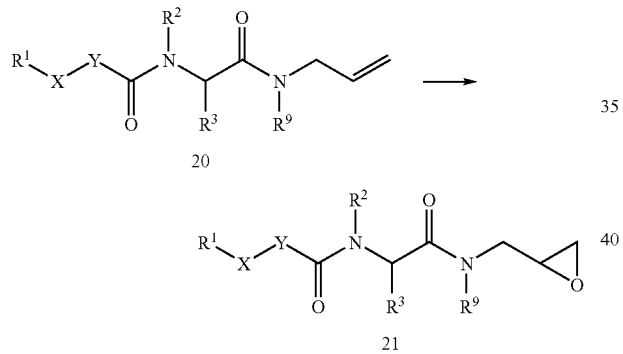

Addition of amine 22 to epoxide 21 in a solvent such as dichloromethane, chloroform, benzene, ethylether, methanol, ethanol, illustrated in Scheme 11, affords compound of Formula $I_e$. Purification of the resulting reaction products are known to those in the art. Purification procedure includes crystallization, and/or chromatography using as a carrier like a silica gel.

Scheme 11

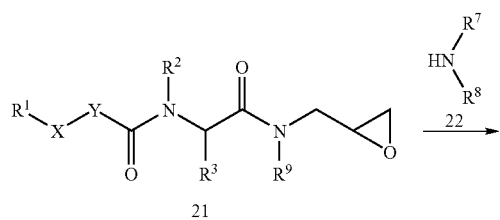

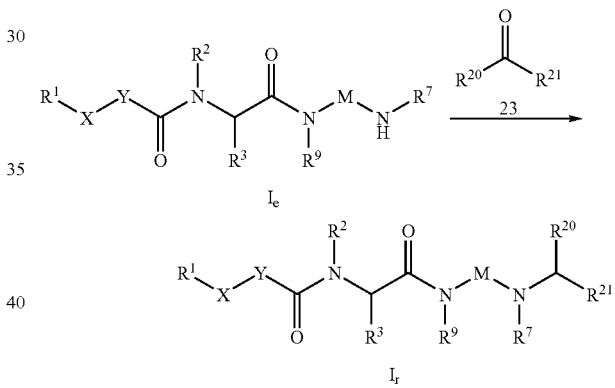

Compounds of Formula $I_f$ in the present invention are also synthesized as shown in Scheme 12. The reductive alkylation may be performed by first producing an iminium intermediate by reaction of the compound of formula $I_e$ ($R^1$, $R^2$, $R^3$, $R^8$, $R^9$, X or Y are as defined described above) with a carbonyl containing compound 23 ($R^{20}$ and $R^2$ are as defined described above) under conventional conditions, for example in an inert solvent (such as methnol, ethanol, DMF) in the presence of dehydro reagents and then reducing it, with a reducing agent (e.g. sodium borohydride, sodium cyanoborohydride, sodium triacetoxyborohydride, borane, sodium, sodium amalgam, zinc-acetic acid), by hydrogenation using hydrogen on Pd/C, or by electrochemical reduction using lead, copper, platinium as an electrode.

Scheme 12

The growth hormone releasing compounds of Formula I are useful in vitro as unique tools for understanding how growth hormone secretion is regulated at the pituitary levels. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine.

The compounds of the Formula I can also be employed to investigate the possible negative or positive feedback effects of some the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, sheep, cow and the like to accelerate and increase their rate and extent of growth, to improve feed efficiency and to increase milk production in such animals. In addition, these compounds can be administered to humans in vivo as a diagnostic tool to directly determine whether the hypothalamus-pituitary system is capable of releasing growth hormone. For example, the compounds of Formula I can be administered to humans. Serum samples taken before and after such administration can be assayed for growth hormone. Comparison of the amounts of growth hormone in each of these samples would be a means for directly determining the ability of the patient's hypothalamus-pituitary system to release growth hormone.

Accordingly, the present invention includes within its scope pharmaceutical comprising, as an active ingredient, at least one of the compounds of Formula I in association with a pharmaceutical carrier or diluent. Optionally, the active ingredient of the pharmaceutical composition can comprise an anabolic agent in addition to at least one of the compounds of Formula I or another composition which exhibits a different activity, an antibiotic growth permittant or an agent to treat osteoporosis or in combination with a corticosteroid to minimized the catabolic side effects or with other pharmaceutically active materials wherein the combination enhances efficiency and minimizes side effects.

Growth promoting and anabolic agents include, but are not limited to, THR, diethyl-stibesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. No. 4,411,890 and publications WO 89/07110, WO89/07111 and B-HT 920 as well as hexarelin and GHRP-2 as described in WO 93/04081 or growth hormone releasing hormone (GHRH also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing facor, IGF-1, or IGF-2. For example, a compound of the present invention may be used in combination with IGF-1 for the treatment or prevention of obesity. In addition, a compounds of this invention may be employed in onjunction with retinoic acid to improve the condition of musculature and skin that results from intrinsic agents.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purpose of stimulating the release of endogenous growth hormone can have the same effects or uses as growth hormone itself. These varied uses may be summarized as follows; stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisolism and Cushing's syndrome; treatment of peripheral neuropathies; replacement of growth hormone in stressed patients; treatment of osteochondrodysplasias, Noonans syndrome, sleep disorders, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndrome; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosupprssed patients and to enhance antibody response following vaccination; increasing the total lymphocyte count of a human, in particular, increasing the T4/T8-cell ratio in a human with a depressed T4/T8-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis in the frail elderly; stimulation of osteoblasts, bone remodeling, and cartilage growth; treatment of male infertility; stimulation of the immune system in companion animals and treatment of disorders of aging in companion animals; growth promotant in livestok; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of, osteoporosis; catabolic illness; immune deficiency, including that in individuals with a depressed T4/T8-cell ratio; hip fracture; musculoskeletal impairment in the elderly; growth hormone deficiency in adults or in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illness induced or facilitated by corticotropin releasing factor or stress- and anxiety-related disorders, including stress-induced depression, and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skills in the art that there are numerous compounds now being used in an effort to treat the diseases or therapeutic indications enumerated above. Combinations of these therapeutic agents some of which have also been mentioned above with the growth hormone secretagogues of this invention will bring additional complementary, and often synergistic properties to enhance the growth promortant, anabolic and desirable properties of these various therapeutic agents. In these combinations, the therapeutic agents and the growth hormone secretagogues of this invention may independently present in dose ranges from one one-hundredth to one times the dose levels which are effective when these compounds and secretagogues are used singly. Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" Trends in Endocrinol. Metab., 4, 19–25 (1993). Bisphosphonates with these utilities include alendronate, tiludronate, diethyl-APD, risedronate, etidronate, YM-175, clodronate, pamidronate, and BM-210995. Accordingly to their potency, oral daily dosage levels of the bisphosphonate of between 0.1 mg and 5 g and daily dosage levels of the growth hormone secretagogues of this invention of between 0.01 mg/kg and 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Combined therapy to enhance the healing of bone fractures, wounds or burns can be illustrated by combinations of growth factors, especially bFGF (basic fibroblast growth factor), and the growth hormone secretagogues of this invention (Canalis, E. Clin. Orthop., 1985, 193, 246–263; Kawaguchi, H. Endocrinology, 1994, 135, 774–781; Nakamura, T. et al., Endocrinology, 1995, 136, 1276–1284; Shida, J. et al., Journal of Orthopaedic Research, 1996, 14, 265–272).

Combined therapy to enhance the healing of bone fractures, wounds or burns can be illustrated by combinations of growth factors, especially PDGF (platelet-derived growth factor), and the growth hormone secretagogues of this invention (Stile, C. D. et al., Proc. Natl. Acad. Sci. USA, 1979, 76, 1279–1283; Chen, Y. et al., J. Cell Physiol., 1989, 140, 59–67).

Osteoporosis and other bone disorders may also be treated with compounds of this invention in combination with calcitonin, estrogen, raloxifene and calcium supplements such as calcium citrate or calcium carbonate.

Anabolic effects especially in the treatment of geriatric male patients are obtained with compounds of this invention in combination with anabolic steroids such as oxymetholone, methyltestosterone, fluoxymesterone and stanozolol.

Other uses of the instant compounds will be apparent from the following references;

Amato, et al., Journal of Clinical Endocrinology and Metabolism 77 (6):1671–1676 (1993), Bengtsson, et al., Journa of Clinical Endocrinology and Metabolism 76 (2):309–317 (1993), Binnerts, et al., Clinical Endocrinology 37:79–87 (1992);

Bowers, et al., Journal of Clinical Endocrinology and Metabolism 76 (4):817–823 (1993), Cuneo, et al., Journal of Applied Physiology 70 (2):688–694 (1991), Cuneo, et al., Journal of Applied Physiology 70 (2):695–700 (1991), Degerblad, et al., Acta Endocrinologica 126:387–393 (1992), Eden, et al., Arteriosclerosis and Thrombosis 13829:296–301 (1993), Hartman, et al., Horm Research 40:37–47 (1993), Ho, et al., Horm Research 40:80–86 (1993), Jogensen, et al., Acta Endocrinologica 125:449–453 (1991), Jogensen, et al., The Lancet June 3:1221–1224 (1989), Lambert, et al., Clinical Endocrinology 37:111–115 (1992), McCauley, et al., Horm Research 33:52–54 (1990), Moller, et al., Clinical Endocrinology 39:403–408 (1993), O'Halloran, et al., Journal of Clinical Endocrinology and Metabolism 76 (5):1344–1348 (1993), Orme, et al., Clinical Endocrinology 37:453–459 (1992), Rodriguez-Amao, et al., Horm Research 39:87–88 (1993), Rosen, et al., Clinical Endocrinology 40:111–116 (1994), Rosen, et al., Acta Endocrinologica 129:195–200 (1993), Rudman, et al., The New England Journal of Medicine 323 (1):1–6 (1990), Salmon, et al., The New England Journal of Medicine 321 (26):1797–1803 (1989), Shibasaki, et al., Journal of Clinical Endocrinology and Metabolism 58 (1):212–214 (1984), Sonksen, et al., Acta Paediatr Scand [Suppl] 379:139–146 (1991), Tauber, et al., Journal of Clinical Endocrinology and Metabolism 76 (5):1135–1139 (1993), Vandeweghe, et al., Clinical Endocrinology 39:409–415 (1993), Whitehead, et al., Clinical Endocrinology 36:45–52 (1992), Bercu, et al., U.S. Pat. No. 5,246,920.

Additionally, the most potent compounds of this invention can be used as GH antagonists. It is known that hypothalamic hormones that are super agonists can also used as antagonists. For example super agonists of Gonadotropin Releasing Hormone (GnRH) such as Gonadorelin and Leuprolide act either as agonists or antagonists depending on the method of administration. The action of the GnRH super agonists are summarized in Goodman and Gilmans, The Pharmacological Basis of Therapertics, 8th ED., McGraw Hill Inc., p. 1353 (1993). By analogy, it is believed the continuous administration of the compounds of formula I will lead to down-regulation of the growth response. These molecules can therefore be used as functional antagonists of pituitary GH secretion, thereby antagonizing GH or IGF-1.

The uses of such antagonists of GH secretion include but are not limited to; treatment of excess GH secretion as in acromegaly or gigantism; in cancer of the breast, colon and prostate; in diabetes especially in Type I adolescent patients to counteract the dawn phenomenon; and Type I and Type II patients to directly control blood glucose, and to control the long-term affects of diabetes, as for example in retinopathy.

The compounds of this invention can be administered by oral, parenteral (e.g., intramuscular, intraperitoneal, intravenous or subcutaneous injection or infusion, or implant), nasal, pulmonary, vaginal, rectal, sublingual, or topical routes of administration and can be formulated in dosageforms appropriate for each route of administration.

Accordingly, the present invention includes within its scope for pharmaceutical composition comprising, as active ingredient, at least one of the compounds of Formula I in association with a pharmaceutical acceptable carrier. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with a growth factor such as bFGF (basic fibroblast growth factor) for treatment of patients recovering from major surgery, bone fractures, wounds, burns or with other pharmaceutically active materials wherein the combination enhances efficacy and minimizes side effects.

Solid dosage forms for oral administration include capsules, tablets, pills, powders and granules. In such solids dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tables and pills can additionally be prepared with enteric coatings.

Liquid dosage forms for oral administration include pharmaceutically acceptable emulsion, solutions, suspensions, syrups, the elixirs containing inert diluents commonly used in the art, such as water. Besides such inert diluents, compositions can also include adjuvants, such as wetting agents, emulsifying and suspending agents, sweetening, flavoring, and perfuming agents.

Preparations according to this invention for parenteral administration include sterile aqueous or non-aqueous solutions, suspensions, or emulsions. Examples of non-aqueous solvent or vehicles are propylene glycol.

Composition for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effects, on the route of administration, and on the duration of the treatment. Generally, dosage levels of between 0.0001 to 100 mg/kg of body weight daily are administered to patients and animals, e.g., to obtain effective release of GH.

A preferred dosage range is 0.01 to 10.0 mg/kg of body weight daily.

Preparation

[Preparation 1]

Preparation of
Diethylacetyl-L-proryl-D-3-(2-naphthyl)alanine, 7

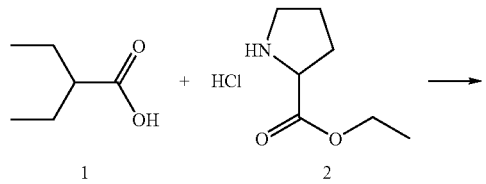

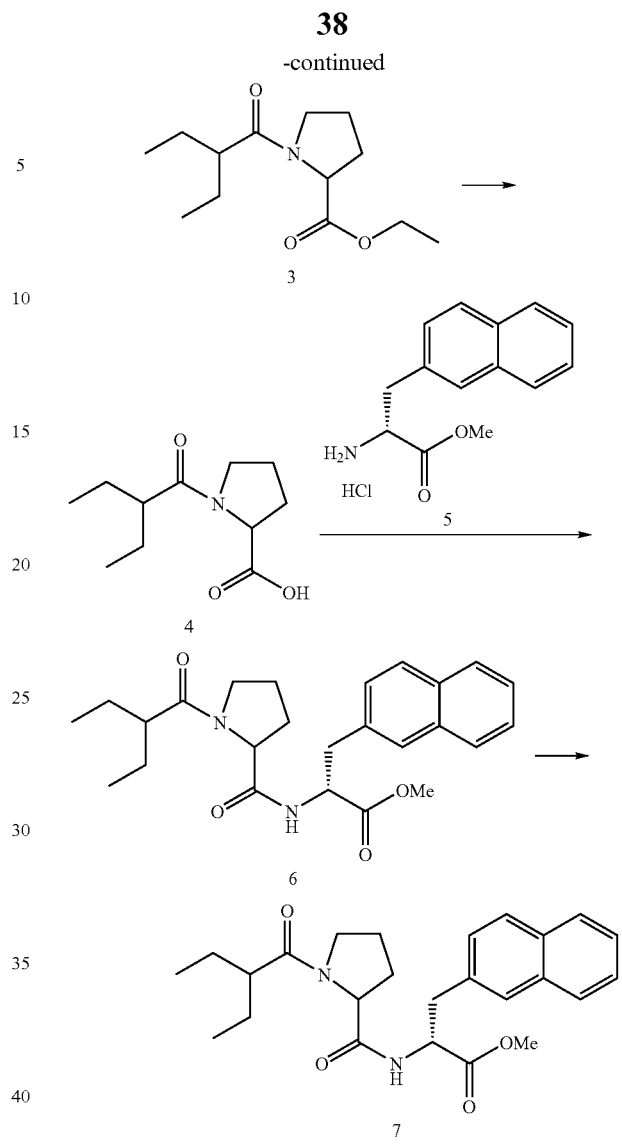

N-(2-Ethylbutyryl)-2(S)-pyrrolidine-carboxylic acid ethylester, 3

To dichloromethane solution (350 ml) of 2-ethyl butanoic acid 5.68 g (48.9 mmol) under cooling on ice-water, HOBt 6.76 g (50 mmol), EDC 9.6 g (50 mmol) were added, stirring was continued for 30 min. 2(S)-pyrrolidine-carboxylic acid ethylester hydrochloride 8 g (45 mmol), NMM 4.55 g (45 mmol) were added to the reaction mixture and then stirred at room temperature for overnight. After then, the reaction mixture was washed with water, 1% sodium hydroxide solution, and then water sequentially. The organic layer was dried over sodium sulfate and the solvents were removed in vacuo. Purification by silica gel chromatography gave a desired product as an oil (8.16 g). NMR was consistent with the desired title product.

$^1$H-NMR (270 MHz, CDCl$_3$)δ: 0.88 (3H, t), 0.96 (3H, t,), 1.26 (3H, t), 1.50 (2H, m), 1.67 (2H, m), 1.85–2.30 (4H, m), 2.38 (1H, m), 3.57 (1H, m), 3.70 (1H, m), 4.18 (2H, q), 4.51 (1H, m).

N-(2-Ethylbutyryl)-2(S)-pyrrolidine-carboxylic acid, 4

To methanol solution (13 ml) of N-(2-ethylbutyryl)-2(S)-pyrrolidine-carboxylic acid ethylester 1.46 g (6.05 mmol), 2N—NaOH solution (6.5 ml) was added, and stirring was continued at room temperature for 2 hours. The reaction mixture was cooled on ice-bath, and adjusted to pH2 with 6N—HCl solution. The reaction mixture was concentrated in vacuo, and the residue was dissolved in chloroform, washed with water, and then dried over anhydrous sodium sulfate. The solvents were removed in vacuo to yield 1.35 g of desired product as an oil. NMR was consistent with the desired title product.

$^1$H-NMR (270 MHz, CDCl$_3$)δ: 0.90 (6H, t), 1.54 (2H, m), 1.67 (2H, m), 2.01 (3H, m), 2.47 (2H, m), 3.54 (1H, m), 3.66 (1H, m).

Diethylacetyl-L-prolyl-D-3-(2-naphthyl)alanine methyl ester, 6

To DMF solution (40 ml) of dietylacetyl-L-proline 1.54 g (7.22 mmol) under cooling on ice-water, HOBt 1.2 g (8.88 mmol), EDC 1.6 g (8.35 mmol) were added and stirring was continued for 30 min. D-3-(2-naphthyl)alanine methyl ester hydrochloride 1.83 g (6.86 mmol), NMM 0.8 g (7.91 mmol) were added to the reaction mixture and then stirred at room temperature for overnight. The reaction mixture was then poured into 100 ml of sodium hydrogen bicarbonate, extracted with 100 ml of chloroform. Chloroform layer was washed with water, dried over sodium sulfate and the solvents were removed by vacuum. Purification of the residue by silica gel chromatography gave a desired product 2.97 g. The FAB-MS was consistent with the desired title intermediate.

FAB-MSS: m/z 425 (M+H)$^+$

Diethylacetyl-L-prolyl-D-3-(2-naphthyl)alanine, 7

To methanol (30 ml) and dioxane (30 ml) solution of diethylacetyl-L-prolyl-D-3-(2-naphthyl) alanine methyl ester 2.91 g (6.88 mmol) under cooling on ice-water, 2N—NaOH solution (8 ml) was added, and stirring was continued for 3 hours. The solvent was removed by evaporation, and the residue was dissolved in water (20 ml). The reaction mixture was cooled on ice-bath, and adjusted to pH2 with 1N—HCl solution. Formed precipitate was collected by filtration and then dried. Purification of the precipitate by silica gel chromatography gave a desired product 2.66 g. The NMR and FAB-MS spectra were consistent with the desired title product.

$^1$H-NMR (270 MHz, CDCl$_3$)δ: 0.65–0.90 (6H, m), 1.30–1.65 (4H, m,), 1.70–2.15 (4H, m), 2.31 (1H, m), 3.15–3.65 (4H, m), 4.45–4.60 (1H, m), 4.85–4.95 (1H, m (dd)), 5.50 (1H, bs), 7.15–7.85 (8H, m).

FAB-MS: m/z 411 (M+H)$^+$

[Preparation 2]

Preparation of N-(3-Amino-2-hydroxypropyl)phthalimide hydrochloride, 10

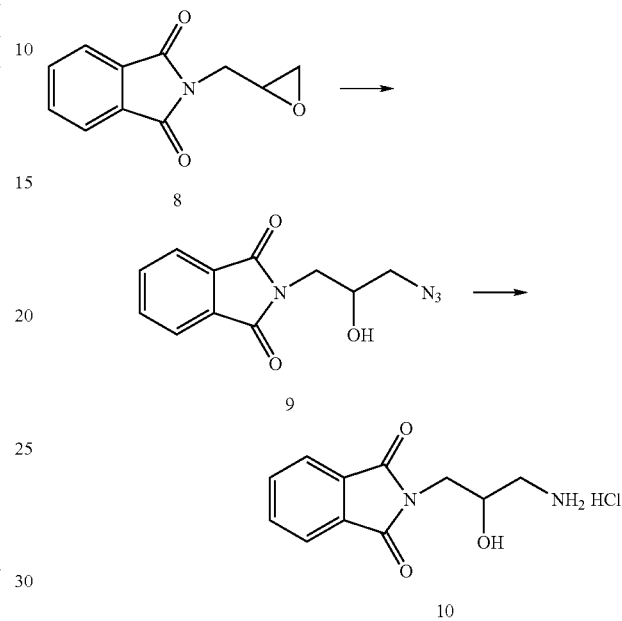

N-(3-Azido-2-hydroxypropyl)phthalimide, 9

To DMF solution (400 ml) of N-(2,3-epoxypropyl)phthalimide 58.8 g (0.29 mol), sodium azide 37.6 g (0.58 mol) and ammonium chloride 18.5 g (0.35 mol) were added, and stirred at 90° C. for 3 hours. The reaction mixture was cooled to room temperature, and then filtered. The filtrate was evaporated to dryness. The residue was dissolved in benzene (800 ml), washed with water, brine and water sequentially and then dried over sodium sulfate. The solvent was removed in vacuo. The desired product was further purified by silica gel chromatography. 66.3 g of desired product was obtained. The NMR spectra were consistent with the desired title intermediate.

$^1$H-NMR (270 MHz, CDCl$_3$)δ: 2.91 (1H, d), 3.37–3.50 (2H, m,), 3.86 (2H, d), 4.05–4.12 (1H, m), 7.72–7.79 (2H, m), 7.85–7.90 (2H, m).

N-(3-Amino-2-hydroxypropyl)phthalimide hydrochloride. 10

To ethanol solution (240 ml) of N-(3-azido-2-hydroxypropyl)phthalimide 10 g (40.3 mol), 10% Pd—C (1 g) and concentrated hydrochloric acid solution 7.84 ml (80.6 mmol) were added sequentially. To the reaction mixture, hydrogen was introduced at 2 kgf/cm$^2$ atm. and hydrogenated at room temperature for 6 hours. After removal of catalyst by filtration, catalyst was washed with EtOH/DMF (1:1) solution (300 ml) and then combined filtrate was evaporated to dryness. Addition of EtOH to the residue gave crystal of desired product as hydrogen chloride salt. Crystal was collected by filtration and dried under reduced pressure at 40° C. to afford 5.3 g of the product. The NMR spectra were consistent with the desired title intermediate.

$^1$H-NMR (270 MHz, DMSO-d$_6$)δ: 2.66–2.76 (1H, m), 2.98–3.10 (1H, m,), 3.37–3.71 (2H, m), 4.00–4.10 (1H, m), 5.60–5.85 (1H, m), 7.82–7.90 (4H, m), 8.10 (3H, bs).

[Preparation 3]

Preparation of
N-(3-Amino-2(S)-hydroxypropyl)phthalimide, 10a

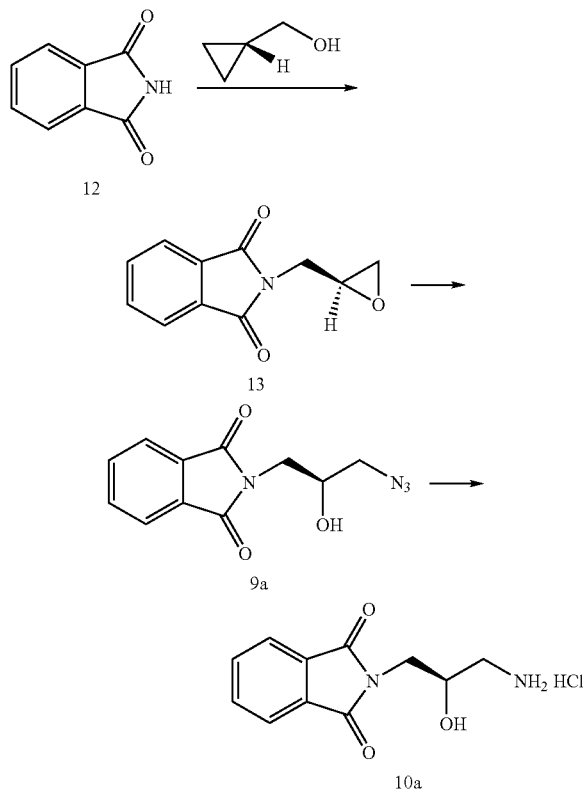

N-(2(R), 3-Epoxypropyl)phthalimide, 13

To THF solution (400 ml) of (R)-(+)-glycidol 2.47 g (32 mmol), phthalimide 7 g (47.6 mmol), triphenyl phosphine 14.3 g (54.5 mmol) and molecular shieve 4 Å 30 g were added at room temperature and then DEAE 8.7 g (50 mmol) was added dropwise under cooling on ice-bath. The reaction mixture was allowed to stand at room temperature overnight. Molecular shieve was removed by filtration and filtrate was evaporated to dryness in vacuo. The desired product was further purified by silica gel chromatography. 4.9 g of desired product was obtained as an oil. The NMR spectra were consistent with the desired title intermediate.

$^1$H-NMR (270 MHz, CDCl$_3$)δ: 2.69 (1H, t), 2.82 (1H, t,), 3.20–3.28 (1H, m), 3.89 (2H, dq), 7.71–7.77 (2H, m), 7.80–7.90 (2H, m).

N-(3-Azide-2(R)-hydrooxypropyl)phthalimide, 9a

To DMF solution (20 ml) of N-(2(R), 3-epoxypropyl)phthalimide 2.51 g (12.4 mmol), sodium azide 1.61 g (24.7 mmol) and ammonium chloride 0.79 g (14.9 mmol) were added, and stirred at 80° C. for 3 hours. The reaction mixture was allowed to stand at room temperature overnight. Benzene (50 ml) and distilled water (50 ml) were poured into the reaction mixture and organic layer was washed with water, brine sequentially, dried over anhydrous magnesium sulfate. Magnesium sulfate was removed by filtration, and filtrate was evaporated in vacuo. Further purification by silica gel chromatography gave 1.96 g of desired product. The NMR, FAB-MS spectra were consistent with the desired title intermediate.

$^1$H-NMR (270 MHz, CDCl$_3$)δ: 3.03 (1H, d), 3.36–3.49 (2H, m,), 3.85 (2H, d), 4.05–4.13 (1H, m), 7.73–7.78 (2H, m), 7.84–7.90 (1H, m).

FAB-MS: m/z 247 (M+H)$^+$

N-(3-Amino-2(S)-hydroxypropyl)phthalimide hydrochloride, 10a

To EtOH solution (80 ml) of N-(3-azido-2(R)-hydroxypropyl)phthalimide 1.96 g (7.69 mmol), 10% Pd—C (200 mg) and concentrated hydrochloric acid solution 1.4 ml were added sequentially. To the reaction mixture, hydrogen was introduced at 2 kgf/cm$^2$ atm. and then stirring was continued at room temperature overnight. After removal of catalyst by filtration, catalyst was washed with EtOH/DMF (1:1) solution (60 ml) and then combined filtrate was evaporated to dryness. Addition of EtOH to the residue gave crystal of desired product as a hydrogen chloride salt. Crystal was collected by filtration and dried under reduced pressure at 40° C. to afford 1.28 g of the product. The NMR spectra were consistent with the desired title intermediate.

$^1$H-NMR (270 MHz, DMSO-d$_6$)δ: 2.49–2.81 (1H, m), 2.98–3.05 (1H, m,), 3.52–3.70 (2H, m), 4.03 (1H, bs), 5.75 (1H, d), 7.47–7.55 (1H, m), 7.83–8.33 (6H, m).

[Preparation 4]

Preparation of
D-3-(2-Naphthyl)alanyl-3-amino-2-hydroxypropyl carbamic acid t-butylester, 14

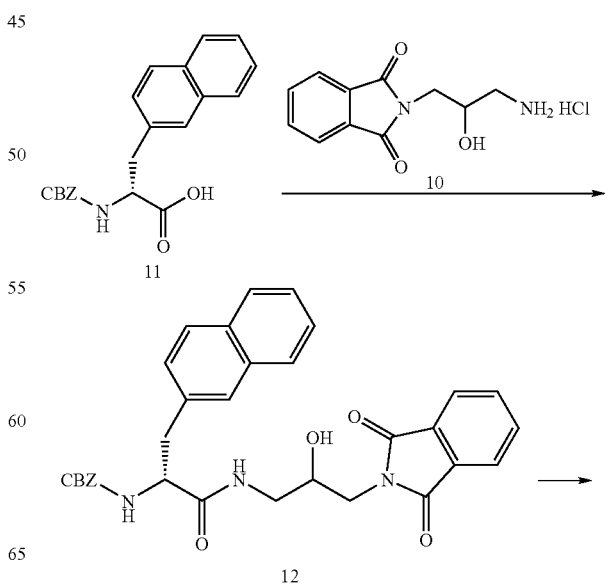

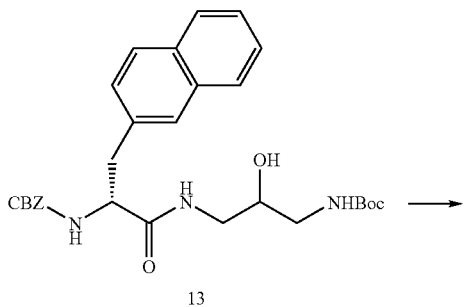

13

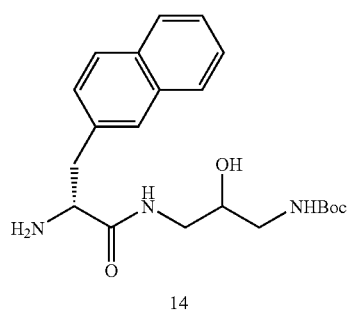

14

CBZ-D-3-(2-Naphthyl)alanyl-3-amino-2-hydroxypropyl-phthalimide, 12

To DMF solution (100 ml) of CBZ-D-3-(2-naphthyl)alanine 9.0 g (25.8 mmol) under cooling on ice-water, HOBt 3.8 g (28 mmol), EDC 5.4 g (28 mmol) were added, stirring was continued for 30 min. N-(3-Amino-2-hydroxypropyl)phthalimide hydrochloride 6 g (23.4 mmol), NMM 2.8 g (28 mmol) were added to the reaction mixture and then stirred at room temperature overnigth. The reaction mixture was poured into saturated sodium bicarbonate solution (400 ml) and formed precipitate was collected by filtration, washed with water. Purification by silica gel chromatography gave a desired product (11.3 g). NMR, FAB-MS spectra were consistent with the desired title product.

$^1$H-NMR (270 MHz, CDCl$_3$)δ: 3.00–3.55 (6H, m), 3.79 (1H, bd, J=19.1 Hz,), 4.55 (1H, dd, J=7.3 Hz), 5.04 (2H, s), 5.50–5.60 (1H, m), 6.65–6.80 (1H, m), 7.20–7.45 (8H, m), 7.65–7.85 (8H, m).

FAB-MS: m/z 552 (M+H)$^+$

CBZ-D-3-(2-Naphthyl)alanyl-3-amino-2-hydroxypropyl-carbamic acid t-butylester, 13

To EtOH solution (285 ml) of CBZ-D-3-(2-naphthyl)alanyl-3-amino-2-hydroxypropyl-phthalimide 11.3 g (20 mmol), hydrazine hydrate 2 g (40 mmol) was added and refluxed for 1.5 hours. After removed the solvent in vacuo, the residue was suspended in chloroform (145 ml) and treated with Di-t-butyl dicarbonate 6.6 g (30 mmol) under stirring at room temperature overnight. The reaction mixture was evaporated to dryness. Further purification by silica gel chromatography gave 7.73 g of desired product. The NMR, FAB-MS spectra were consistent with the desired title intermediate.

$^1$H-NMR (270 MHz, CDCl$_3$)δ: 1.40 (9H, s), 2.80–2.95 (2H, m), 3.22 (4H, d, J=6.9 Hz,), 3.56 (1H, bs), 4.51 (1H, dd, J=6.9 Hz), 4.90–5.10 (1H, m), 5.03 (2H, s), 5.53 (1H, d, J=7.6 Hz), 6.70 (1H, bs), 7.20–7.85 (13H, m)

FAB-MS: m/z 522 (M+H)$^+$

D-3-(2-Naphthyl)alanyl-3-amino-2-hydroxypropyl carbamic acid t-butylester, 14

To DMF solution (50 ml) of CBZ-D-3-(2-naphthyl)alanyl-3-amino-2-hydroxypropylcarbamic acid t-butylester 8.3 g (16 mmol), 10% Pd—C (3 g) was added and hydrogenated at 30° C., 3.0 atm. for 20 hours. After removal of catalyst by filtration, filtrate was evaporated to dryness. Further purification by silica gel chromatography gave 5.95 g of desired product. The NMR, FAB-MS spectra were consistent with the desired title intermediate.

$^1$H-NMR (270 MHz, DMSO-d$_6$)δ: 1.46 (9H, s), 1.81 (2H, s), 2.70–3.05 (3H, m), 3.10–3.25 (2H, m), 3.45–3.55 (2H, m), 5.00 (1H, d, J=4.621 Hz), 6.65 (1H, bs), 7.35–7.50 (3H, m), 7.79 (1H, s), 7.80–8.00 (4H, m).

FAB-MS: m/z 388 (M+H)$^+$

EXAMPLE

The process for preparing compounds of Formula I and preparations containing them is further illustrated in the following examples, which however, are not to be construed as limiting.

The structures of the compounds are confirmed by either nuclear magnetic resonance (NMR) or mass spectrometry (MS). NMR shifts (δ) are given in parts per million (ppm) and only selected peaks are given. Column chromatography was carried out using the technique described by W. C. Still et al, J. Org. Chem. 1978, 43, 2923–2925 on Shin-Etsu Chemical silica gel. Compounds used as starting materials are either known compounds or compounds which can readily be prepared by methods known per se.

Example 1 (Method I)

N-(3-Amino-2-hydroxypropyl)-2(R)-1-(2-ethylbutyryl)pyrrolidine-2(S)-carbonylamino]-3-naphthalene-2-yl-propionamide hydrochloride

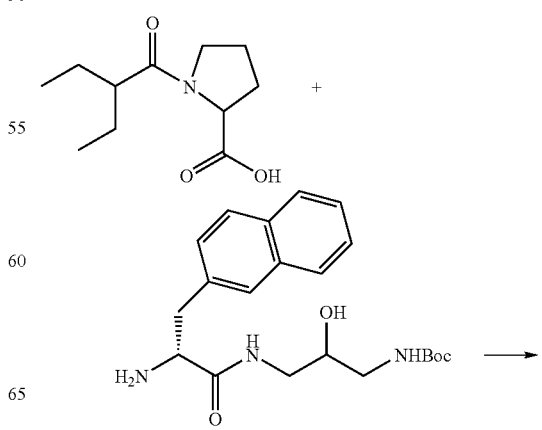

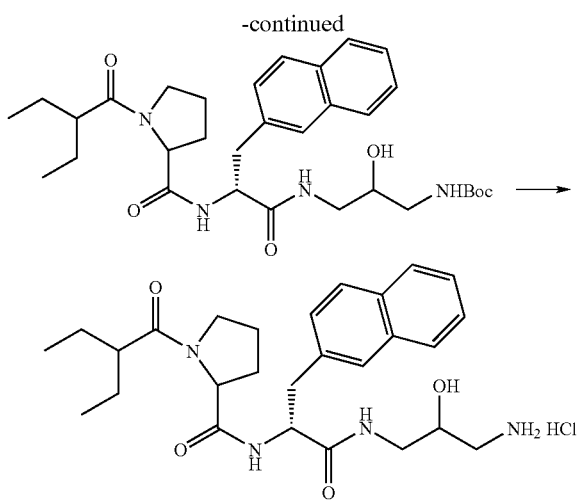

To DMF solution (7 ml) of N-(2-ethylbutyryl)-2(S)-pyrrolidine carboxylic acid 337 mg (1.58 mmol) under cooling on ice-water, HOBt 216 mg (1.6 mmol), EDC 306 mg (6 mmol), D-3-(2-naphthyl)alanyl-3-amino-2-hydroxypropyl carbamic acid t-butylester 589 mg were added sequentially, stirring was continued overnight. Solvent was removed in vacuo, and the residue was dissolved in chloroform. Organic layer was washed with water, 1% sodium hydroxide, water sequentially and dried over anhydrous sodium sulfate. Chloroform was removed by evaporation and further purification by silica gel chromatography gave a desired intermediate (770 mg) as an oil.

To ethylacetate solution (10 ml) of the oil (770 mg) under cooling on ice-water, 4N—HCl/ethylacetate (10 ml) was added, and stirring was continued at room temperature for 2 hours. Solvent was removed by evaporation in vacuo. To the residue, ethylether was added and formed precipitate was collected by filtration, and then dried. Desired product (513 mg) was obtained as a powder. NMR, FAB-MS spectra were consistent with the desired title product.

$^1$H-NMR (270 MHz, DMSO-$d_6$)δ: 0.79 (6H, t), 1.20–1.55 (5H, m), 1.67 (2H, m), 1.85 (1H, m), 2.38 (1H, m), 2.66 (1H, m), 2.95 (2H, m), 3.05–3.40 (3H, m), 3.47 (2H, m), 3.79 (1H, m), 4.27 (1H, m), 4.54 (1H, m), 5.65 (1H, bs), 7.46 (3H, m), 7.70 (1H, s), 7.75–8.00 (6H, m), 8.16 (1H, m), 8.48 (1H, m).

FAB-MS: m/z 483 (M+H)$^+$

Compounds of examples 2~19, 22, 23, 27, 28, 32~34, 41~85, 105, 106, 109, 132, 133, 211 were synthesized by using similar method of example 1.

Example 20 (Method II)

N-(3-Amino-2-hydroxypropyl)-2(R)-[1-(2-ethylbutyryl)pyrrolidine-2(S)-carbonylamino]-3-naphthalene-2-yl-propionamide hydrochloride

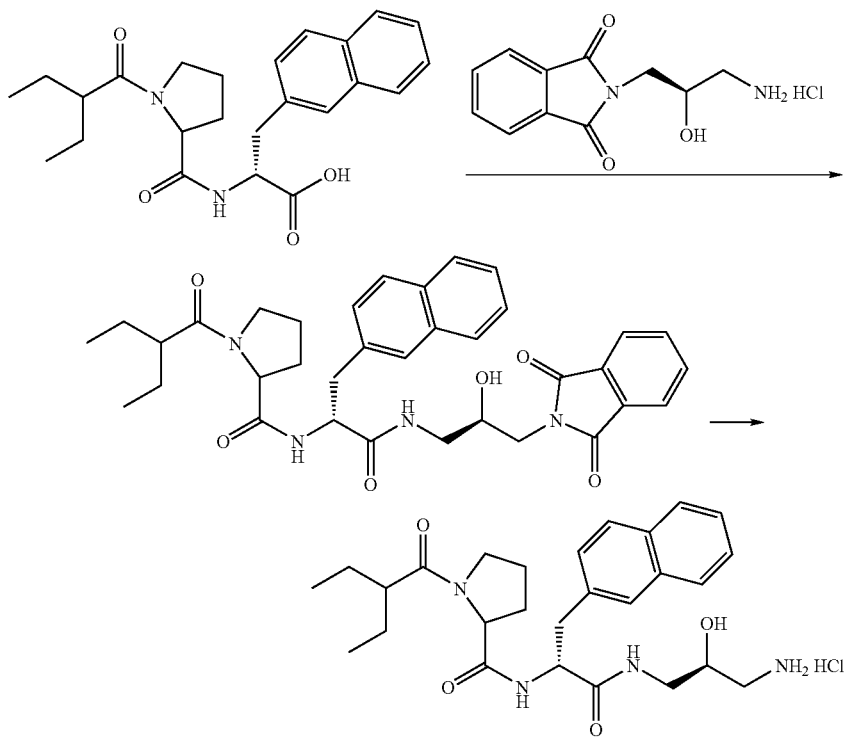

To DMF solution (6 ml) of diethylacetyl-L-proryl-D-3-(2-naphthyl)alanine 180 mg (0.44 mmol) under cooling on ice-water, HOBt 65 mg (0.48 mmol), EDC 100 mg (0.52 mmol) were added, stirring was continued for 30 min.

N-(3-Amino-2(S)-hydroxypropyl)-phthalimide hydrochloride 103 mg (0.4 mmol), NMM 50 mg (0.5 mmol) were added and stirred at room temperature overnight. Solvent was removed in vacuo. Further purification by silica gel chromatography gave a desired intermediate (146 mg). NMR, FAB-MS spectra were consistent with the desired intermediate.

$^1$H-NMR (270 MHz, CDCl$_3$)δ: 0.60–0.90 (6H, m), 1.20–1.50 (4H, m), 1.80–2.35 (5H, m), 3.05–3.75 (8H, m), 4.10–4.20 (2H, m), 4.85–5.00 (2H, m), 6.65 (1H, d, J=9.2), 7.40–7.90 (12H, m).

FAB-MS: m/z 613 (M+H)$^+$

To EtOH solution (6 ml) of the above intermediate (146 mg) under cooling on ice-water, hydrazine hydrate 25 mg (0.5 mmol) was added and refluxed for 3.5 hours. After removing the solvent in vacuo, the residue was suspended in chloroform (10 ml) and treated with Di-t-butyl dicarbonate 110 mg (0.5 mmol) under stirring at room temperature overnight. The reaction mixture was evaporated to dryness. Further purification by silica gel chromatography gave 120 mg of desired intermediate protected with Boc.

To ethylacetate solution (1 ml) of the above intermediate (120 mg) under cooling on ice-water, 4N—HCl/ethylacetate (1 ml) was added, and stirring was continued at room temperature for 2 hours. Solvent was removed by evaporation in vacuo. To the residue, ethylether was added and formed precipitate was collected by filtration, and then dried. Desired product (100 mg) was obtained as a powder. NMR, FAB-MS spectra were consistent with the desired title product.

$^1$H-NMR (270 MHz, DMSO-d$_6$)δ: 0.80 (6H, t), 1.30–1.55 (5H, m), 1.66 (2H, m), 1.85 (1H, m), 2.39 (1H, m), 2.67 (1H, m), 2.96 (2H, m), 3.05–3.40 (3H, m), 3.47 (2H, m), 3.81 (1H, m), 4.28 (1H, m), 4.54 (1H, m), 4.70 (1H, bs), 7.46 (3H, m), 7.71 (1H, s), 7.79–8.00 (5H, m), 8.18 (1H, m), 8.45 (1H, m).

FAB-MS: m/z 483 (M+H)$^+$

Compounds of examples 21, 24~26, 29, 38~40, 86, 87~104, 107, 108, 142, 154, 155, 158, 159, 162, 164, 165, 191~193, 204, 206, 208, 209, 212, were synthesized by using similar method of example 20.

Example 30 (Method III)

N-[2-(2-Aminoacetamino)ethyl]-2(R)-[1-(2-ethylbutyryl)pyrrolidine-2(S)-carbonylamino]-3-naphthalene-2-yl-propionamide hydrochloride

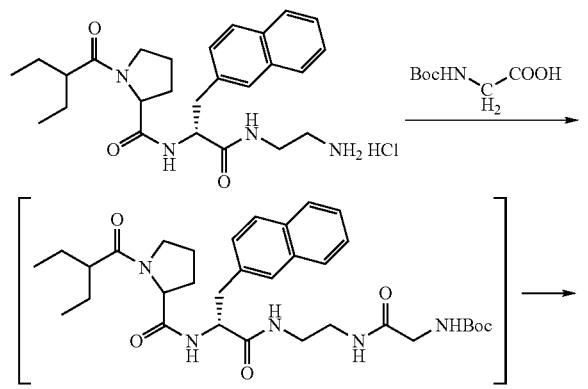

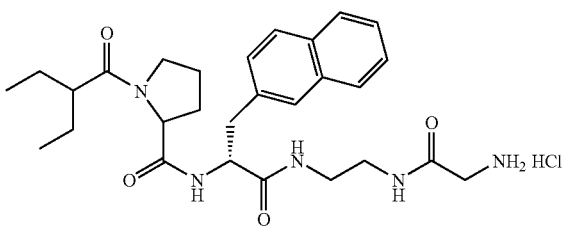

To DMF solution (3 ml) of Boc-glycine 52.4 mg (0.3 mmol) under cooling on ice-water, HOBt 40.5 mg (0.3 mmol), EDC 57.5 mg (0.3 mmol) were added and stirring was continued for 30 min. N-[(2-Aminoethyl)-2(R)-[1-(2-ethylbutyryl)pyrrolidine-2(S)-carbonylamino] -3-naphthalene-2-yl-propionamide hydrochloride 146 mg (0.3 mmol), NMM 30.3 mg (0.3 mmol) were added and stirred at room temperature overnight. Solvent was removed in vacuo, and the residue was dissolved in chloroform. Organic layer was washed with water, 1% sodium hydroxide, water sequentially and dried over anhydrous sodium sulfate. Chloroform was removed by evapaoration and further purification by silica gel chromatography gave a desired intermediate (170 mg) as an oil.

To ethylacetate solution (3.3 ml) of the oil (170 mg) under cooling on ice-water, 4N—HCl/ethylacetate (3.3 ml) was added, and stirring was continued at room temperature for 2 hours. Solvent was removed by evaporation in vacuo. To the residue, ethylether was added and formed precipitate was collected by filtration, and then dried. Desired product (513 mg) was obtained as a powder. NMR, FAB-MS spectra were consistent with the desired title product.

$^1$H-NMR (270 MHz, DMSO-d$_6$)δ: 0.80 (6H, t), 1.42 (5H, m), 1.60–2.00 (3H, m), 2.39 (1H, m), 2.96 (1H, m), 3.05–4.05 (9H, m), 4.30 (1H, t), 4.49 (1H, m), 7.46 (3H, m), 7.70 (1H, s), 7.82 (3H, m), 8.10 (4H, bs), 8.53 (2H, m).

FAB-MS: m/z 510 (M+H)$^+$

Compounds of examples 36, 37, 110~117, were synthesized by using similar method of example 30.

Example 35 (Method IV)

N-(3-Methylamino-2-hydroxypropyl)-2(R)-[1-(2-ethylbutyryl)pyrrolidine-2(S)-carbonyl amino]-3-naphthalene-2-yl-propionamide hydrochloride

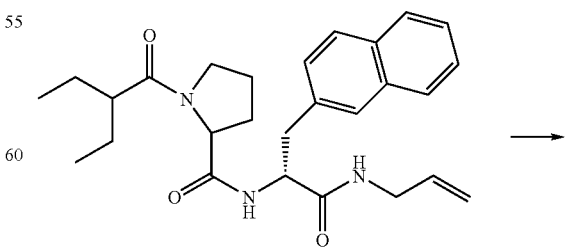

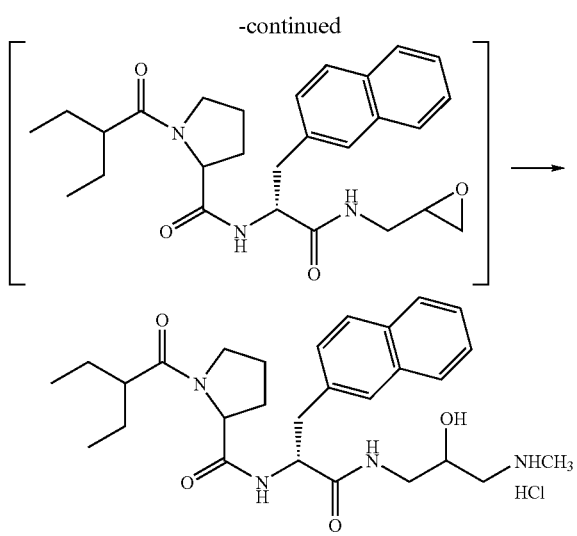

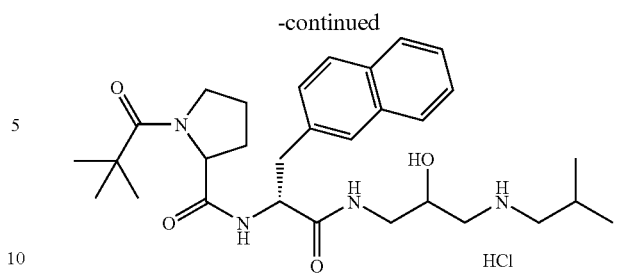

To dichloromethane solution (4 ml) of N-(2-propenyl)-2 (R)-[1-(2-ethylbutyryl) pyrrolidine-2(S)-carbonylamino]-3-naphthalene-2-yl-propionamide 200 mg (0.44 mmol) under cooling on ice-water, solution of metachloroperbenzoic acid 142 mg/dichlorometane 2 ml was added dropwise and stirred at room temperature overnight. The reaction mixture was washed with saturated sodium bicarbonate, water sequentially and dried over anhydrous sodium sulfate. Dichloromethane was removed by evapoaration.

To MeOH solution (3 ml) of above residue, 40% metanol solution of methylamine 300 mg was added and stirring was continued at room temperature overnight. Solvent was removed by evaporation. Further purification by silica gel chromatography gave a desired free product as an oil.

To ethylacetate solution (0.5 ml) of the above oil under cooling on ice-water, 4N—HCl/ethylacetate (0.5 ml) was added, and stirring was continued for 10 min. Evaporation of the solvent gave desired product (24.1 mg) as a white powder. NMR, FAB-MS spectra were consistent with the desired title product.

$^1$H-NMR (270 MHz, DMSO-$d_6$)δ: 0.84 (6H, m), 1.30–1.80 (6H, m), 1.92 (2H, m), 2.34 (1H, m), 2.55 (3H, s), 2.80 (2H, m), 3.00–3.70 (6H, m), 3.97 (1H, m), 4.25 (1H, m), 4.88 (1H, m), 7.42 (4H, m), 7.69 (1H, s), 7.76 (4H, m).

FAB-MS: m/z 497 (M+H)$^+$

Compounds of examples 31, 124, 126, 134, 135, 141, 169, were synthesized by using similar method of example 35.

Example 118 (Method V)

N-[3-(2-methylpropylamino)-2-hydroxypropyl]-2 (R)-[1-(2,2-dimethylpropionyl)-pyrrolidine-2(S)-carbonylamino]-3-naphthalen-2-yl-propionamide hydrochloride

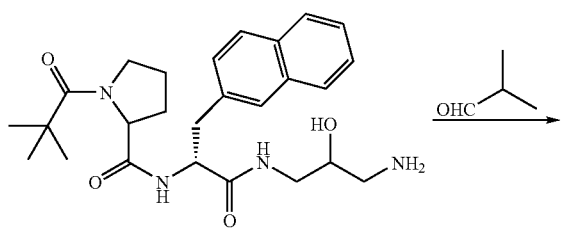

To a mixture of N-(3-amino-2-hydroxypropyl)-2(R)-[1-(2,2-dimethylpropionyl)pyrrolidine-2(S)-carbonylamino]-3-naphthalen-2-yl-propionamide 1.81 g (3.87 mmol) and molecular shieve (3 Å) 1.5 g in methanol, isobutylaldehyde 307 mg (4.25 mmol) and sodium cyano borohydride 243 mg (3.87 mmol) were added under stirring. And then stirring was continued at room temperature overnight. Molecular shieve was removed by filtration. The filtrate was evaporated to dryness. Desired intermediate was purified by column chromatography on silica gel with chloroform and then chloroform:methanol (10:1). Appropriate fractions were collected and then evaporated to dryness.

To methanol solution (10 ml) of the above residue under cooling on ice-water, 4N—HCl/ethylacetate (5 ml) was added and stirring was continued for 10 min. and then solvent was removed in vacuo. The residue was suspended in ethylether. Filtration of the above suspension gave desired product (747 mg) as a powder. NMR, FAB-MS spectra of a powder were consistent with the desired title product.

$^1$H-NMR (270 MHz, DMSO-$d_6$)δ: 0.94 (6H, d), 1.13 (9H, s), 1.33 (1H, m), 1.67 (2H, m), 1.78 (1H, m), 1.99 (1H, m), 2.72 (3H, m), 2.98 (2H, m), 3.17 (1H, m), 3.23–3.60 (4H, m), 3.94 (1H, m), 4.28 (1H, m), 4.55 (1H, m), 5.68 (1H, br), 7.45 (3H, m), 7.70 (1H, s), 7.82 (3H, m), 8.17 (1H, t), 8.32 (1H, m), 8.47 (2H, br).

FAB-MS: m/z 525 (M+H)$^+$

Compounds of examples 119~123, 125, 127~131, 136~140, 143~153, 156, 157, 160, 161, 166~168, 170~190, 194~203, 205, 207, 210 were synthesized by using similar method of example 118.

Test Example

Compounds of Formula I were evaluated in vitro for their efficacy and potency to release growth hormone in primary rat anterior pituitary cells. Preparation of rat primary anterior pituitary cells were be essentially same as described previously (Chen et. al., Endocrinology, 1989, 124, 2791–2798 and Chen et al., Endocrinology, 1991, 129, 3337–3342). Briefly, Rats were killed by decapitation. The pituitary was quickly removed. The anterior pituitaries were digested with 0.2% collagenase, 0.2% hyaluronidase and 200 U/ml Dnase 1 in Hank's balanced salt solution. The cells were resuspended in Dulbecco's Modified Eagle's medium containing 7.5% horse serum, 5.0% fetal calf serum, 1% nonessential amino acids, 100 U/ml penicillin and 100 μg/ml streptomycin and adjusted to 1.0×10$^5$ cells/ml. 0.5 ml of this suspension was placed in each well of 48-well trays and left for 3 days before release experiments were performed.

On a day of the experiments, cells were washed twice with the above medium containing 20 mM HEPES, pH7.4. Growth hormone release was initiated by addition of medium containing 20 mM HEPES and test compound. Incubation was carried out 25 for 15 minutes at 37° C. After incubation growth hormone release into the medium was measured by a standard radioimmunoassay (RIA) procedure.

Compounds of example numbers 1, 3~7, 10~14, 18, 22, 30, 38, 42, 53, 54, 56, 58, 59, 63, 65, 67, 68, 69, 71, 82~84, 86, 87, 88, 92~94, 99~100, 105~109, 111, 115, 118~120, 125, 126, 129, 130, 132~137, 141, 144, 145, 148, 152, 153, 158, 159, 162, 167, 169, 170, 173, 174, 176, 181, 183, 185~187, 191~197, 200~203, 222, 235~239 have shown growth hormone releasing activity below $10^{-8}$ M.

Evaluation of GH-releasing activity by oral administration in rats were carried out as follows.

Male Sprague-Dawley rats (4 weeks old, n=6 per group) were fasted overnight and test compounds (10 mg/kg) were orally administered. Thirty minutes after the administration the rats were decapitated and the trunk blood was collected in a heparin-containing tube. After centrifugation, the plasma was stored at −20° C. before the GH assay by RIA as described above. Plasma GH values were converted into logarithms and the analysis of variance (ANOVA) was performed. The significance of the difference was examined by the LSD method.

Compound of example numbers 1, 3, 4, 6, 14, 17, 29, 30, 38, 42, 54, 58, 63, 65, 71, 86, 87, 88, 93, 100~105, 108, 115, 118~121, 125, 129, 130~132, 136, 141, 143, 145, 153, 154, 162~165, 167, 169, 180~183, 190~197, 199, 201~206, 210 217, 222, 224, 233, 236 and 238 have shown Plasma GH value above 10 ng/ml.

| Ex. No. | Structure | Methods | $^1$H-NMR($\delta$ ppm): | FAB-MS (M+H)$^+$ |
|---|---|---|---|---|
| 2 | 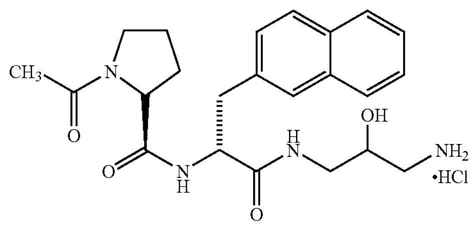 | I | 1.48(2H, m), 1.69(1H, m), 1.89(1H, m), 1.96(3H, s), 2.64(1H, m), 2.88(1H, m), 2.99(1H, m), 3.10–3.35 (4H, m), 3.43(1H, t), 3.77 (1H, m), 4.20(1H, m), 4.50 (1H, m), 7.45(3H, m), 7.71(1H, s), 7.75–8.00(6H, m), 8.37(1H, m), 8.50(1H, m) | 427 |
| 3 | 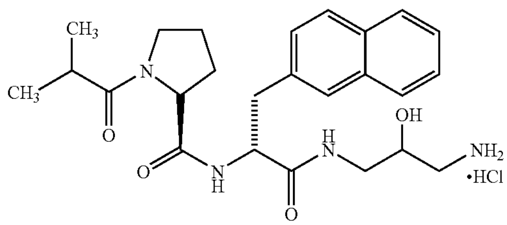 | I | 0.98(6H, m), 1.35–2.00(1H, m), 2.66(2H, m), 2.75–3.05 (2H, m), 3.10–3.40(4H, m), 4.21(1H, m), 4.51(1H, m), 7.46(3H, m), 7.70(1H, s), 7.75–8.05(6H, m), 8.14(1H, m), 8.41(1H, m) | 455 |
| 4 | 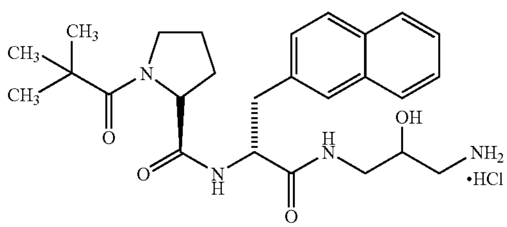 | I | 1.13(9H, m), 1.32(1H, m), 1.55–1.85(3H, m), 2.66(1H, m), 2.80–3.05(2H, m), 3.10–3.70(5H, m), 3.81(1H, m), 4.28(1H, bs), 4.52(1H, t), 5.59(1H, bs), 7.45(3H, m), 7.70(1H, s), 7.75–8.05 (6H, m), 8.15(1H, m), 8.38(1H, m) | 469 |
| 5 | 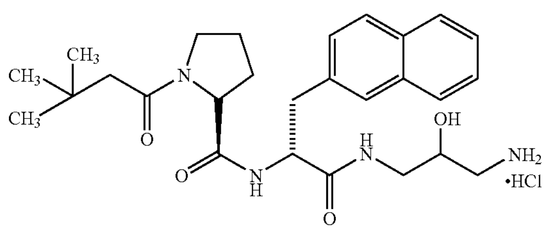 | I | 0.98(9H, s), 1.38–2.28(6H, m), 2.58–3.50(8H, m) 3.77–3.88(1H, m), 4.23(1H, t), 4.48–4.58(1H, m) 5.65(1H, bs), 7.39–7.50(3H, m), 7.73–7.96(6H, m) 8.19(1H, d), 8.56(1H, t) | 483 |
| 6 | 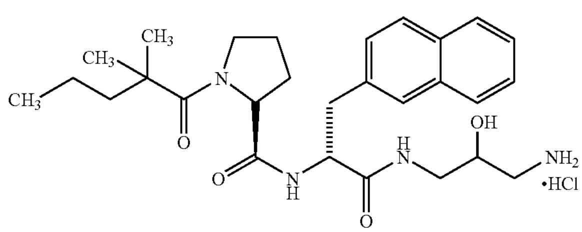 | I | 0.82(3H, t), 1.09(6H, s), 1.10–1.90(6H, m), 2.40–3.70(10H, m) 3.78(1H, m), 4.26(1H, m), 4.53(1H, m), 5.58(1H, m), 7.45(3H, m), 7.69(1H, s), 7.75–8.00(6H, m) | 497 |

-continued

| Ex. No. | Structure | Methods | $^1$H-NMR($\delta$ ppm): | FAB-MS (M+H)$^+$ |
|---|---|---|---|---|
| 7 | 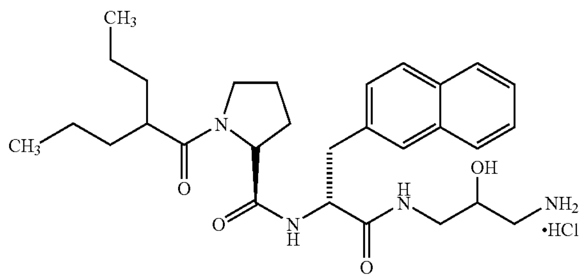 | I | 0.83(6H, t), 1.00–1.55(9H, m), 1.65(1H, m), 1.85(1H, m), 2.67(1H, m), 2.75–3.65 (7H, m), 3.80(1H, m) 4.26(1H, m), 4.54(1H, m) 7.45(3H, m), 7.70(1H, s), 7.75–8.05(6H, m), 8.17(1H, m), 8.45(1H, m) | 511 |
| 8 | 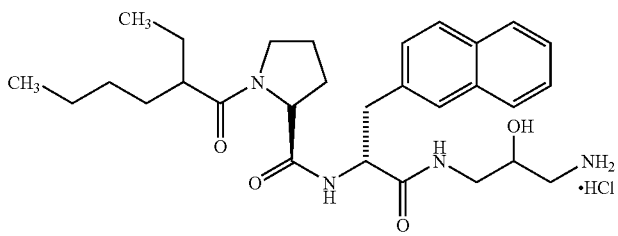 | I | 0.81(6H, m), 1.05–1.60(9H, m), 1.67(2H, m), 1.85(1H, m), 2.45(1H, m), 2.66(1H, m), 2.93(2H, m), 3.00–3.60 (5H, m), 3.79(1H, m), 4.26(1H, m), 4.54(1H, m), 5.66(1H, bs), 7.46(3H, m), 7.70(1H, s), 7.75–8.05(6H, m), 8.16(1H, m), 8.44(1H, m) | 511 |
| 9 | 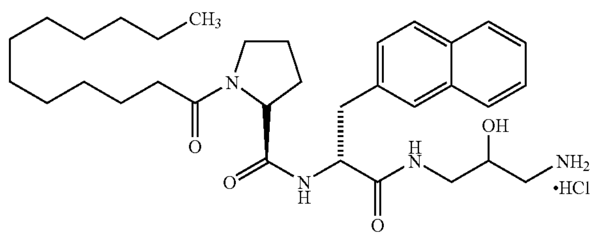 | I | 0.85(3H, t), 1.23(14H, m), 1.45(4H, m), 1.67(2H, m), 1.75–2.05(2H, m), 2.22(2H, t), 2.64(1H, m), 2.80–3.60 (6H, m), 3.78(1H, m), 4.22(1H, m), 4.49(1H, m) 5.62(1H, bs), 7.46(3H, m), 7.70(1H, s), 7.75–8.05(6H, m), 8.14(1H, m), 8.40(1H, m) | 567 |
| 10 | 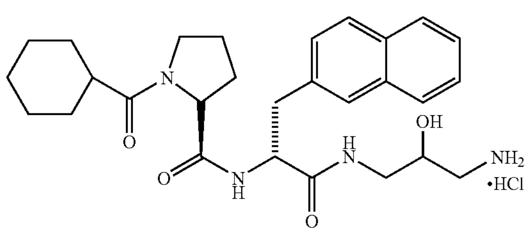 | I | 0.95–2.20(14H, m), 2.37(1H, bs), 2.65(1H, m), 2.89(1H, m), 2.98(1H, m), 3.05–3.90(6H, m), 4.20(1H, m) 4.50(1H, m), 7.45(3H, m), 7.69(1H, s), 7.75–8.05(6H, m), 8.13(1H, m), 8.37(1H, m) | 495 |
| 11 | 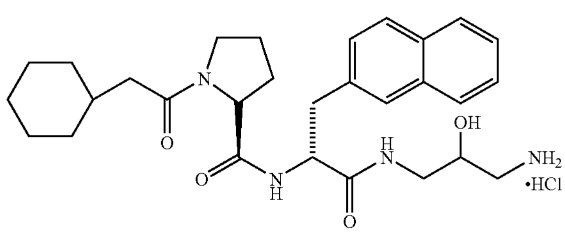 | I | 0.78–2.19(18H, m), 2.57–3.48 (7H, m), 3.72–3.89(1H, m), 4.19–4.29(1H, m), 4.48–4.58 (1H, m), 7.38–7.53(3H, m), 7.70–8.00(6H, m), 8.20(1H, bs), 8.47(1H, t) | 509 |

-continued

| Ex. No. | Structure | Methods | $^1$H-NMR($\delta$ ppm): | FAB-MS (M+H)$^+$ |
|---|---|---|---|---|
| 12 | 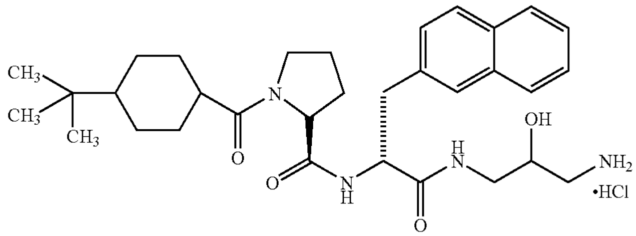 | I | 0.81(9H, m), 0.90–2.00(13H, m), 2.30(1H, m), 2.55–3.70 (8H, m), 4.20(1H, m), 4.50 (1H, m), 7.45(3H, m), 7.70 (1H, s), 7.75–8.00(6H, m), 8.36(2H, m) | 551 |
| 13 | 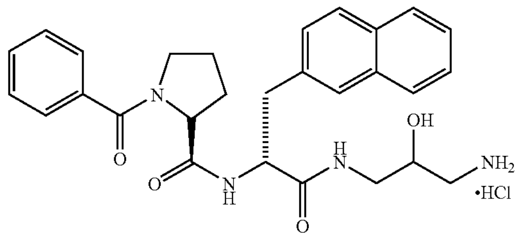 | I | 1.44(1H, m), 1.63(2H, m), 2.00(1H, m), 2.65(1H, m), 2.89(1H, m), 3.03(1H, m), 3.10–3.60(5H, m), 3.80(1H, m), 4.42(1H, m), 4.58(1H, m), 7.45(3H, m), 7.65–8.05 (7H, m), 8.20(1H, m), 8.54(1H, d) | 489 |
| 14 | 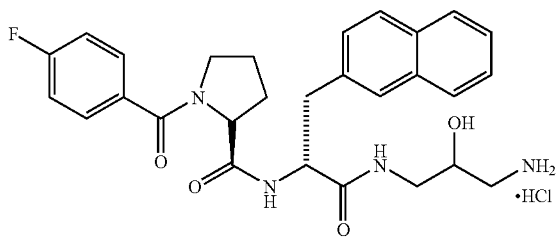 | I | 1.38–2.04(4H, m), 2.59–3.49 (8H, m), 3.75–3.89(1H, m), 4.41(1H, t), 4.51–4.651H, m), 5.62(1H, bs) 7.20–7.89(11H, m)7.95(2H, bs), 8.23(1H, t), 8.55(1H, d) | 507 |
| 15 | 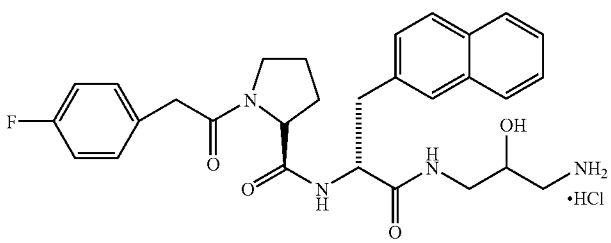 | I | 1.37–1.96(4H, m), 2.55–3.50 (8H, m), 3.62(2H, s) 3.70–3.81(1H, m), 4.22–4.29 (1H, m), 4.45–4.60(1H, m), 7.00–7.51(7H, m), 7.70–7.99 (6H, m), 8.17(1H, bt), 8.48–8.52(1H, m) | 521 |
| 16 | 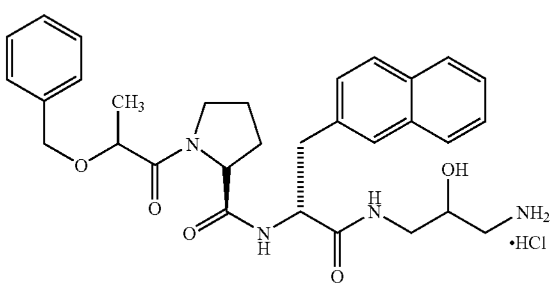 | I | 1.22(3H, d), 1.30–1.95(4H, m), 2.55–3.60(9H, m), 3.77 (1H, m), 4.15–4.80(4H, m), 7.32(5H, m), 7.46(3H, m), 7.70(1H, s), 7.75–8.00 (6H, m), 8.14(1H, m) 8.48(1H, m) | 547 |
| 17 | 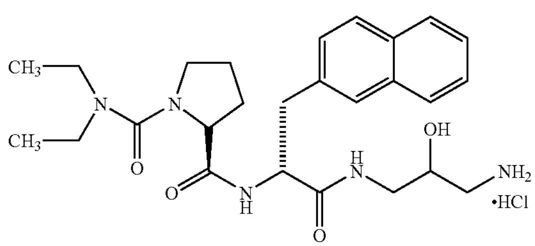 | I | 1.06(6H, t), 1.30–2.00(4H, m), 2.40–3.50(12H, m) 3.70–3.90(1H, m), 4.10–4.70(4H, m), 7.30–7.55(3H, m), 7.60–8.30(7H, m), | 484 |

-continued

| Ex. No. | Structure | Methods | $^1$H-NMR(δ ppm): | FAB-MS (M+H)$^+$ |
|---|---|---|---|---|
| 18 | 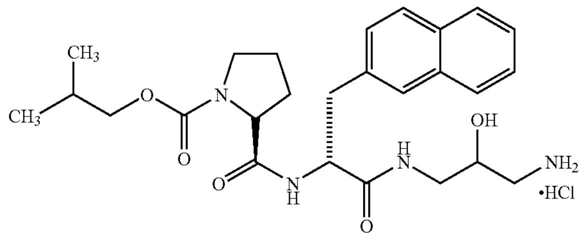 | I | 0.67(3H, m), 0.87(3H, d), 1.30–1.60(4H, m), 1.85(2H, m), 2.65(1H, m), 2.75–3.05 (2H, m), 3.10–3.45(4H, m), 3.49(1H, m), 3.74(2H, m), 4.13(1H, m), 4.65(1H, m), 5.60(1H, bs), 7.46(3H, m), 7.70(1H, s), 77.75–8.00(5H, m), 8.18(1H, m), 8.32(1H, m) | 485 |
| 19 | 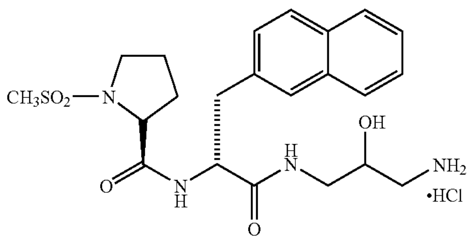 | I | 1.53–2.08(4H, m), 2.58–3.30 (11H, m), 3.70–3.83(1H, m), 4.18–4.21(1H, m), 4.54–4.68 (1H, m), 5.63(1H, bs), 7.38–7.48(3H, m), 7.70–7.85 (4H, m), 7.95(2H, bs), 8.18 (1H, d), 8.23(1H, t) | 463 |
| 21 | 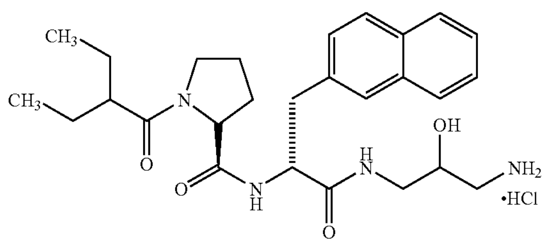 | II | 0.79(6H, t), 1.30–1.55(5H, m), 1.66(2H, m), 1.85(1H, m), 2.37(1H, m), 2.68(1H, m), 2.96(2H, m), 3.05–3.55 (5H, m), 3.77(1H, m), 4.27 (1H, m), 4.53(1H, m) 4.70(1H, bm), 7.46(3H, m), 7.70(1H, s), 7.80–8.00(5H, m), 8.17(1H, m), 8.40(1H, bs), 8.54(1H, m) | 483 |
| 22 | 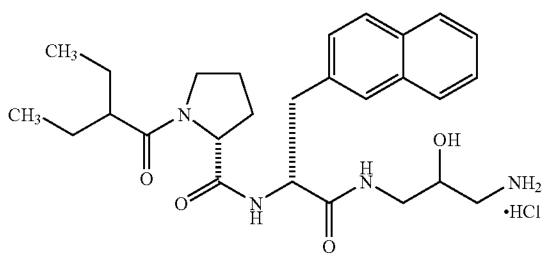 | I | 0.79(6H, t), 1.23–1.98(8H, m), 2.32–3.87(10H, m), 4.25–4.61(2H, m), 7.39–7.57 (3H, m), 7.70–8.17(7H, m), 8.40–8.60(1H, m) | 483 |
| 23 | 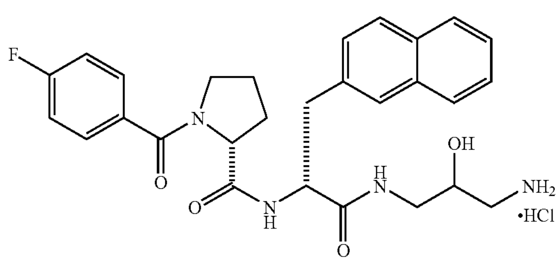 | I | 1.42–2.08(4H, m), 2.58–3.80 (9H, m), 4.37–4.48(1H, m), 4.51–4.65(1H, m), 5.56(1H, bs), 7.22–7.52(5H, m), 7.60–7.93(8H, m), 8.05–8.25 (2H, m) | 507 |
| 24 | 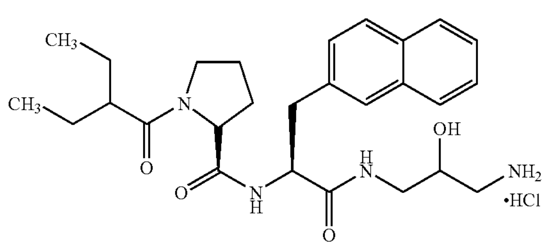 | II | −0.09, 0.64(3H, t), 0.79(3H, t), 0.85–1.20(1H, m), 1.40 (3H, m), 1.79(4H, m), 2.25–2.70(2H, m), 2.70–3.00 (2H, m), 3.00–3.90(6H, m), 4.31(1H, m), 4.40–4.65(1H, m), 7.48(3H, m), 7.72(1H, s), 7.75–8.15(6H, m), 8.37(1H, b), 8.54(1H, d) | 483 |

-continued

| Ex. No. | Structure | Methods | ¹H-NMR(δ ppm): | FAB-MS (M+H)⁺ |
|---|---|---|---|---|
| 25 | 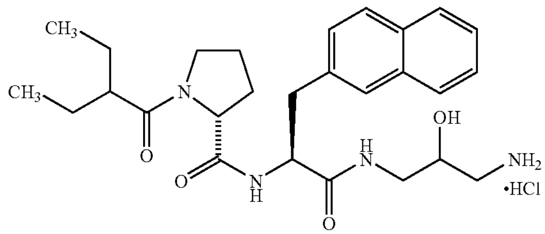 | II | 0.79(6H, t), 1.39(5H, m), 1.66(2H, m), 1.85(1H, m), 2.38(1H, m), 2.64(1H, m), 2.94(2H, m), 3.05–3.90(5H, m), 4.27(1H, m), 4.53(1H, m), 7.45(3H, m), 7.70(1H, s), 7.75–8.00(6H, m), 8.17(1H, m), 8.51(1H, m) | 483 |
| 26 | 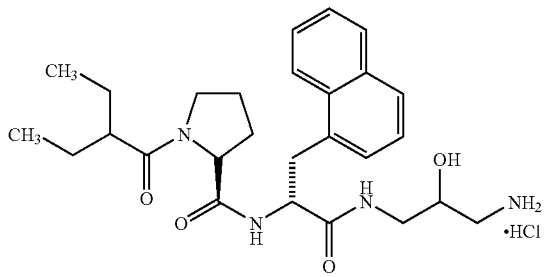 | II | 0.80(6H, m), 1.30–1.60(5H, m), 1.70–1.90(3H, m), 2.40(1H, m), 2.65(1H, m), 2.80–3.00(1H, m), 3.05–3.30 (3H, m), 3.52(2H, m), 3.80(2H, m), 4.20(1H, bs) 4.26(1H, m), 4.50(1H, m), 7.42(2H, m), 7.55(2H, m), 7.81(1H, m), 7.94(3H, m), 8.17(2H, m), 8.40(1H, m), 8.70(1H, m) | 483 |
| 27 | 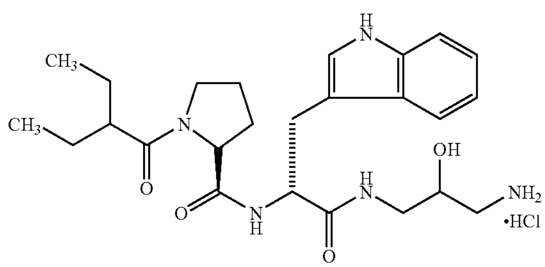 | I | 0.81(6H, t), 1.30–1.95(8H, m), 2.35–2.70(2H, m), 2.70–3.00(2H, m), 3.05–3.45 (3H, m), 3.50–3.60(2H, m), 3.65–3.85(1H, m), 4.25–4.35 (1H, m), 4.35–4.50(1H, m), 5.60–5.75(1H, m), 6.90–7.65 (5H, m), 7.85(2H, bs), 8.05–8.15(1H, m), 8.40–8.50 (1H, m), 10.82(1H, bs) | 472 |
| 28 | 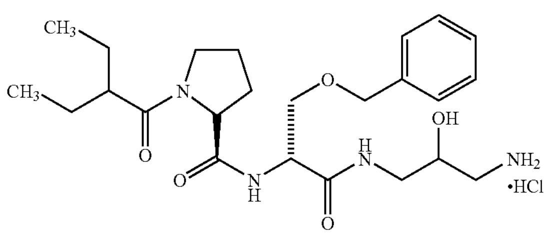 | I | 0.82(6H, t), 1.35–1.60(4H, m), 1.80–1.95(2H, m), 1.95–2.20(2H, m), 2.40–2.55 (1H, m), 2.55–2.70(1H, m), 2.80–3.00(1H, m), 3.00–3.15 (1H, m), 3.15–3.30(1H, m), 3.30–3.45(1H, m), 3.55–3.85 (5H, m), 4.35–4.45(2H, m), 4.50(2H, s), 5.65, 5.70(1H, dd), 7.25–7.40(5H, m), 7.90(3H, bs), 8.05–8.20(1H, m), 8.45–8.55(1H, m) | 463 |
| 29 | 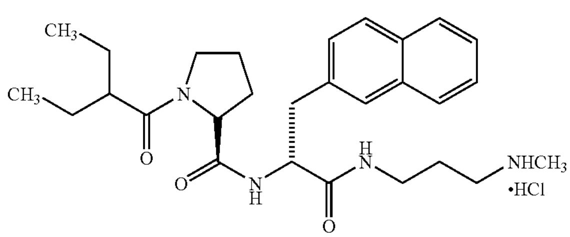 | II | 0.79(6H, t), 1.40(5H, m), 1.74(5H, m), 2.44(2H, m), 2.65–3.05(2H, m), 3.10–3.60 (5H, m), 4.27(1H, m), 4.49(1H, m), 7.46(3H, m), 7.70(1H, s), 7.82(3H, m), 8.18(1H, t), 8.53(1H, d), 8.70(3H, bs) | 481 |
| 31 | 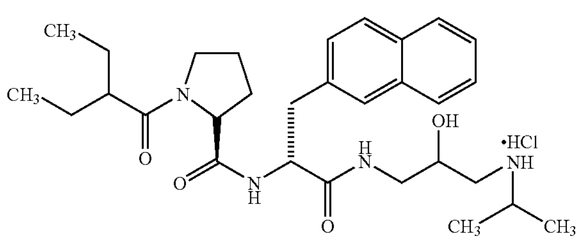 | IV | 0.79(6H, t), 1.22(6H, m), 1.42(6H, m), 1.67(2H, m), 1.87(1H, m), 2.39(1H, m), 2.75(1H, m), 2.85–3.60(7H, m), 3.89(1H, m), 4.28(1H, m), 4.55(1H, m), 5.75(1H, bs), 7.47(3H, m), 7.71(1H, s), 7.83(3H, m) 8.19(1H, m), 8.49(1H, m) | 485 |

-continued

| Ex. No. | Structure | Methods | $^1$H-NMR($\delta$ ppm): | FAB-MS (M+H)$^+$ |
|---|---|---|---|---|
| 32 | 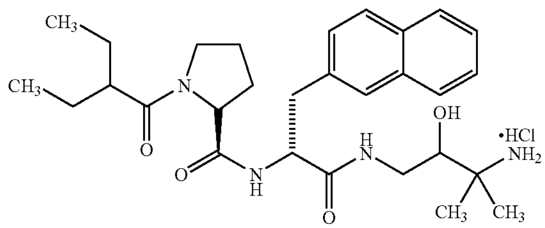 | I | 0.80(6H, t), 1.15–1.30(6H, m), 1.30–1.55(6H, m), 1.55–1.90(3H, m), 2.30–2.50 (1H, m), 2.60–2.70(1H, m), 2.85–3.15(2H, m), 3.20–3.65 (4H, m), 4.20–4.30(1H, m), 4.40–4.65(1H, m), 7.35–7.65 (3H, m), 7.70(1H, s), 7.75–7.95(6H, m), 7.95–8.15(1H, m), 8.30–8.55(2H, m) | 511 |
| 33 | 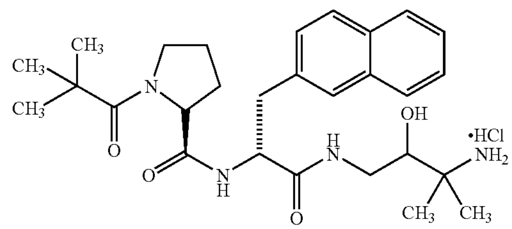 | I | 1.05–1.30(15H, m), 1.55–1.90 (4H, m), 2.65(1H, bs) 2.85–3.35(4H, m), 3.50–3.65 (2H, m), 4.25(1H, bs) 4.40–4.60(1H, m), 7.35–7.50 (3H, m), 7.65–7.95(6H, m), 7.95–8.50(4H, m) | 495 |
| 34 | 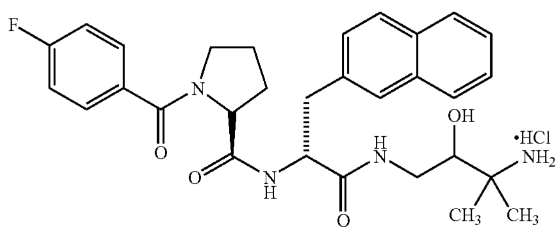 | I | 1.10–1.30(6H, m), 1.67(2H, m), 3.02(3H, m), 4.41(1H, t), 4.60(1H, m), 5.89(1H, bs), 7.26(3H, m), 7.46(3H, m), 7.54–7.96(7H, m), 8.10–8.60(2H, m) | 535 |
| 36 | 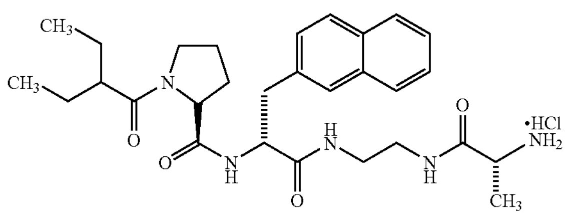 | III | 0.79(6H, m), 1.36(3H, d), 1.43(5H, m), 1.68(2H, m), 1.86(1H, m), 2.39(1H, m) 2.97(1H, m), 3.05–3.90(8H, m), 4.28(1H, m), 4.49(1H, m), 7.46(3H, m), 7.70(1H, s), 7.81(3H, m), 8.18(4H, bs), 8.58(2H, bs) | 524 |
| 37 | 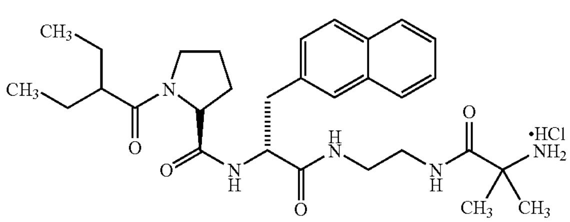 | III | 0.80(6H, m), 1.40(5H, m), 1.47(6H, s), 1.60–2.10(3H, m), 2.38(1H, m), 2.96(1H, m), 3.05–3.90(7H, m) 4.29(1H, t), 4.49(1H, m), 7.46(3H, m), 7.71(1H, s), 7.82(3H, m), 8.12(1H, bs), 8.23(3H, bs), 8.39(1H, bs), 8.57(1H, d) | 538 |
| 38 | 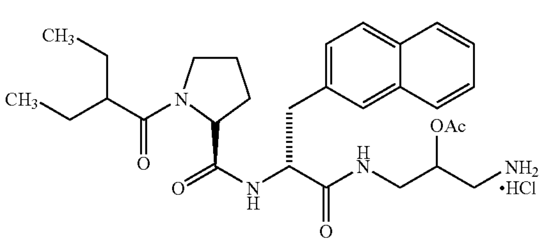 | II | 0.79(6H, m), 1.38(5H, m), 1.66(2H, m), 1.85(1H, m), 2.05(3H, s), 2.85–3.60(8H, m), 4.27(1H, t), 4.52(1H, m), 4.99(1H, m), 7.47(3H, m), 7.71(1H, s), 7.84(3H, m), 8.11(2H, bs), 8.29(1H, m) | 525 |

-continued

| Ex. No. | Structure | Methods | $^1$H-NMR($\delta$ ppm): | FAB-MS $(M+H)^+$ |
|---|---|---|---|---|
| 39 | (structure) | II | 0.83(6H, t), 1.50(4H, m), 1.75–2.20(4H, m), 2.01(2H, bs), 2.31(3H, s), 2.34(1H, m), 2.67(2H, t), 3.10–3.75(6H, m), 4.14(1H, t) 4.83, (1H, m), 6.67(1H, d), 7.45(3H, m), 7.66(1H, s), 7.78(3H, m) in CDCl$_3$ | 467 |
| 40 | (structure) | II | 0.80(6H, m), 1.40(4H, m), 1.60–2.00(4H, m), 2.45(1H, m), 2.80–3.05(2H, m), 3.10–3.80(6H, m), 4.27(1H, t), 4.52(1H, m), 7.45(3H, m), 7.70(1H, s), 7.83(3H, m), 8.01(3H, bs), 8.19(1H, t), 8.59(1H, d) | 453 |
| 41 | (structure) | I | 0.79(6H, m), 1.20–2.00(10H, m), 2.45(1H, m), 2.60–4.00 (8H, m), 4.27(1H, m), 4.52(1H, m), 7.47(3H, m), 7.70(1H, s), 7.75–8.00 (6H, m), 8.16(1H, t), 8.52(1H, d) | 467 |
| 42 | (structure) | I | 1.15–1.70(4H, m), 2.40–3.58 (10H, m), 3.72–3.85(1H, m), 4.00–4.15(1H, m), 4.54–4.68 (1H, m), 7.20–7.57(7H, m), 7.70–8.02(6H, m), 8.22(1H, d), 8.30(1H, t) | 521 |
| 43 | (structure) | I | 1.25–1.70(4H, m), 2.05–2.20 (2H, m), 2.61(1H, m) 2.70–2.95(2H, m), 3.03–3.30 (3H, m), 3.30–3.50(3H, m), 3.73(1H, bs), 4.52(1H, m), 5.58(1H, bs), 7.40(1H, d), 7.48(2H, m), 7.64(6H, m), 7.75–7.95(5H, m), 8.13(1H, d), 8.25(1H, t) | 539 |

-continued

| Ex. No. | Structure | Methods | ¹H-NMR(δ ppm): | FAB-MS (M+H)⁺ |
|---|---|---|---|---|
| 44 | 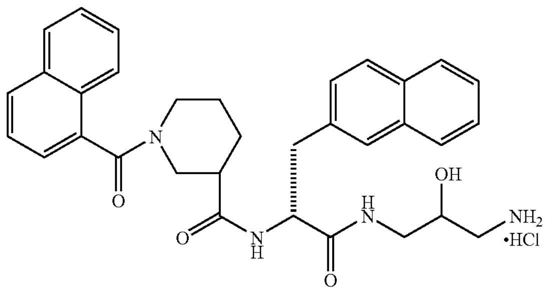 | I | 1.19–1.96(4H, m), 2.58–3.30 (10H, m), 3.70–3.90(1H, m), 4.40–4.73(2H, m), 7.29–8.05 (16H, m), 8.35–8.49(2H, m) | 553 |
| 45 | 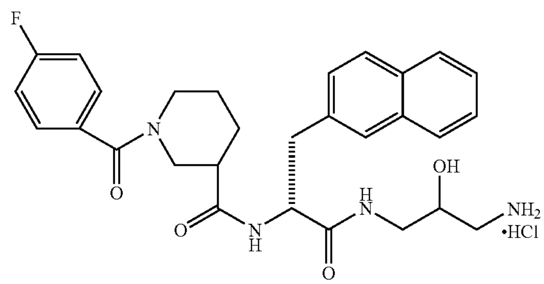 | I | 1.20–1.90(4H, m), 2.27–3.25 (10H, m), 3.70–3.85(1H, m), 4.15–4.42(1H, m), 4.50–4.67 (1H, m), 5.61(1H, s), 7.20–7.54(7H, m), 7.69–7.95 (6H, m), 8.20–8.43(2H, m) | 521 |
| 46 | 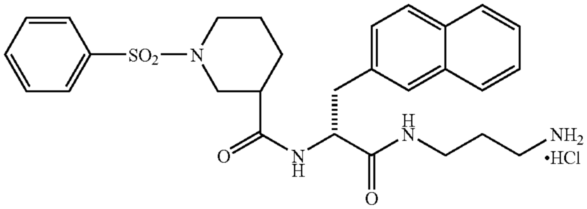 | I | 0.80–1.80(6H, m), 2.03(1H, m), 2.73(4H, m), 2.92(1H, m), 3.15(3H, m), 3.57(2H, t), 4.52(1H, m), 7.35–8.00(14H, m), 8.27(1H, m), 8.40(1H, t) | 523 |
| 47 | 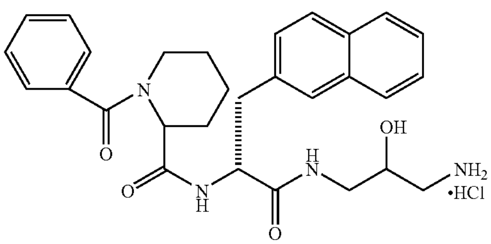 | I | 0.90–2.20(10H, m), 2.70(1H, m), 2.80–3.70(5H, m) 3.80(1H, m), 4.73(1H, m), 5.07(1H, m), 7.10–7.50(8H, m), 7.60–8.05(7H, m), 8.15–8.50(2H, m) | 503 |
| 48 | 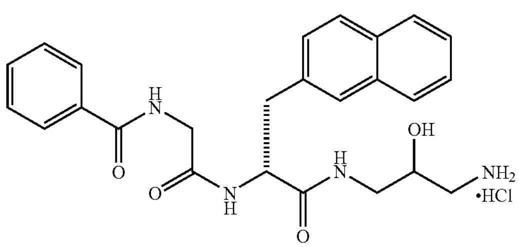 | I | 2.90–3.55(6H, m), 3.60–4.05 (3H, m), 4.50–4.70(1H, m), 5.58(1H, d), 7.30–7.60(6H, m), 7.70–7.95(6H, m), 8.20–8.40(2H, m), 8.70–8.85(1H, m) | 449 |
| 49 | 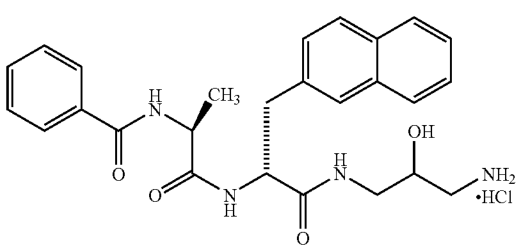 | I | 1.00–1.40(3H, m), 2.50–3.50 (7H, m), 3.70–3.90(1H, m), 4.30–4.85(2.5H, m), 5.20–5.70(1.5H, m), 7.30–8.80(15H, m) | 463 |

-continued

| Ex. No. | Structure | Methods | $^1$H-NMR($\delta$ ppm): | FAB-MS (M+H)$^+$ |
|---|---|---|---|---|
| 50 | 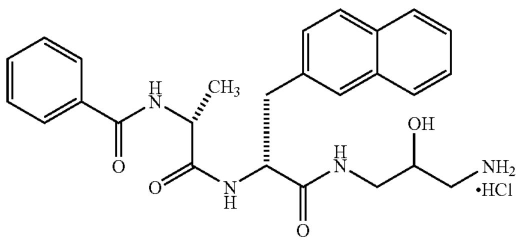 | I | 1.11(1.5H, d), 1.25(1.5H, d), 2.60–3.60(7H, m) 3.70–3.95 (1H, m), 4.30–4.70(2H, m), 7.30–8.60(17H, m) | 463 |
| 51 | 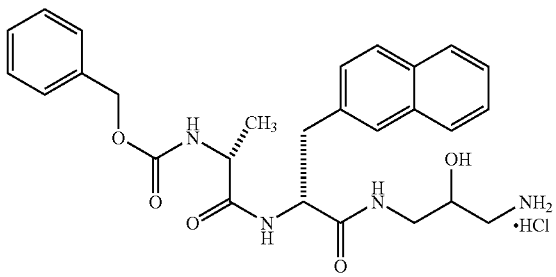 | I | 1.10(3H, d), 2.50–2.70(2H, m), 2.70–2.95(2H, m) 2.95–3.30(3H, m), 3.65, 3.85(1H, m), 3.90–4.10(1H, m), 4.99(2H, q), 5.58(1H, t), 7.22–7.55(8H, m) 7.60–7.95(6H, m), 8.06(1H, d), 8.28(1H, t) | 493 |
| 52 | 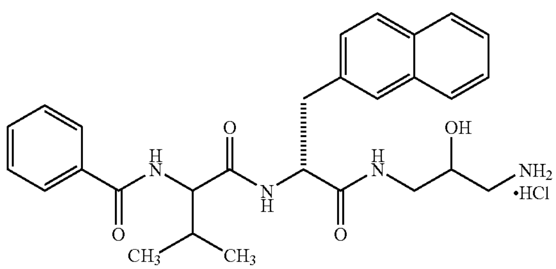 | I | 0.40–0.90(7H, m), 1.80–3.50 (6H, m), 3.60–3.90(1H, m), 4.10–4.30(1H, m), 4.50–4.75 (1H, m), 5.50–5.80(1H, m), 7.30–8.80(17H, m) | 491 |
| 53 | 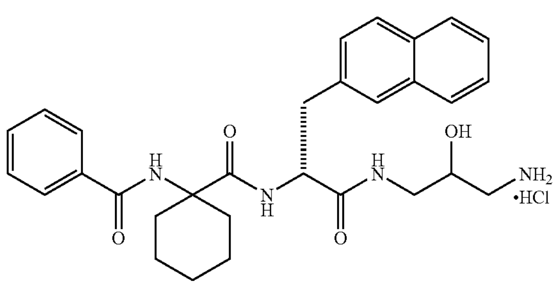 | I | 1.05–2.10(10H, m), 2.50–3.90 (6H, m), 4.10–4.80(3H, m), 7.30–8.40(17H, m) | 517 |
| 54 | 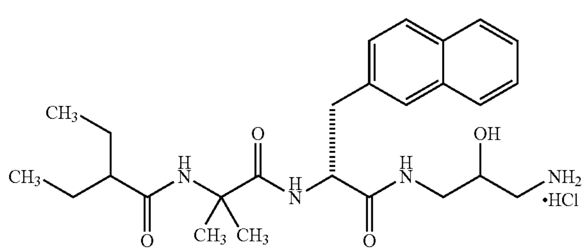 | I | 0.75(6H, m), 1.00–1.50(10H, m), 2.02(1H, m)2.63(1H, m), 2.89(1H, m), 2.97–3.50(4H, m), 3.77(1H, m), 4.47(1H, m), 7.37(1H, d), 7.46(2H, m), 7.61(1H, d), 7.67(1H, s), 7.75–8.00(6H, m), 8.26(1H, s) | 471 |

-continued

| Ex. No. | Structure | Methods | ¹H-NMR(δ ppm): | FAB-MS (M+H)⁺ |
|---|---|---|---|---|
| 55 | 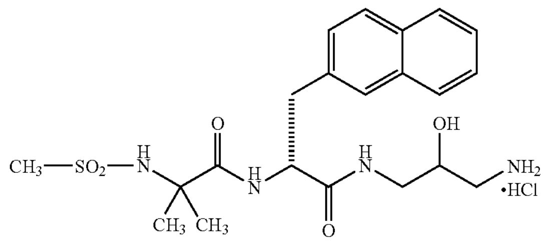 | I | 1.15(3H, s), 1.26(3H, s), 2.63(1H, m), 2.88(1H, m) 3.05–3.35(4H, m), 3.76(1H, m), 4.62(1H, m), 7.39(1H, s), 7.46(3H, m), 7.72(1H, s), 7.75–8.00(6H, m) 8.16(1H, t) | 451 |
| 56 | 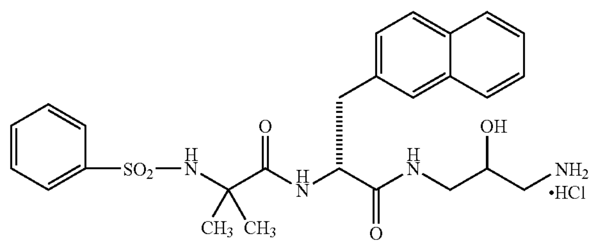 | I | 1.02(6H, s), 2.40–3.50 (7H, m), 3.70–3.90(1H, m) 4.50–4.70(1H, m), 5.50–5.70 (1H, m), 7.30–8.40(16H, m) | 513 |
| 57 | 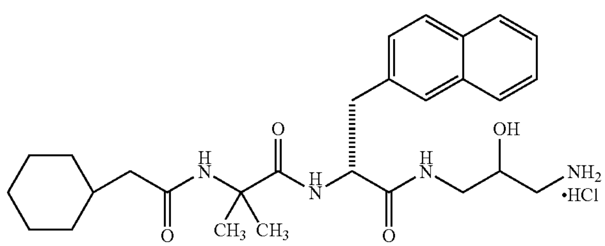 | I | 0.85(2H, m), 1.07(3H, s), 1.15(3H, s), 1.00–1.30(3H, m), 1.60(6H, m), 1.99(2H, d), 2.64(1H, m), 2.90(1H, m), 3.14(3H, m), 3.37(1H, m), 3.79(1H, m), 4.46(1H, m), 7.37(1H, d), 7.46(2H, m), 7.66(1H, s), 7.75–8.00(6H, m), 8.24(1H, s) | 497 |
| 58 | 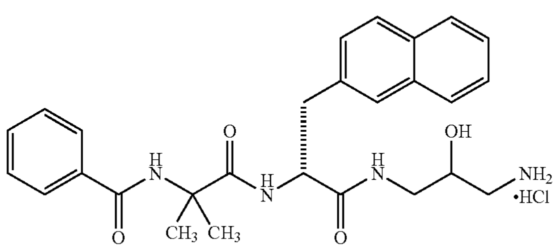 | I | 1.21(3H, s), 1.29(3H, s), 2.68(1H, m), 2.93(1H, m) 3.00–3.40(4H, m), 3.84(1H, m), 4.51(1H, t), 5.60(1H, bs), 7.47(6H, m), 7.65(1H, s), 7.75(2H, m), 7.80–8.10(7H, m), 8.56(1H, d) | 477 |
| 59 | 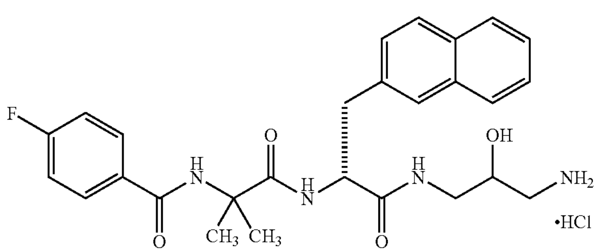 | I | 1.19(3H, d), 1.28(3H, s), 2.50–3.50(7H, m), 3.70–4.00 (1H, m), 4.40–4.70(1H, m), 5.50–5.80(1H, m) 7.20–8.80(15H, m) | 495 |
| 60 | 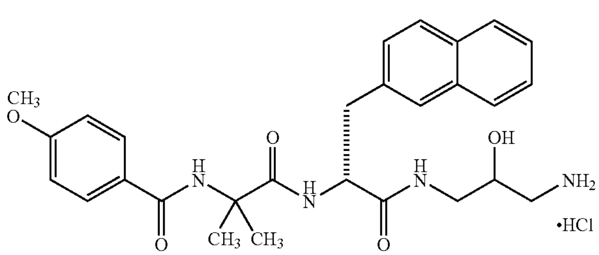 | I | 1.19(3H, d), 1.27(3H, s), 2.40–3.90(6H, m), 2.83(3H, s), 4.05–4.25(1H, m), 4.40–4.60(1H, m), 5.50–5.80 (1H, m), 6.90–7.10(4H, m), 7.30–8.60(11H, m) 8.70–8.95(1H, m) | 507 |

-continued
| Ex. No. | Structure | Methods | $^1$H-NMR($\delta$ ppm): | FAB-MS $(M+H)^+$ |
|---|---|---|---|---|
| 61 | 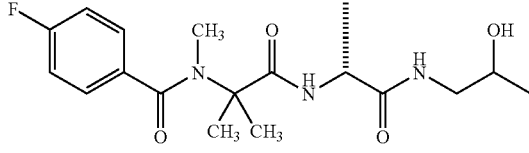 | I | 1.44(6H, s), 2.40–3.50(8H, m), 3.70–3.90(1H, m) 4.05–4.25(1H, m), 5.60–5.80 (1H, m), 7.20–8.10(12H, m), 8.20–8.50(2H, m), 8.80–8.95(1H, m) | 509 |
| 62 | 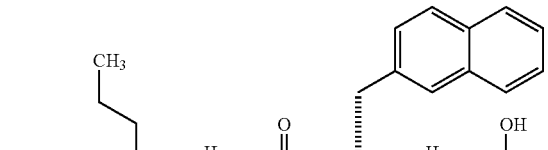 | I | 0.70–0.90(6H, m), 1.00–1.50 (8H, m), 1.14(3H, d) 1.19(3H, d), 2.10–3.50(8H, m), 3.60–3.90(1H, m) 4.35–4.60(1H, m), 5.40–5.80 (1H, m), 7.20–8.50(11H, m) | 499 |
| 63 | 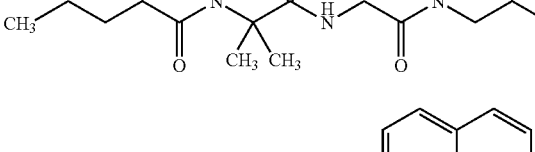 | I | 1.00–1.25(9H, m), 1.32(3H, s), 2.40–3.50(9H, m) 3.70–3.90(1H, m), 4.35–4.60 (1H, m), 5.45–5.70(1H, m), 7.30–8.50(1H, m) | 491 |
| 64 | 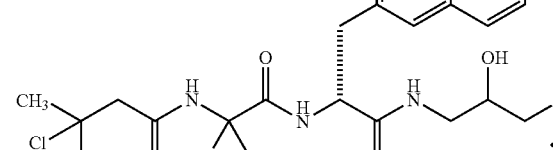 | I | 1.00–1.80(10H, m), 1.07(1.5H, s), 1.09(1.5H, s), 1.15(3H, s), 2.00–4.00(10H, m), 4.50–4.60(1H, m), 7.30–8.20(11H, m) | 483 |
| 65 | 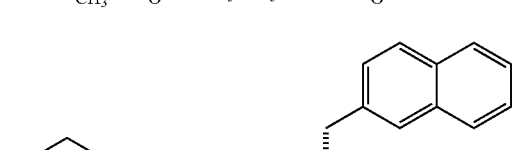 | I | 1.06(1.5H, s), 1.07(1.5H, s), 1.14(3H, s), 2.40–3.60(7H, m), 3.57(2H, s), 3.70–3.85 (1H, m), 4.40–4.60(1H, m), 5.40–5.70(1H, m), 7.10–8.00 (15H, m), 8.58(1H, d) | 491 |
| 66 | 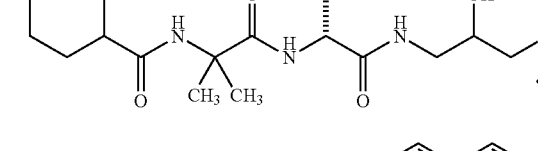 | I | 1.15–1.45(12H, m), 2.40–2.80 (2H, m), 2.95–3.20(2H, m), 3.55–3.65(1H, m), 4.50–4.65 (1H, m), 4.50–4.65(1H, m), 5.65–5.70(1H, bs), 7.35–7.60 (4H, m)7.65–8.00(11H, m), 8.30–8.60(2H, m) | 505 |

| Ex. No. | Structure | Methods | ¹H-NMR(δ ppm): | FAB-MS (M+H)⁺ |
|---|---|---|---|---|
| 67 | 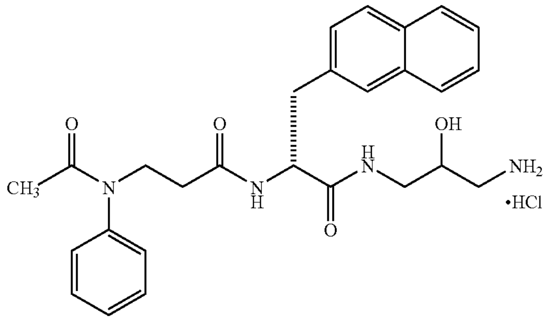 | I | 1.61(3H, s), 2.15–2.40(2H, m), 2.55–2.70(1H, m) 2.70–3.00(2H, m), 3.00–3.30 (3H, m), 3.55–3.85(3H, m), 4.51(1H, m), 5.57(1H, bs), 7.12(2H, d) 7.25–7.55(6H, m), 7.65–8.00(6H, m), 8.15–8.40(2H, m) | 477 |
| 68 | 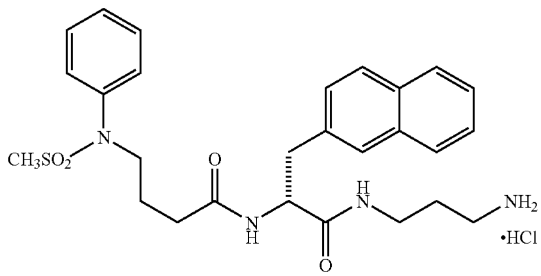 | I | 1.40(2H, m), 1.67(2H, m), 2.09(2H, t), 2.71(2H, m) 2.90(3H, s), 3.12(3H, m), 3.48(2H, m), 4.49(1H, m) 7.25–7.50(8H, m), 7.70(1H, s), 7.75–7.95(5H, m) 8.22(2H, m) | 511 |
| 69 | 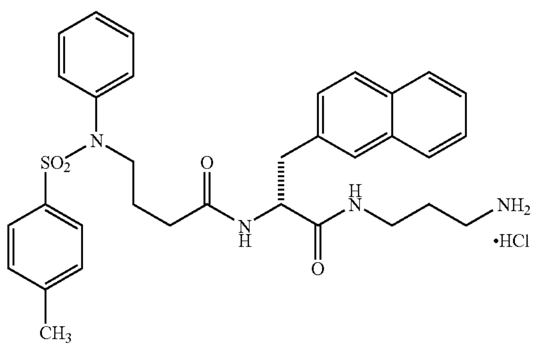 | I | 1.38(2H, m), 1.68(2H, m), 2.10(2H, m), 2.39(3H, s) 2.73(2H, m), 2.89(1H, m), 3.10(3H, m), 4.47(1H, m) 6.96(2H, m), 7.25–7.50 (10H, m), 7.68(1H, s), 7.75–7.95(5H, m), 8.22(2H, m) | 587 |
| 70 | 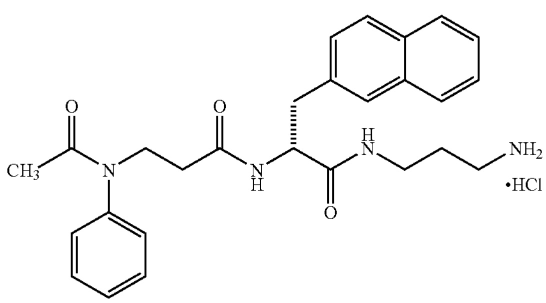 | I | 1.40–1.80(5H, m), 2.15–2.40 (2H, m), 2.60–2.80(3H, m), 2.90(1H, dd), 3.00–3.20(2H, m), 3.67(2H, t 4.47(1H, m), 6.95–7.55(8H, m), 7.60–7.95 (6H, m)8.18(1H, t), 8.32(1H, d) | 461 |
| 71 | 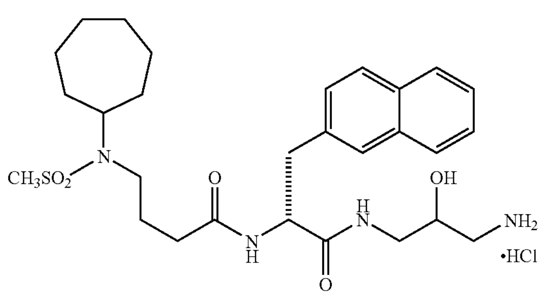 | I | 1.15–1.75(14H, m), 2.04(2H, t), 2.55–3.00(5H, m) 2.75(3H, s), 3.17(3H, m), 3.45(1H, bs), 3.75(1H, bs), 4.59(1H, m), 5.58(1H, bs), 7.46(3H, m), 7.65(1H, (1H, s), 7.80–8.00(5H, m), 8.23(1H, d), 8.30(1H, t) | 547 |

-continued

| Ex. No. | Structure | Methods | ¹H-NMR(δ ppm): | FAB-MS (M+H)⁺ |
|---|---|---|---|---|
| 72 | 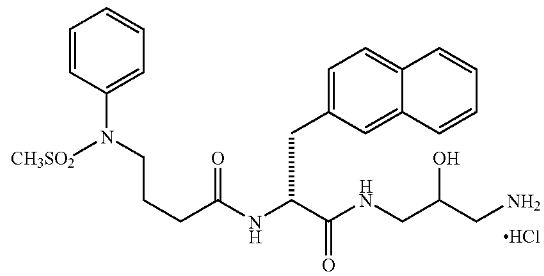 | I | 1.38(2H, t), 2.09(2H, t), 2.62(1H, m), 2.73–2.95(2H, m), 2.89(3H, s), 3.13(3H, m), 3.47(2H, m), 3.72(1H, m), 4.52(1H, m), 5.55(1H, d), 7.25–7.50(8H, m) 7.70(1H, s), 7.74–7.90(5H, m), 8.22(2H, m) | 527 |
| 73 | 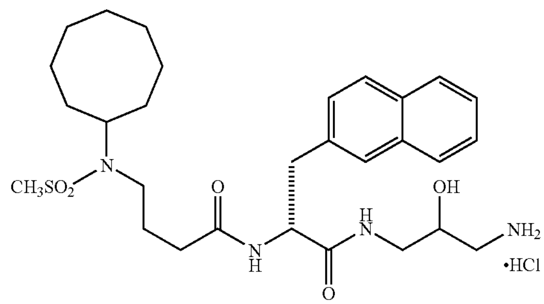 | I | 1.25–1.75(16H, m), 2.04(2H, t), 2.55–2.95(5H, m) 2.74(3H, s), 3.17(3H, m), 3.55–3.85(2H, m), 4.59(1H, m), 7.46(3H, m), 7.75(1H, s), 7.80–7.98(5H, m) 8.23(1H, d), 8.30(1H, t) | 561 |
| 74 | 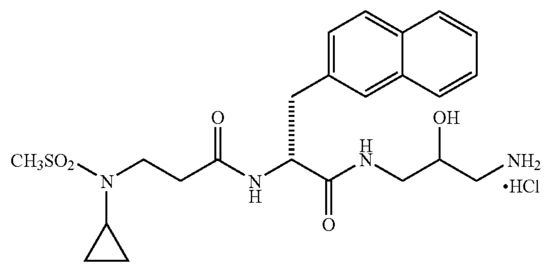 | I | 0.45(2H, m), 0.56(2H, m), 2.14(1H, m), 2.41(1H, t) 2.64(1H, m), 2.75–3.00(2H, m), 2.82(3H, t), 3.05–3.30 (4H, m), 3.41(1H, bs), 3.75 (1H, m), 4.60(1H, m) 5.60(1H, bs), 7.47(3H, m), 7.75(1H, s), 7.80–8.00(5H, m), 8.34(1H, t), 8.42(1H, d) | 477 |
| 75 | 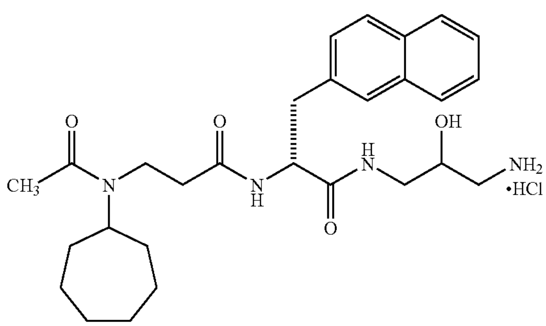 | I | 1.15–1.65(12H, m), 1.89(3H, d), 2.10–2.40(2H, m) 2.55–2.70(1H, m), 2.75–3.30 (7H, m), 3.45–4.00(2H, m), 4.50–4.70(1H, m), 5.10 (1H, bs), 7.40–7.55(3H, m), 7.70–8.00(6H, m), 8.20–8.45 (2H, m) | 497 |
| 76 | 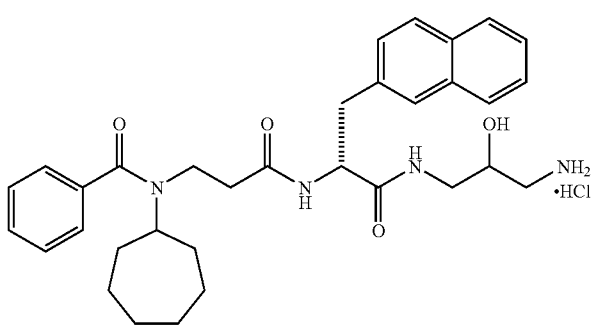 | I | 0.85–1.80(12H, m), 2.15–2.70 (2H, m), 2.75–3.45(7H, m), 3.55–3.95(3H, m), 4.60(1H, m), 5.60(1H, bs), 7.15–7.55 (8H, m), 7.65–8.00(6H, m), 8.20–8.45(2H, m) | 559 |

-continued

| Ex. No. | Structure | Methods | ¹H-NMR(δ ppm): | FAB–MS (M+H)⁺ |
|---|---|---|---|---|
| 77 | 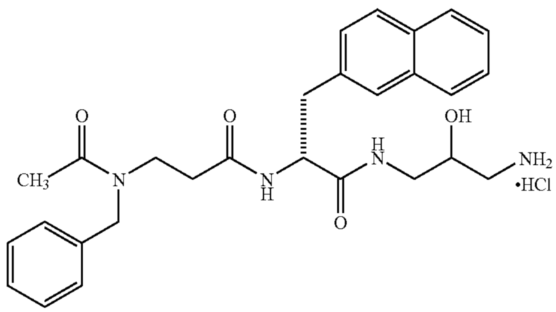 | I | 1.91(3H, d), 2.20–2.45(2H, m), 2.55–2.70(1H, m) 2.75–3.00(2H, m), 3.05–3.30 (4H, m), 3.65–3.80(1H, m), 3.85–4.50(3H, m), 4.50–4.65 (1H, m), 6.95–7.55(8H, m), 7.65–8.00(6H, m), 8.20–8.55 (2H, m) | 491 |
| 78 | 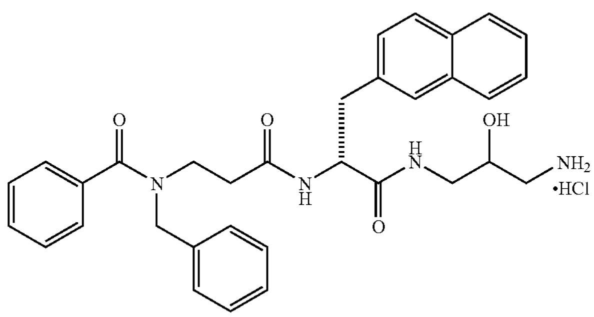 | I | 2.25–2.50(2H, m), 2.55–2.70 (1H, m), 2.75–3.00(2H, m), 3.00–3.85(2H, m), 4.05–4.20 (1H, m), 4.45–4.75(2H, m), 5.55(1H, bs), 6.97(1H, d), 7.20–7.50(12H, m), 7.65–8.00 (6H, m), 8.25–8.55(2H, m) | 553 |
| 79 | 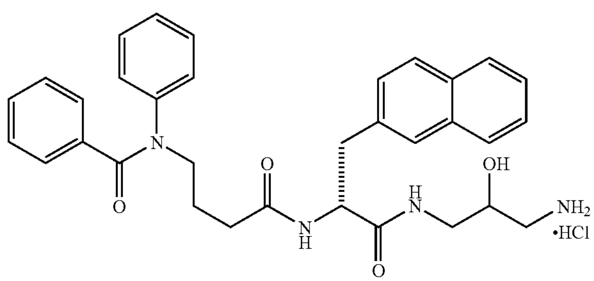 | I | 1.52(2H, m), 2.09(2H, t), 2.63(1H, m), 2.90(2H, m) 3.18(3H, m), 3.57(2H, m), 3.78(1H, m), 4.57(1H, m) 6.92(2H, d), 7.19(8H, m), 7.45(3H, m), 7.60–8.00(7H, m), 8.30(2H, m) | 553 |
| 80 | 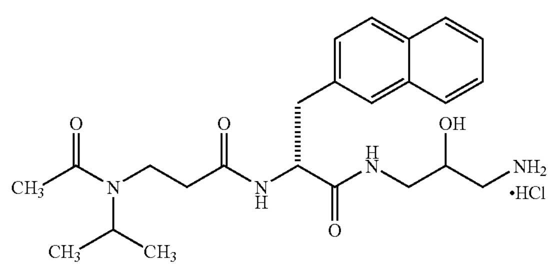 | I | 0.85–1.00(6H, m), 1.90(3H, d), 2.10–2.40(2H, m) 2.55–2.75(1H, m), 2.80–3.30 (7H, m), 3.70–5.30(4H, m), 7.35–7.55(3H, m), 7.65–8.05(6H, m), 8.20–8.45(2H, m) | 443 |
| 81 | 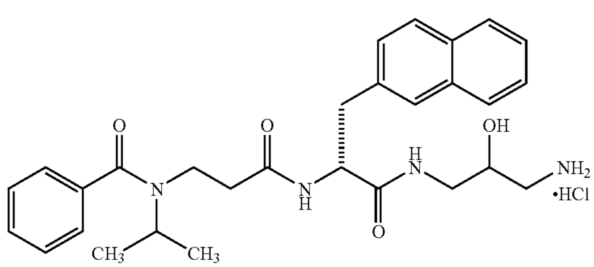 | I | 0.92(6H, s), 2.15–2.45(1H, m), 2.55–2.70(1H, m) 2.80–3.40(7H, m), 3.50–3.90 (3H, m), 4.50–4.70(1H, m), 5.55(1H, bs), 7.24(2H, d), 7.30–7.55(6H, m), 7.60–8.05 (6H, m), 8.20–8.45(2H, m) | 505 |

-continued

| Ex. No. | Structure | Methods | ¹H-NMR(δ ppm): | FAB-MS (M+H)⁺ |
|---|---|---|---|---|
| 82 | 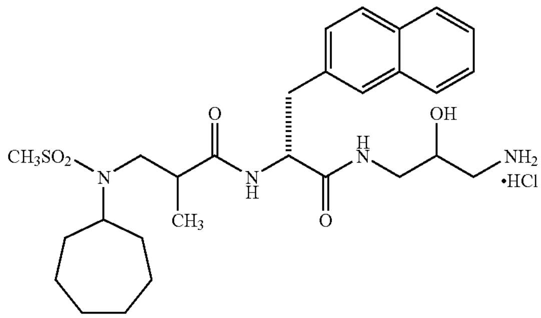 | I | 0.67, 0.89(3H, d), 1.10–1.75 (12H, m), 2.55–3.90(11H, m), 2.84(3H, s), 4.64(1H, m), 5.60(1H, bs) 7.46(3H, m), 7.70–8.00(6H, m), 8.25–8.45(2H, m) | 547 |
| 83 | 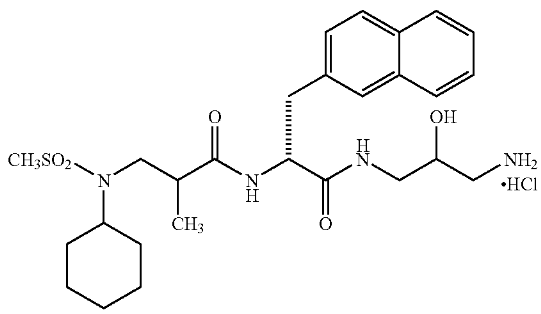 | I | 0.68, 0.88(3H, d), 0.90–1.80 (10H, m), 2.55–3.40(10H, m), 2.86(3H, s), 3.74(1H, m), 4.64(1H, m) 7.46(3H, m), 7.70–8.00(6H, m), 8.25–8.60(2H, m) | 533 |
| 84 | 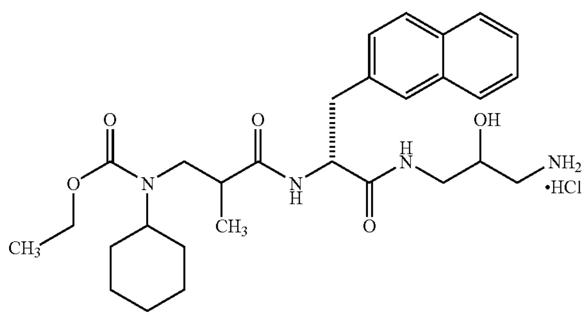 | I | 0.65, 0.87(3H, d), 1.00–1.75 (13H, m), 2.59(2H, m) 2.70–3.60(8H, m), 3.75(1H, bs), 3.97(2H, m), 4.55(1H, m), 7.46(3H, m), 7.65–8.05 (6H, m), 8.31(2H, m) | 527 |
| 85 | 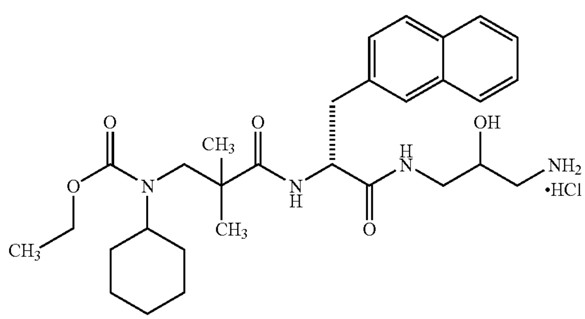 | I | 0.75–1.20(4H, m), 0.89(3H, s), 0.96(3H, s), 1.11(3H, t), 1.25–1.85(6H, m), 2.66(1H, m), 2.83(2H, m) 3.00–3.35(6H, m), 3.76(1H, m), 3.93(2H, m), 4.61(1H, bs), 7.46(3H, m), 7.67(1H, t), 7.70–8.00(6H, m), 8.37(1H, d) | 541 |
| 86 | 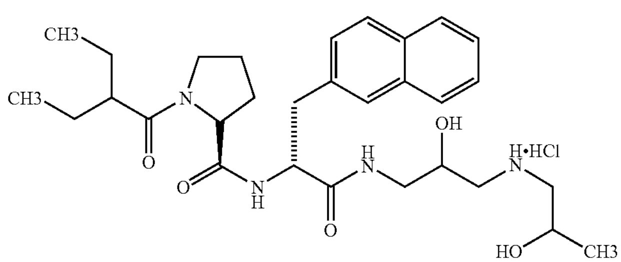 | II | 0.75–0.85(6H, m), 1.05–1.15 (3H, m), 1.30–1.55(6H, m)), 1.60–1.70(2H, m), 1.80–1.90 (1H, m), 2.35–2.45(1H, m), 2.75–3.50(8H, m), 3.85–4.05 (2H, m), 4.25–4.30(1H, m), 4.50–4.60(1H, m), 5.25–5.40 (1H, m), 5.65–5.80(1H, m), 7.40–7.50(4H, m), 7.70(1H, s), 7.80–7.90(4H, m), 8.15–8.20(1H, m), 8.40–8.65(2H, m) | 541 |

| Ex. No. | Structure | Methods | $^1$H-NMR($\delta$ ppm): | FAB-MS $(M+H)^+$ |
|---|---|---|---|---|
| 87 | 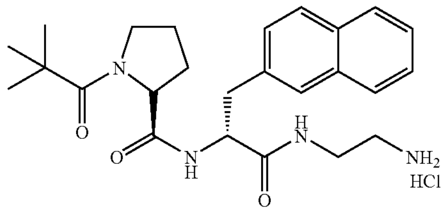 | II | 1.14(9H, s), 1.31(1H, m), 1.60–1.90(3H, m)2.91(2H, m), 3.04(1H, m), 3.20–3.60 (5H, m), 4.28(1H, m), 4.52(1H, m)7.45(3H, m), 7.69, 7.69(1H, s), 7.83(3H, ), 8.16(1H, m), 8.50(1H, br) | 439 |
| 88 | 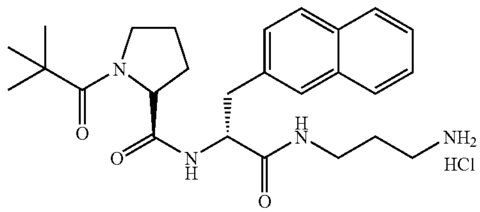 | II | 1.30(9H, s), 1.30(1H, m), 1.60–1.95(5H, m), 2.77(2H, m)2.95(1H, m), 3.10–3.70 (5H, m), 4.27(1H, m), 4.48(1H, m), 7.46(3H, m), 7.75–8.00(6H, m), 8.10(1H, t), 8.40(1H, d) | 453 |
| 89 | 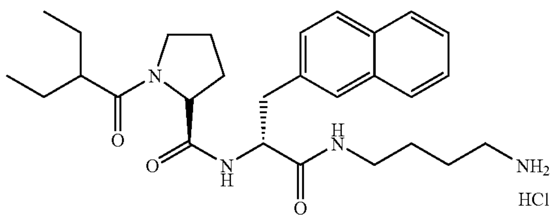 | II | 0.80(6H, m), 1.25–1.92(12H, m), 2.39(1H, m), 2.74(2H, m), 2.96(1H, m), 3.12(2H, m), 3.25–3.65(3H, m), 4.28(1H, m), 4.49(1H, m), 7.45(3H, m), 7.70(1H, s), 7.75–7.97(6H, m), 8.01(1H, t), 8.52(1H, d) | 481 |
| 90 | 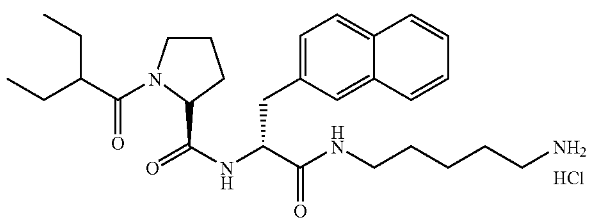 | II | 0.80(6H, m)1.15–1.95(14H, m), 2.39(1H, m), 2.65(2H, m)2.93(1H, m), 3.09(2H, m), 3.20–3.70(3H, m), 4.27(1H, t), 4.48(1H, m), 7.45(3H, m), 7.69(1H, s), 7.82(6H, m), 7.97.8.54(1H, d) | 495 |
| 91 | 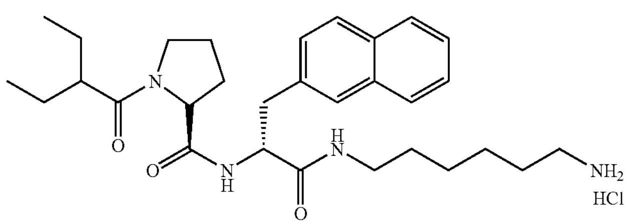 | II | 0.79(6H, m), 1.10–2.00(16H, m), 2.39(1H, m),, 2.74(2H, m), 2.90(1H, m), 3.09(2H, m), 3.20–3.70(3H, m), 4.264.45(1H, m), 7.45(3H, m), 7.69(1H, s), 7.73–8.00 (7H, m)8.49(1H, d) | 509 |
| 92 | 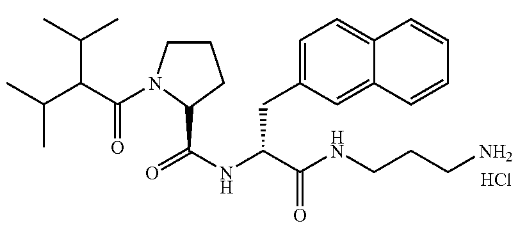 | II | 0.70–1.00(12H, m), 1.35–1.50 (1H, m), 1.60–2.00(7H, m), 2.10–3.70(9H, m), 4.15–4.30 (1H, m), 4.40–4.60(1H, m), 7.30–7.55(3H, m), 7.70(1H, s), 7.75–8.00(6H, m), 8.10–8.25(1H, m), 8.53(1H, d) | 495 |
| 93 | 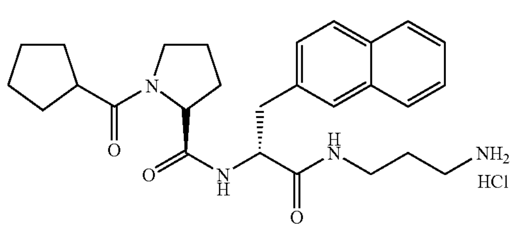 | II | 1.30–2.00(14H, m), 2.40–4.00 (9H, m), 4.21(1H, dd), 4.35–4.55(1H, m), 7.30–7.55 (3H, m), 7.70(1H, s), 7.75–8.00(6H, m), 8.14(1H, t), 8.44(1H, d) | 465 |

-continued

| Ex. No. | Structure | Methods | $^1$H-NMR($\delta$ ppm): | FAB-MS $(M+H)^+$ |
|---|---|---|---|---|
| 94 | 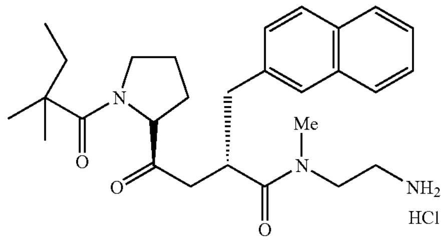 | II | 0.82(3H, t), 1.22(6H, s), 1.22(1H, m), 1.45–2.00(5H, m), 2.38(3H, m), 2.76(2H, t), 3.23(1H, m), 3.38(2H, t), 3.62(1H, m), 4.13(1H, m), 4.84(1H, m), 6.63(1H, d), 7.31–7.60(3H, m), 7.66(1H, s), 7.78(3H, m) | 467 |
| 95 | 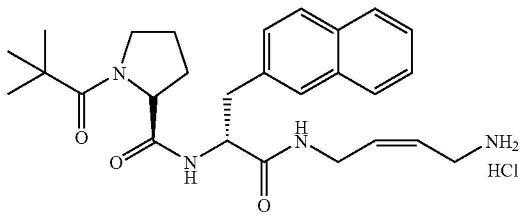 | II | 1.13(9H, m), 1.29(1H, m), 1.56–1.90(3H, m)2.95(1H, m), 3.32(1H, m), 3.40–3.85 (4H, m), 3.83(2H, t), 4.27(1H, m), 4.49(1H, m), 5.59(1H, m), 7.45(3H, m), 7.70(1H, s), 7.82(3H, m), 8.07(2H, br), 8.23(1H, t), 8.41(1H, d) | 465 |
| 96 | 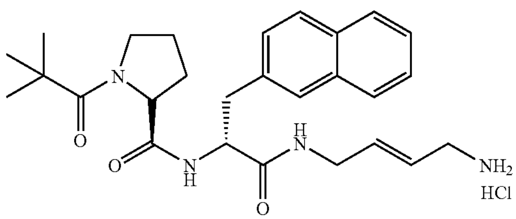 | II | 1.12(9H, s), 1.29(1H, m), 1.65(2H, m), 1.73(1H, m), 2.96(1H, m), 3.25–3.85(7H, m), 4.28(1H, m), 4.53(1H, m), 5.64(1H, m), 5.78(1H, m), 7.45(3H, m), 7.71(1H, s), 7.83(3H, m), 8.12(2H, br), 8.26(1H, t), 8.42(1H, d) | 465 |
| 97 | 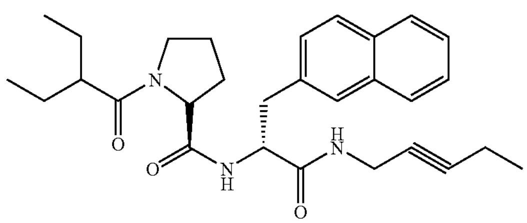 | II | 0.78(6H, t), 1.38(6H, m), 1.59(1H, m), 1.81(1H, m), 2.35(1H, m), 2.89(1H, m), 3.26(1H, m), 3.43(2H, m), 3.65–4.20(4H, m), 4.28(1H, m), 4.59(1H, m), 7.47(3H, m), 7.70(1H, s), 7.83(3H, m), 8.38(3H, br), 8.48(1H, d), 8.64(1H, t) | 497 |
| 98 | 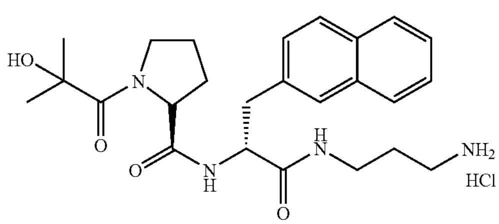 | II | 1.47(3H, s), 1.54(3H, s), 1.62(2H, m), 1.72–2.00(3H, m), 2.17(1H, m), 2.67(2H, m), 3.05–3.45(6H, m), 4.02(1H, m), 4.57(1H, m), 7.49(3H, m), 7.77(1H, s), 7.80–7.95(3H, m), 8.00(3H, br), 8.38(1H, br)8.84(1H, t) | 455 |
| 99 | 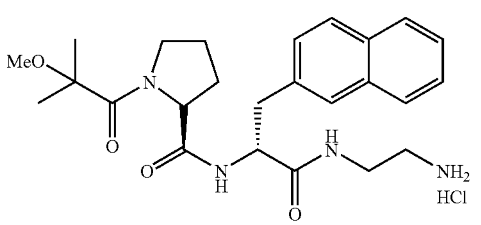 | II | 1.25(3H, s), 1.27(3H, s), 1.70(2H, m), 1.81(1H, m), 2.85–3.05(1H, m), 3.74(1H, m), 4.32(1H, m), 4.55(1H, m), 7.45(3H, m), 7.70(1H, s), 7.83(3H, m), 8.00–8.25 (4H, m), 8.59(1H, d) | 455 |

-continued

| Ex. No. | Structure | Methods | $^1$H-NMR($\delta$ ppm): | FAB-MS (M+H)$^+$ |
|---|---|---|---|---|
| 100 | 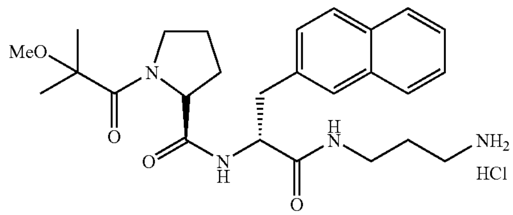 | II | 1.20–2.00(6H, m), 1.24(3H, s), 1.27(3H, s), 2.70–2.90(2H, br), 2.94(1H, t), 3.00–3.90 (5H, m), 3.10(3H, s), 4.30(1H, t), 4.45–4.65(1H, m), 7.30–7.55(3H, m), 7.70(1H, s), 7.80–8.20(7H, m), 8.49(1H, d) | 469 |
| 101 | 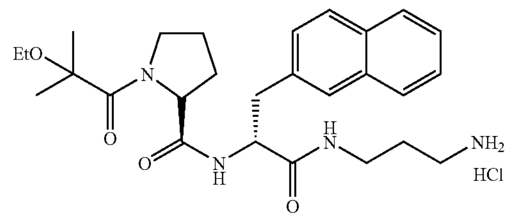 | II | 1.08(3H, t), 1.26(3H, s), 1.28(3H, s), 1.60–2.00(6H, m), 2.60–3.40(8H, m), 3.50–3.90(4H, m), 4.28(1H, dd), 4.45–4.70(1H, m), 7.30–8.20(9H, m), 7.70(1H, s), 8.50(1H, d) | 483 |
| 102 | 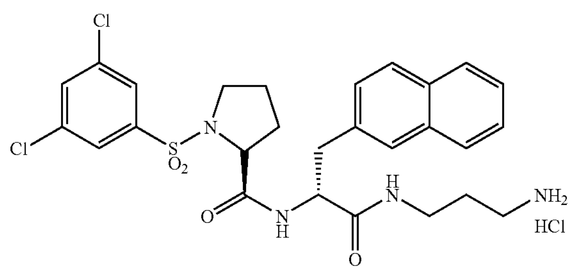 | II | 1.30–1.80(6H, m), 2.60–3.50 (8H, m), 4.15–4.35(1H, m), 4.50–4.70(1H, m), 7.30–7.95 (11H, m), 7.99(1H, s), 8.11(1H, dt), 8.36(1H, dd) | 577 579 |
| 103 | 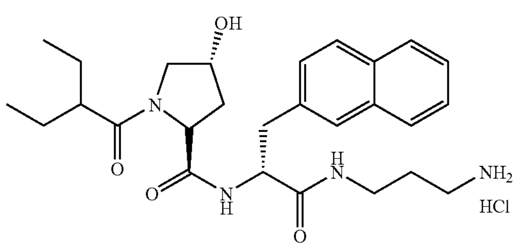 | II | 0.77(3H, t), 0.82(3H, t), 1.30–1.90(8H, m), 2.20–3.60 (9H, m), 3.90–4.60(3H, m), 7.30–7.55(3H, m), 7.60–8.05(7H, m), 8.18(1H, t), 8.69(1H, d) | 483 |
| 104 | 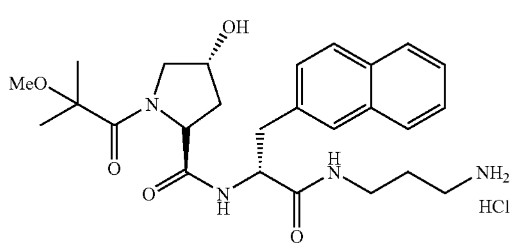 | II | 1.25(3H, s), 1.27(3H, s), 1.60–1.90(2H, m), 2.40–2.70 (9H, 3.10(3H, s), 3.86(1H, d), 4.10–4.25(1H, br), 4.30–4.70 (2H, m), 7.30–8.20(10H, m), 7.70(1H, s), 8.63(1H, d) | 485 |
| 105 | 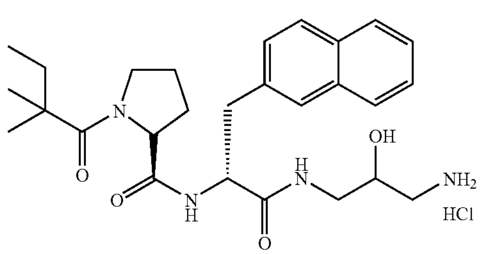 | I | 0.76(3H, t), 1.09(6H, s), 1.15–1.90(6H, m), 2.65(1H, m), 2.80–3.70(7H, m), 3.79(1H, m), 4.27(1H, m), 4.52(1H, m), 5.61(1H, br), 7.45(3H, m), 7.70(1H, s), 7.75–8.00(6H, m), 8.14(1H, m), 8.37(1H, m) | 483 |

| Ex. No. | Structure | Methods | ¹H-NMR(δ ppm): | FAB-MS (M+H)⁺ |
|---|---|---|---|---|
| 106 | 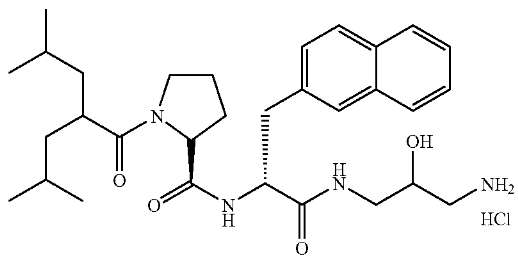 | I | 0.83(12H, m), 1.08(2H, m), 1.41(5H,, m), 1.67(2H, m), 1.85(1H, m), 2.40–3.55(9H, m), 3.78(1H, m), 4.23(1H, m), 4.55(1H, m)5.68(1H, bs), 7.46(3H, m), 7.69(1H, s), 7.75–8.00(6H, m), 8.18(1H, m), 8.45(1H, m) | 539 |
| 107 | 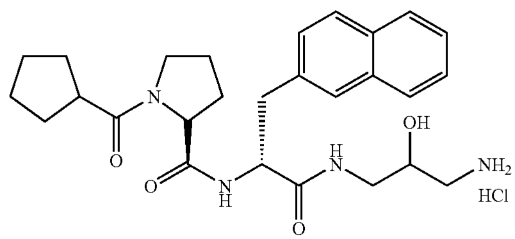 | II | 1.10–1.90(12H, m), 2.50–3.80(10H, m), 4.30(1H, m), 4.55(1H, m), 7.30–7.80 (7H, m) | 481 |
| 108 | 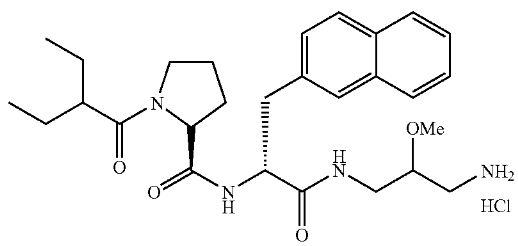 | II | 0.79(6H, t), 1.30–1.50(6H, m)1.65–1.90(4H, m), 2.30–2.45(1H, m)2.70–2.85 (1H, m), 2.90–3.00(2H, m), 3.15–3.55(6H, m), 4.20–4.30 (1H, m), 4.45–4.60(1H, m), 7.40–7.50(3H, m), 7.71(1H, s), 7.80–7.95(7H, m), 8.21(1H, q), 8.50(1H, dd) | 497 |
| 109 | 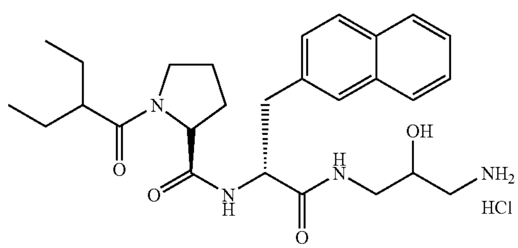 | I | 0.80(6H, t), 1.30–1.58(6H, m), 1.60–2.00(8H, m), 2.38–2.48(2H, m), 2.65(6H, bs), 2.76–3.00(1H, m), 3.00–3.30(2H, m), 3.48–3.58 (1H, m)3.70–3.82(1H, m)4.25–4.40(1H, m), 5.58–5.71(1H, m), 6.85–6.98 (3H, d), 7.89(3H, bs), 8.11(1H, q), 8.30–8.45(1H, m) | 487 |
| 110 | 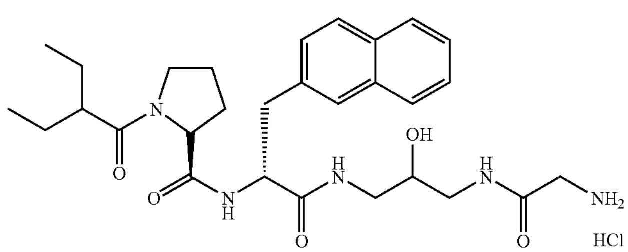 | III | 0.79(6H, t), 1.30–1.90(8H, m), 2.40–3.70(12H, m), 4.30(1H, m), 4.55(1H, m), 7.35–8.50(13H, m) | 540 |
| 111 | 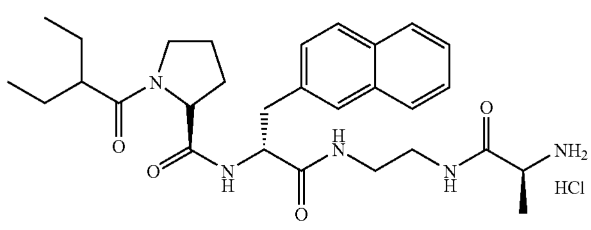 | III | 0.79(6H, m), 1.25–1.55(5H, m), 1.36(3H, d), 1.60–1.95 (3H, m), 2.38(1H, m), 2.97(1H, m), 3.05–3.65 (7H, m), 3.82(1H, m), 4.30(1H, t), 4.49(1H, m), 7.46(3H, m), 7.71(1H, s), 7.82(3H, m), 8.20(3H, br), 8.58(2H, br) | 524 |

-continued
| Ex. No. | Structure | Methods | ¹H-NMR(δ ppm): | FAB-MS (M+H)⁺ |
|---|---|---|---|---|
| 112 | 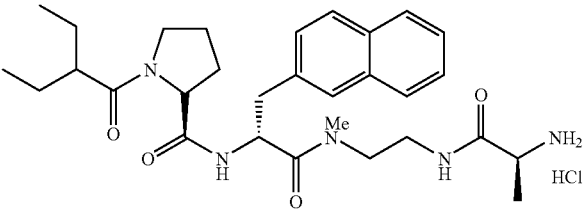 | III | 0.80(6H, t), 1.25–1.60(5H, m), 1.32(3H, d), 1.60–1.95(3H, m), 2.42(1H, m), 2.85–3.70 (8H, m), 4.28(1H, m), 4.45(1H, m), 7.47(3H, m), 7.71(1H, s), 7.80(3H, m), 8.10–8.65(5H, br) | 538 |
| 113 | 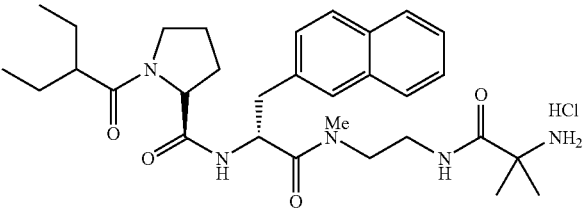 | III | 0.80(6H, t), 1.25–1.50(5H, m), 1.56(3H, s), 1.58(3H, m), 1.63–1.95(3H, m), 2.40(1H, m), 2.85–3.65(8H, m), 4.30(1H, t), 4.46(1H, t), 7.46(3H, m), 7.73(1H, s), 7.82(3H, m), 8.24(4H, br), 8.64(1H, d) | 552 |
| 114 | 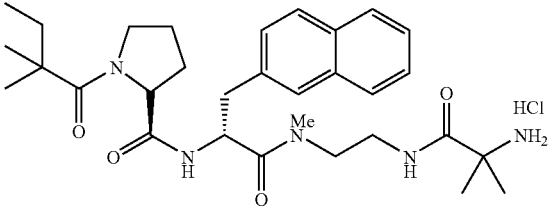 | III | 0.77(3H, t), 1.10(3H, s), 1.12(3H, s), 1.26(1H, m), 1.35–1.85(5H, m), 1.55(3H, s), 1.57(3H, s), 2.35–3.55 (10H, m), 3.60(1H, m), 4.38(1H, m), 4.47(1H, m), 7.45(3H, m), 7.71(1H, s), 7.83(3H, m), 8.17(4H, br), 8.48(1H, br) | 552 |
| 115 | 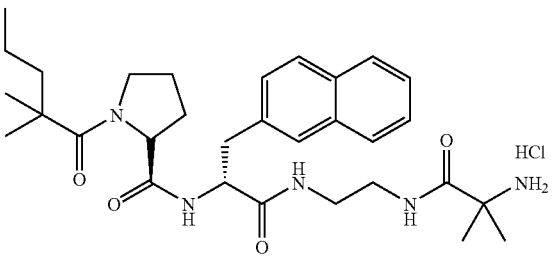 | III | 0.82(3H, t), 1.10(6H, s). 1.05–2.90(8H, m), 1.48(3H, s), 1.49(3H, s), 2.90–3.70 (8H, m), 4.29(1H, bs), 4.47(1H, m), 7.45(3H, m), 7.71(1H, s), 7.75–7.90(3H, m), 8.07(1H, bs), 8.25(3H, bs), 8.42(1H, bs), 8.55(1H, m) | 552 |
| 116 | 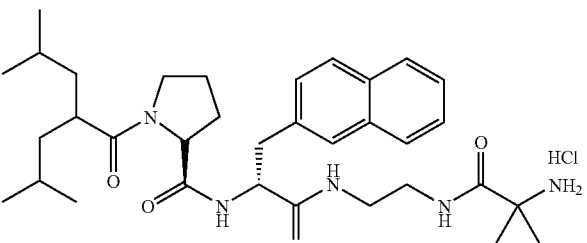 | III | 0.84(12H, m), 1.12(2H, m), 1.43(5H, m), 1.47(6H, s), 1.60–1.95(3H, m), 2.57(1H, m), 2.96(1H, m), 3.05–3.40 (3H, m), 3.48(2H, m), 4.26(1H, t), 4.49(1H, m), 7.45(3H, m), 7.70(1H, s), 7.82(3H, m), 8.08(1H, br), 8.22(3H, br), 8.37(1H, br), 8.54(1H, d) | 594 |
| 117 | 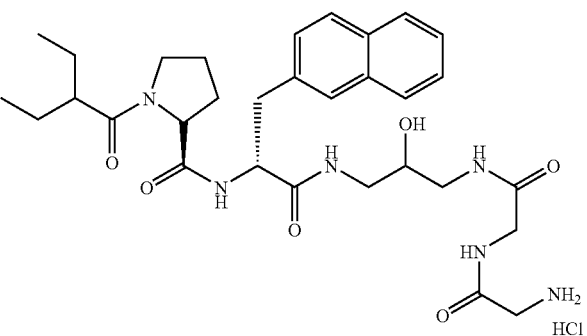 | III | 0.80(6H, t), 1.30–1.90(8H, m), 2.40–3.80(14H, m), 4.29(1H, m), 4.55(1H, m), 7.35–8.75(14H, m) | 597 |

| Ex. No. | Structure | Methods | ¹H-NMR(δ ppm): | FAB-MS (M+H)⁺ |
|---|---|---|---|---|
| 119 | 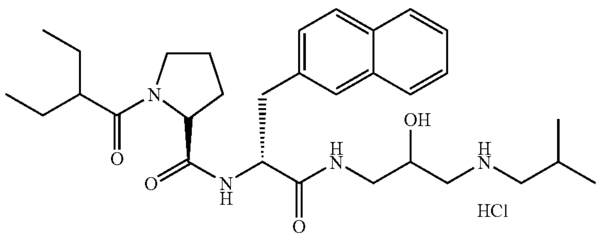 | V | 0.79(6H, t), 0.94(6H, d), 1.30–2.10(9H, m), 2.40–3.60 (11H, m), 3.92(1H, m), 4.27(1H, q), 4.60(1H, m), 7.40–8.70(7H, m) | 539 |
| 120 | 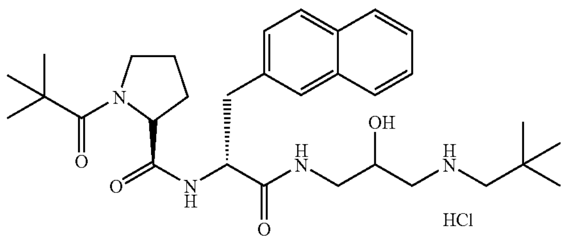 | V | 1.00(9H, s), 1.13(9H, s), 1.33(1H, m), 1.68(2H, m), 1.78(1H, m), 2.70–2.90(3H, m), 2.98(1H, m), 3.21–3.40 (2H, m), 3.40–3.70(2H, m), 4.00(1H, m), 4.28(1H, m), 4.55(1H, m), 5.68(1H, br), 7.45(3H, m), 7.71(1H, s), 7.82(3H, m), 8.10–8.40(4H, m). | 539 |
| 121 | 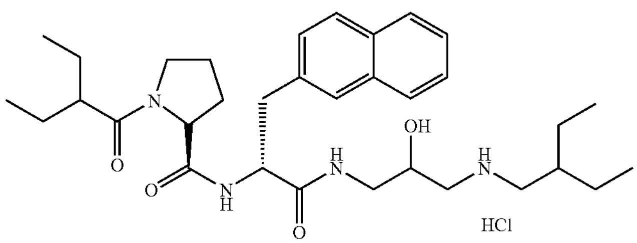 | V | 0.81(12H, m), 1.38(9H, m), 1.68(3H, m), 1.87(1H, m), 2.39(1H, m), 2.79(3H, m), 2.98(2H, m), 3.14(1H, m), 3.20–3.60(4H, m), 3.94(1H, m)4.27(1H, m), 4.56(1H, m), 5.72(1H, br), 7.45(3H, m), 7.70(1H, s), 7.82(3H, m), 8.16(1H, t), 8.31(2H, br), 8.48(1H, d) | 567 |
| 122 | 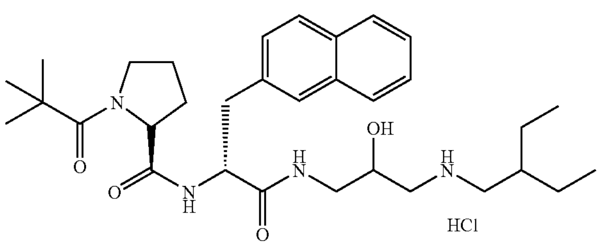 | V | 0.84(6H, t), 1.13(9H, s), 1.34(5H, m), 1.55–1.90(4H, m), 2.79(3H, m), 2.98(2H, m), 3.16(1H, m), 3.20–3.45 (2H, m), 3.45–3.70(2H, m), 3.95(1H, m), 4.28(1H, m), 4.54(1H, m), 5.67(1H, br), 7.46(3H, m), 7.70(1H, s), 7.81(3H, m), 8.17(1H, br), 8.35(1H, m), 8.47(2H, br) | 553 |
| 123 | 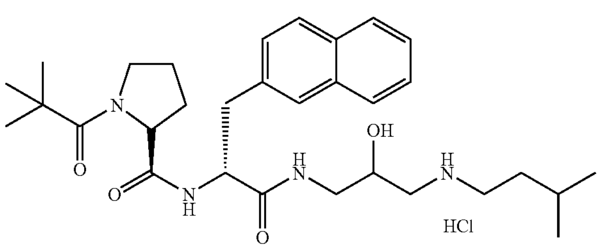 | V | 0.88(6H, d), 1.13(9H, s), 1.30(1H, m), 1.45–1.90(6H, m), 2.60–3.70(10H, m), 3.89(1H, m), 4.28(1H, m), 4.53(1H, m), 5.67(1H, br), 7.45(3H, m), 7.70(1H, s), 7.81(3H, m), 8.158.35(1H, d), 8.56(2H, br) | 539 |
| 124 | 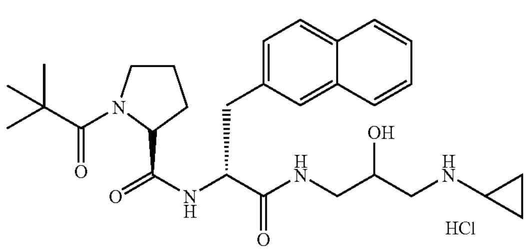 | IV | 0.71(2H, m), 0.85(2H, m), 1.13(9H, s), 1.31(1H, m), 1.67(2H, m), 1.77(1H, m), 2.60–3.70(9H, m), 3.91(1H, m), 4.28(1H, m), 4.54(1H, m), 7.48(3H, m), 7.70(1H, s), 7.83(3H, m), 8.18(1H, m), 8.33(1H, m), 8.82(2H, br) | 509 |

| Ex. No. | Structure | Methods | ¹H-NMR(δ ppm): | FAB-MS (M+H)⁺ |
|---|---|---|---|---|
| 125 | 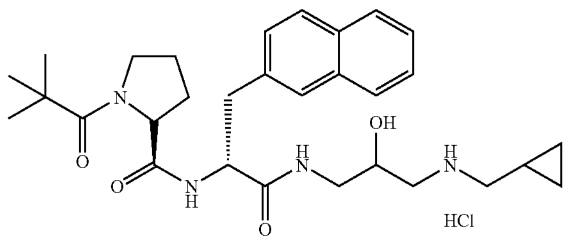 | V | 0.35(2H, m), 0.55(2H, m), 1.06(1H, m), 1.12(9H, s), 1.32(1H, m), 1.66(2H, m), 1.77(1H, m), 2.76(3H, m), 2.90–3.85(7H, m), 3.91(1H, m), 4.28(1H, m), 4.55(1H, m), 7.45(3H, m), 7.70(1H, s), 7.82(3H, m), 8.19(1H, t), 8.36(1H, m), 8.67(2H, br) | 523 |
| 126 | 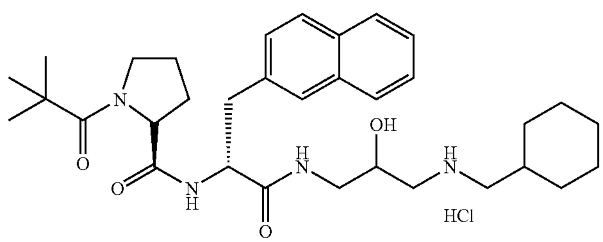 | IV | 0.80–1.40(5H, m), 1.13(9H, s), 1.55–1.90(10H, m), 2.74(2H, m), 2.97(2H, m), 3.05–3.70(6H, m), 3.91(1H, m), 4.26(1H, m), 4.54(1H, m), 7.45(3H, m), 7.70(1H, s), 7.82(3H, m), 8.16(1H, t), 8.33(1H, m), 8.41(2H, br) | 565 |
| 127 | 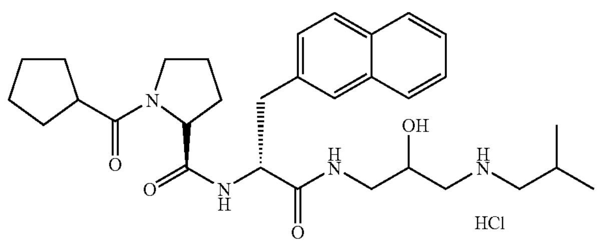 | V | 1.00(6H, d), 1.10–2.10(13H, m), 2.70–3.80(12H, m), 4.15(1H, m), 4.35(1H, m), 7.30–7.80(7H, m) | 537 |
| 128 | 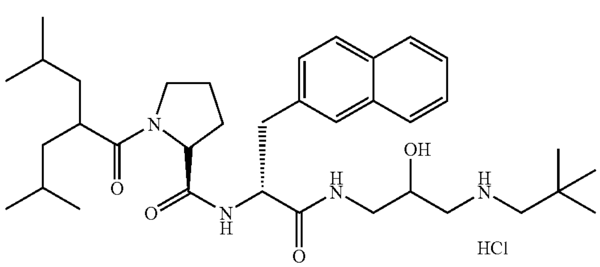 | V | 0.83(12H, m), 1.01(9H, s), 1.11(2H, m), 1.30–1.50(5H, m), 1.69(2H, m), 1.86(1H, m), 2.65–3.55(10H, m), 4.00(1H, m), 4.26(1H, m), 4.58(1H, m), 5.78(1H, br), 7.46(3H, m), 7.71(1H, s), 7.82(3H, m), 8.24(1H, m), 8.42(3H, m) | 609 |
| 129 | 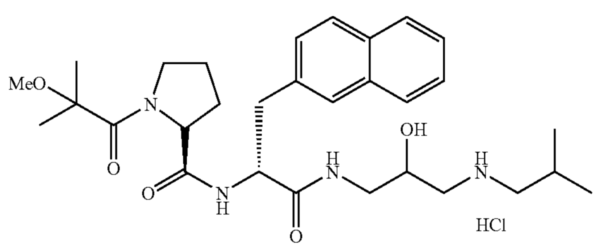 | V | 0.93(6H, d), 1.24(3H, s), 1.26(3H, s), 1.66(2H, m), 1.83(1H, m), 1.99(1H, m), 2.72(3H, m), 2.95(2H, m), 3.05–3.40(3H, m), 3.11(3H, s), 3.51(1H, m), 3.75(1H, m), 3.93(1H, m), 4.31(1H, t), 4.60(1H, m), 5.66(1H, br), 7.46(3H, m), 7.70(1H, s), 7.81(3H, m), 8.17(1H, t), 8.41(1H, d), 8.42(2H, br) | 541 |
| 130 | 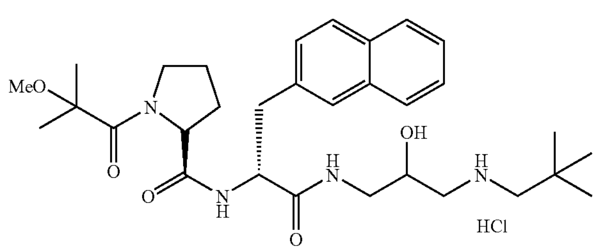 | V | 1.00(9H, s), 1.24(3H, s), 1.26(3H, s), 1.66(2H, m), 1.83(1H, m), 2.77(3H, m), 2.93(2H, m), 3.10–3.45(3H, m), 3.55(1H, m), 3.74(1H, m), 4.00(1H, m), 4.31(1H, m), 4.60(1H, m), 5.69(1H, br), 7.46(3H, m), 7.71(1H, s), 7.80(3H, m), 8.10–8.50(4H, m) | 555 |

-continued

| Ex. No. | Structure | Methods | ¹H-NMR(δ ppm): | FAB-MS (M+H)⁺ |
|---|---|---|---|---|
| 131 | 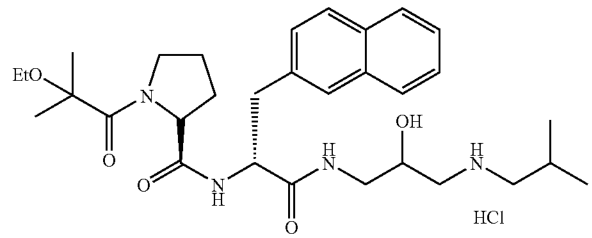 | V | 0.94(6H, d), 1.09(3H, d), 1.25(3H, s), 1.27(3H, s), 1.66(2H, m), 1.83(1H, m), 2.00(1H, m), 2.72(2H, m), 2.97(2H, m), 3.10–3.65(7H, m), 3.78(1H, m), 3.95(1H, m), 4.30(1H, m), 4.59(1H, m), 7.45(3H, m), 7.71(1H, s), 7.84(3H, m), 8.20(1H, t), 8.45(1H, m), 8.57(2H, br) | 555 |
| 132 | 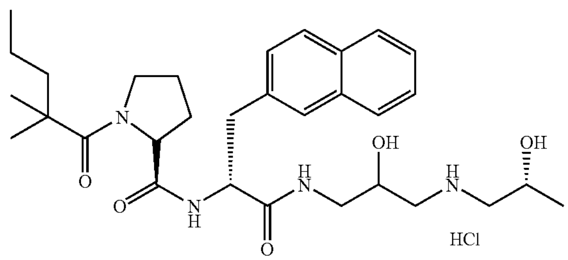 | I | 0.82(3H, t), 1.09(6H, s), 1.10(3H, d), 1.10–1.80(8H, m), 2.70–3.20(7H, m), 3.40–3.70(3H, m), 3.95(2H, bs), 4.29(1H, bs), 4.50–4.55 (1H, m), 5.30(1H, bs), 5.65(1H, bs), 7.38–7.50(3H, m), 7.70(1H, s), 7.75–7.79 (3H, m), 8.10–8.20(1H, m), 8.25–8.60(3H, m) | 555 |
| 133 | 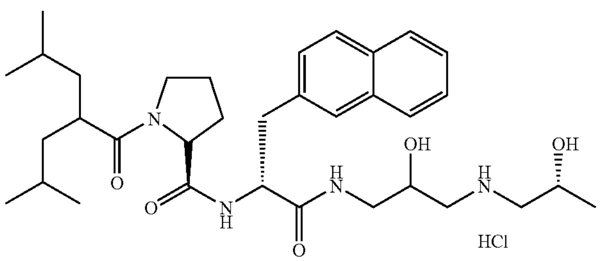 | I | 0.75–0.90(15H, m), 1.05–1.20 (6H, m), 1.30–1.60(6H, m), 1.60–1.95(3H, m), 2.65–3.20 (6H, m), 3.40–3.60(2H, m), 3.95(2H, bs), 4.20–4.30(1H, m), 4.50–4.60(1H, m), 5.30(1H, d), 5.70(1H, d), 7.40–7.55(3H, m), 7.70(1H, s), 7.75–8.90(3H, m), 8.15–8.45(2H, m) | 597 |
| 134 | 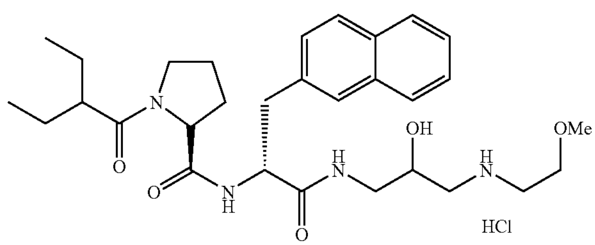 | IV | 0.80(6H, t), 1.25–1.60(5H, m), 1.67(2H, m), 1.84(1H, m), 2.44(1H, m), 2.80(1H, m), 2.90–3.20(5H, m), 3.28(2H, m), 3.30(3H, s), 3.48(2H, m), 3.60(2H, m), 3.92(1H, m), 4.29(1H, m), 4.56(1H, m), 7.45(3H, m), 7.71(1H, s), 7.82(3H, m), 8.17(1H, t), 8.47(1H, m), 8.55–8.80(2H, br) | 541 |
| 135 | 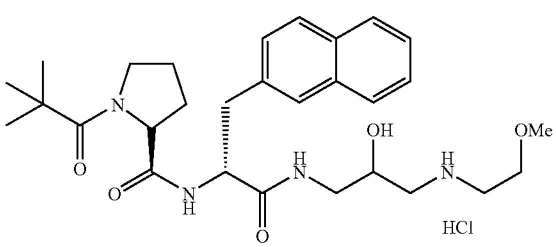 | IV | 1.12(9H, s), 1.29(1H, m), 1.66(2H, m), 1.77(1H, m), 2.70–4.00(12H, m), 3.30(3H, s), 4.27(1H, m), 4.54(1H, m), 7.46(3H, m), 7.70(1H, s), 7.81(3H, m), 8.16(1H, t), 8.33(1H, m), 8.50–8.80(2H, br) | 527 |
| 136 | 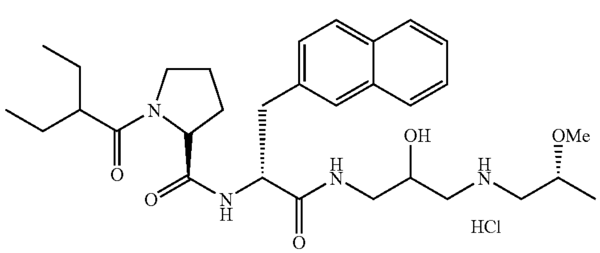 | V | 0.80(6H, t), 1.12(3H, d), 1.30–1.60(5H, m), 1.60–1.76 (2H, m), 1.76–1.98(1H, m), 2.35–3.20(10H, m), 3.32(3H, s), 3.40–3.50(1H, m), 3.58–3.74(1H, m), 3.84–4.00 (1H, m), 4.20–4.30(1H, m), 4.49–4.70(1H, m), 5.65–5.80 (1H, m), 7.38–7.52(2H, m), 7.52–7.75(2H, m), 7.75–8.00 (3H, m), 8.05–8.25(2H, m), 8.30–8.65(3H, m) | 555 |

-continued
| Ex. No. | Structure | Methods | ¹H-NMR(δ ppm): | FAB-MS (M+H)⁺ |
|---|---|---|---|---|
| 137 | 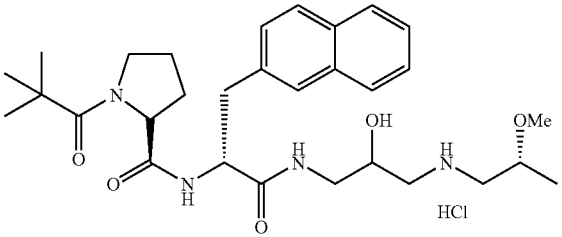 | V | 1.13(12H, m), 1.30(1H, m), 1.55–1.90(3H, m), 2.65–4.20 (12H, m), 3.29(3H, s), 4.27(1H, m), 4.56(1H, m), 7.45(3H, m), 7.70(1H, s), 7.82(3H, m), 8.17(1H, br), 8.25–8.70(3H, m), | 541 |
| 138 | 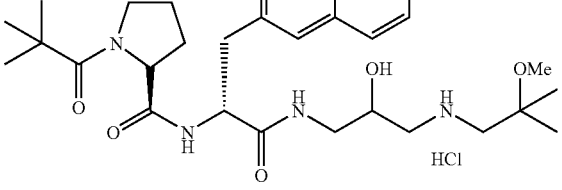 | V | 1.13(9H, s), 1.21(6H, s), 1.30(1H, m), 1.55–1.90(3H, m), 2.70–3.70(10H, m), 3.98(1H, m), 4.28(1H, m), 4.54(1H, m), 7.46(3H, m), 7.71(1H, s), 7.82(3H, m), 8.15–8.45(4H, m) | 555 |
| 139 | 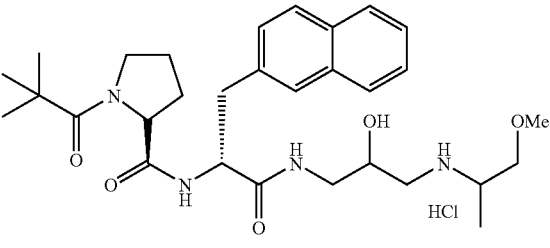 | V | 1.22(9H, t), 1.21(3H, m), 1.66(3H, m), 1.77(1H, m), 2.70–3.70(11H, m), 3.31(3H, s), 3.92(1H, m), 4.28(1H, m), 4.54(1H, m), 7.47(3H, m), 7.70(1H, s), 7.82(3H, m), 8.18(1H, br), 8.25–8.65(3h, br) | 541 |
| 140 | 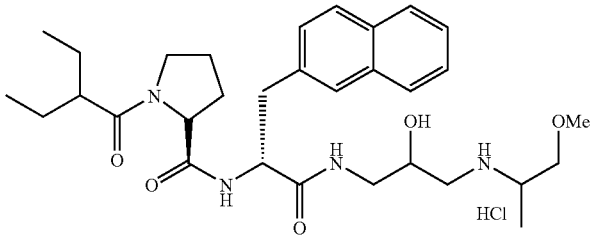 | V | 0.79(6H, t), 1.20(3H, d), 1.43(5H, m), 1.66(2H, m), 1.82(1H, m), 2.38(1H, m), 2.70–3.60(11H, m), 3.31(3H, s), 3.92(1H, m), 4.28(1H, m), 4.56(1H, m), 7.45(3H, m), 7.70(1H, s), 7.82(3H, m), 8.19(1H, br), 8.30–8.65(3H, m) | 555 |
| 141 | 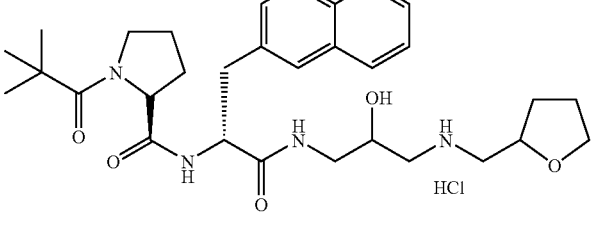 | IV | 1.12(9H, s), 1.30(1H, m), 1.45–2.10(7H, m), 2.60–3.62 (7Hm), 3.70(1H, m), 3.80 (1H, m), 3.92(1H, m), 4.14(1H, m), 4.29(1H, m), 4.54(1H, m), 7.45(3H, m), 7.70(1H, s), 7.82(3H, m), 8.18(1H, br), 8.32(1H, m), 8.40–8.85(2H, br) | 553 |
| 142 | 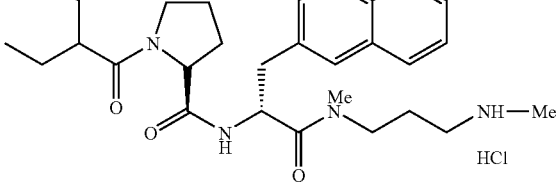 | II | 0.78(6H, m), 1.20–1.65(7H, m), 1.65–2.10(3H, m), 2.36(1H, m), 2.40–3.10(8H, m), 3.17(2H, m), 3.30(1H, m), 3.46(3H, m), 4.31(1H, m)5.03(1H, m), 7.45(3H, m), 7.70(1H, s), 7.83(3H, m), 8.31(1H, d), 8.50–8.90(3H, br) | 495 |

-continued

| Ex. No. | Structure | Methods | $^1$H-NMR($\delta$ ppm): | FAB-MS $(M+H)^+$ |
|---|---|---|---|---|
| 143 | 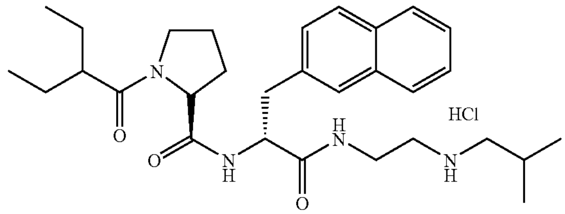 | V | 0.80(6H, m)0.94(6H, d), 1.30–1.60(5H, m), 1.71(1H, m), 1.90(2H, m), 2.42(1H, m), 2.74(2H, m), 2.95(2H, m), 3.25–3.60(5H, m), 4.27(1H, m), 4.52(1H, m), 7.45(3H, m), 7.70(1H, s), 7.83(3H, m), 8.26(1H, t), 8.55(1H, d), 8.58(2H, br) | 509 |
| 144 | 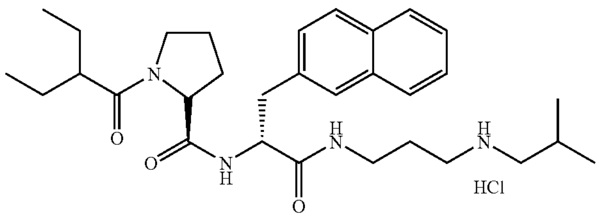 | V | 0.79(6H, t), 0.94(6H, d), 1.25–1.60(5H, m), 1.60–2.05 (6H, m), 2.44(1H, m), 2.66(2H, m), 2.83(2H, m), 2.98(1H, m), 3.05–3.40(1H, m), 3.48(2H, m), 4.27(1H, m), 4.49(1H, m), 7.46(3H, m), 7.70(1H, s), 7.82(3H, m), 8.20(1H, t), 8.52(1H, d), 8.53(2H, br) | 523 |
| 145 | 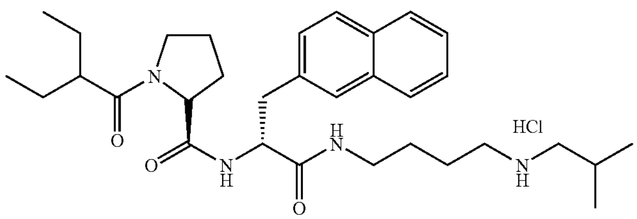 | V | 0.80(6H, m), 0.95(6H, d), 1.25–2.10(13H, m), 2.40(1H, m), 2.70(2H, m), 2.85(2H, m), 2.96(1H, m), 3.34(1H, m), 3.53(2H, m), 4.28(1H, m), 4.48(1H, m), 7.49(3H, m), 7.70(1H, s), 7.82(3H, m), 8.02(1H, t), 8.52(2H, br), 8.53(1H, d) | 537 |
| 146 | 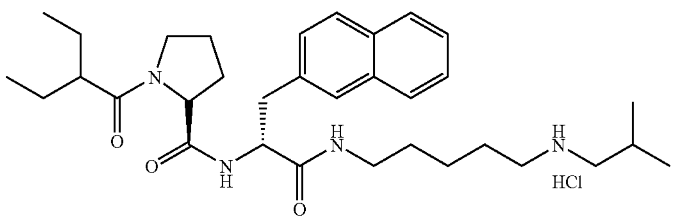 | V | 0.80(6H, m), 0.94(6H, d), 1.10–2.10(14H, m), 2.39(1H, m), 2.60–2.90(5H, m), 2.93(1H, m), 3.10(2H, m), 3.25–3.60(3H, m), 4.27(1H, m), 4.46(1H, m), 7.45(3H, m), 7.70(1H, s), 7.80(3H, m), 7.95(2H, t), 8.48(2H, br), 8.50(1H, d) | 551 |
| 147 | 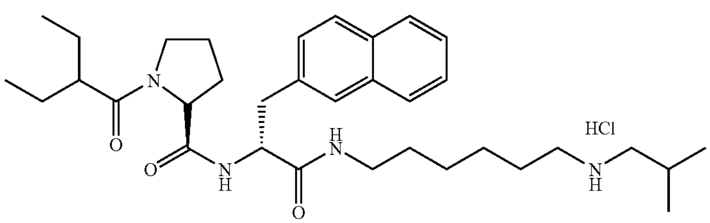 | V | 0.79(6H, m), 0.95(6H, d), 1.10–2.10(17H, m), 2.40(1H, m), 2.71(2H, m), 2.83(2H, m), 2.92(1H, m), 3.09(2H, m), 3.32(1H, m), 3.35–3.65 (2H, m), 4.27(1H, m), 4.45(1H, m), 7.44(3H, m), 7.69(1H, s), 7.82(3H, m), 7.94(1H, t), 8.50(1H, d), 8.55(2H, br) | 565 |
| 148 | 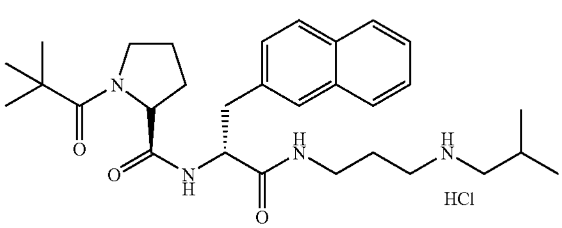 | V | 0.94(6H, d), 1.14(9H, s), 1.37(1H, m), 1.60–2.05(6H, m), 2.66(2H, m), 2.83(2H, m), 2.97(1H, m), 3.05–3.40 (3H, m), 3.40–3.70(2H, m), 4.28(1H, m), 4.50(1H, m), 7.45(3H, m), 7.70(1H, s), 7.82(3H, m), 8.14(1H, t), 8.37(1H, d), 8.51(1H, br), | 509 |
| 149 | 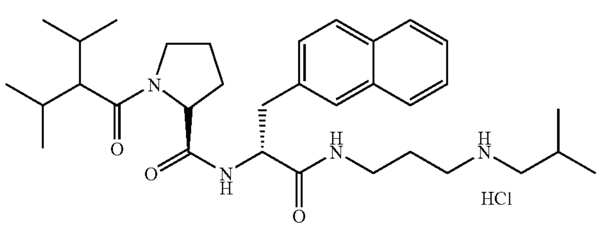 | V | 0.60–1.20(18H, m), 1.40–2.10 (4H, m), 2.20–3.80(11H, m), 4.20–4.70(2H, m), 7.10–8.00 (7H, m), 8.10–8.30(1H, m), 8.50–9.00(3H, m) | 551 |

-continued

| Ex. No. | Structure | Methods | $^1$H-NMR($\delta$ ppm): | FAB-MS (M+H)$^+$ |
|---|---|---|---|---|
| 150 | 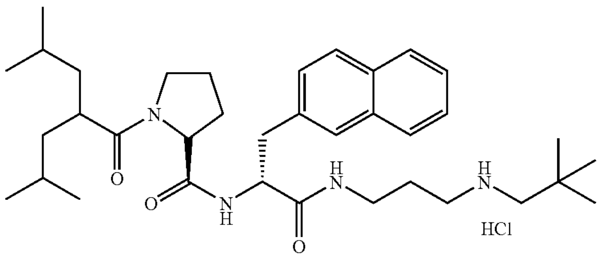 | V | 0.83(12H, m), 1.00(9H, s), 1.12(2H, m), 1.32–1.60(5H, m), 1.73(2H, m), 1.86(3H, m), 2.40–3.40(10H, m), 3.48(2H, m), 4.25(1H, m), 4.51(1H, m), 7.35–7.52(3H, m), 7.71(1H, s), 7.84(3H, m), 8.22(3H, br)8.46(1H, d) | 593 |
| 151 | 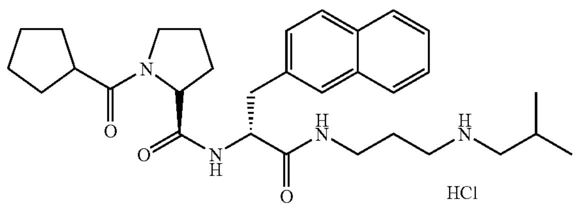 | V | 1.02(6H, d), 1.10–2.10(15H, m), 2.40–3.70(11H, m), 4.15–4.30(1H, m), 4.40–4.60 (1H, m), 7.35–7.60(3H, m), 7.78, (1H, s), 7.80–7.95(3H, m), 8.10–8.25(1Hm), 8.35–8.55(1H, m), 8.60–8.90(2H, br) | 521 |
| 152 | 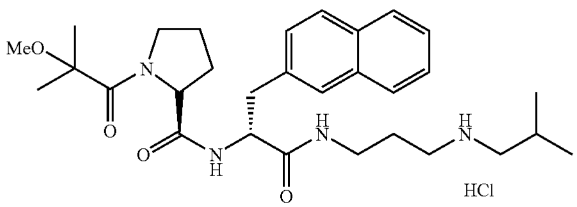 | V | 0.95(6H, d), 1.10–2.10(7H, m), 1.25(3H, s), 2.40–3.90 (10H, m), 3.11(3H, s), 4.32(1H, t), 4.45–4.70(1H, m), 7.35–7.60(3H, m), 7.71(1H, s), 7.75–7.95(3H, m), 8.10–8.25(1H, m), 8.51(1H, d), 8.65–8.90(2H, br) | 525 |
| 153 | 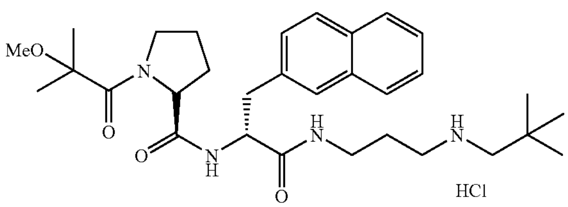 | V | 0.99(9H, s), 1.24(3H, s), 1.25(3H, s), 1.55–2.00(6H, m), 2.30–3.90(10H, m), 3.09(3H, s), 4.20–4.65(2H, m), 7.30–7.95(6H, m), 7.70(1H, s), 8.10–8.70(4H, m) | 539 |
| 154 | 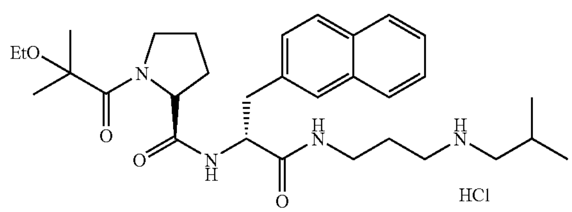 | II | 0.94(6H, d), 1.08(3H, t), 1.26(3H, s), 1.28(3H, s), 1.50–2.10(7H, m), 2.60–3.90 (12H, m), 4.20–4.35(1H, m), 4.45–4.60(1H, m), 7.30–8.20 (7H, m), 7.70(1H, s), 8.46(1H, d), 8.50–8.80(2H, br) | 539 |
| 155 | 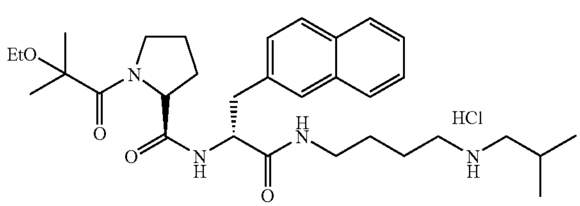 | II | 0.95(6H, d), 1.08(3H, t), 1.10–2.10(9H, m), 1.26(3H, s), 1.28(3H, s), 2.50–4.00(12H, m), 4.20–4.60(2H, m), 7.30–8.10(7H, m), 7.71(1H, s), 8.57(1H, d), 8.60–8.90(2H, br) | 553 |

| Ex. No. | Structure | Methods | ¹H-NMR(δ ppm): | FAB-MS (M+H)⁺ |
|---|---|---|---|---|
| 156 | 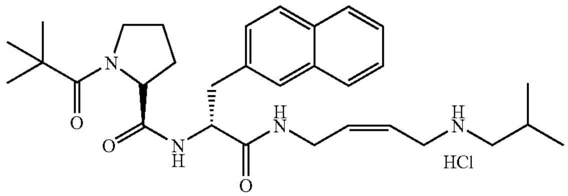 | V | 0.95(6H, d), 1.13(9H, s), 1.30(1H, m), 1.60–1.90(3H, m), 1.99(1H, m), 2.72(2H, m), 2.94(1H, m), 3.33(1H, m), 3.45–3.75(2H, m), 3.83(2H, m), 4.27(1H, br), 4.49(1H, m), 5.55–5.80(2H, m), 7.35–7.55(3H, m), 7.69(1H, s), 7.80–7.92(3H, m), 8.24(1H, t), 8.39(1H, d), 8.88(2H, br) | 521 |
| 157 | 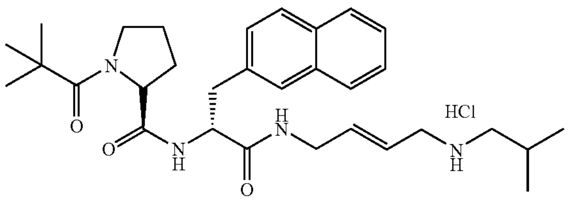 | V | 0.93(6H, d), 1.12(9H, s), 1.28(1H, m), 1.60–1.85(3H, m), 1.95(1H, m), 2.66(2H, m), 2.95(1H, m), 3.25–3.70 (5H, m), 3.77(2H, m), 4.28(1H, br), 4.53(1H, m), 5.66(1H, m), 5.87(1H, m), 7.45(3H, m), 7.70(1H, s), 7.83(3H, m), 8.25(1H, t), 8.40(1H, d), 8.74(2H, br) | 521 |
| 158 | 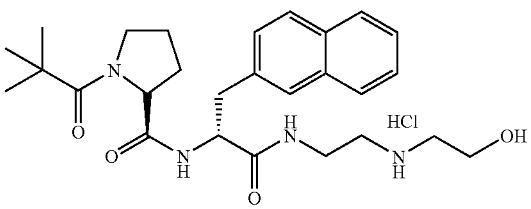 | II | 1.14(9H, s), 1.32(1H, m), 1.60–1.90(3H, m), 3.02(5H, m), 3.42–3.75(7H, m), 4.28(1H, m), 4.53(1H, m), 7.45(3H, m), 7.69(1H, s), 7.82(3H, m), 8.20(1H, t), 8.47(1H, d), 8.83(2H, br) | 483 |
| 159 | 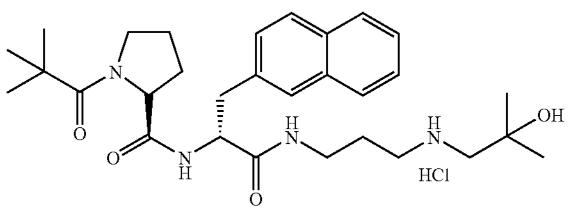 | II | 1.14(9H, s), 1.20(6H, s), 1.60–2.00(6H, m), 2.40–3.80 (10H, m), 4.20–4.70(2H, m), 5.12(1H, s), 7.30–7.60(3H, m), 7.70(1H, s), 7.75–7.90(3H, m), 8.10–8.50(4H, m) | 525 |
| 160 | 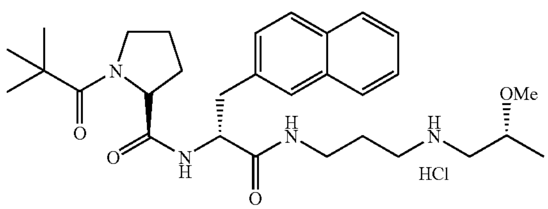 | V | 1.13(12H, m), 1.32(1H, m), 1.60–1.90(5H, m), 2.60–3.60 (11H, m), 4.27(1H, m), 4.48(1H, m), 7.46(3H, m), 7.70(1H, s), 7.81(3H, m), 8.11(1H, m), 8.35(1H, m), 8.50–8.80(2H, br) | 525 |
| 161 | 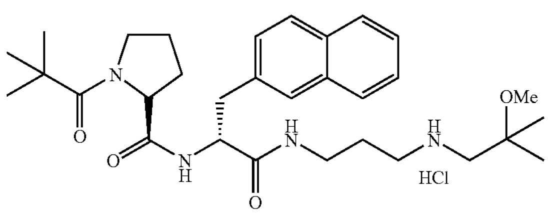 | V | 1.00–2.00(6H, m), 1.14(9H, s), 1.20(6H, s), 2.70–4.00(10H, m), 3.16(3H, s), 4.20–4.60(2H, m), 7.30–7.55(3H, m), 7.71(1H, s), 7.75–7.90(3H, m), 8.10–8.20(1H, m), 8.30–8.55(3H, m) | 539 |
| 162 | 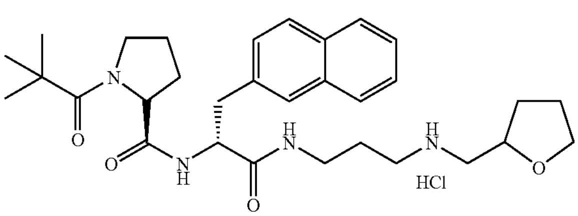 | II | 1.13(9H, s), 1.40–2.10(10H, m), 2.40–3.90(12H, m), 4.00–4.70(3H, m), 7.30–9.00 (10H, m), 8.37(1H, d) | 537 |

-continued

| Ex. No. | Structure | Methods | $^1$H-NMR(δ ppm): | FAB-MS (M+H)$^+$ |
|---|---|---|---|---|
| 163 | 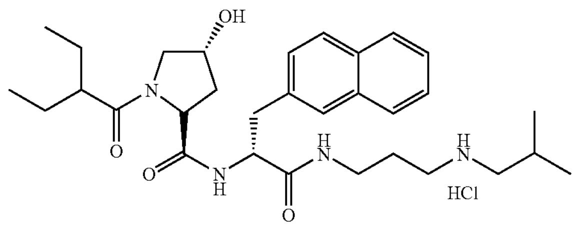 | V | 0.70–0.90(6H, m), 0.95(6H, d), 1.30–2.05(9H, m), 2.30–3.80(11H, m), 4.15–4.30 (1H, br), 4.35–4.60(2H, m), 7.30–7.95(7H, m), 7.72(1H, s), 8.10–8.30(1H, m), 8.60–8.85(2H, m) | 539 |
| 164 | 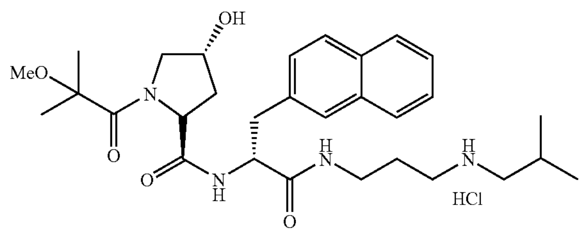 | II | 0.94(6H, d), 1.25(3H, s), 1.27(3H, s), 1.60–2.10(7H, m), 2.40–3.60(7H, m), 3.10(3H, s), 3.80–3.95(1H, m), 4.10–4.25(1H, br), 4.30–4.65(2H, m), 7.30–7.95 (6H, m)<7.71(1H, s), 8.00–8.20(1H, m), 8.40–8.75(3H, m) | 541 |
| 165 | 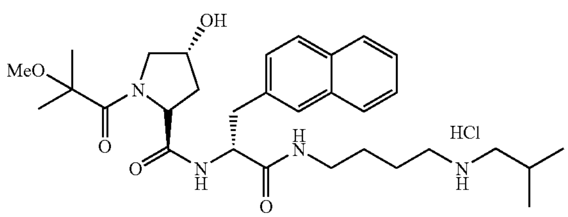 | II | 0.95(6H, d), 1.10–2.10(7H, m), 1.24(3H, s), 1.28(3H, s), 2.60–3.70(10H, m), 3.10(3H, s), 3.44(1H, d), 4.10–4.20(1H, br), 7.30–8.00(6H, m), 7.71(1H, s), 8.50–8.80(3H, m) | 555 |
| 166 | 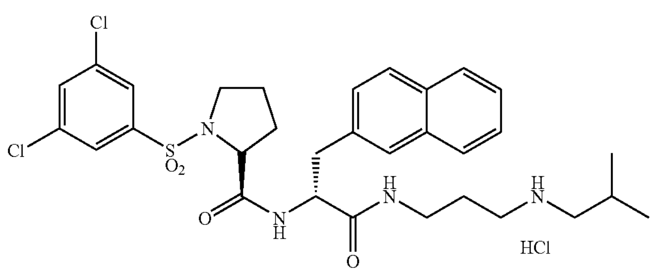 | V | 0.92(6H, d), 1.30–2.10(7H, m), 2.30–3.90(10H, m), 4.20–4.40(1H, m), 4.50–4.80(1H, m), 7.20–8.60(12H, m), 8.65–8.90(2H, br) | 634 |
| 167 | 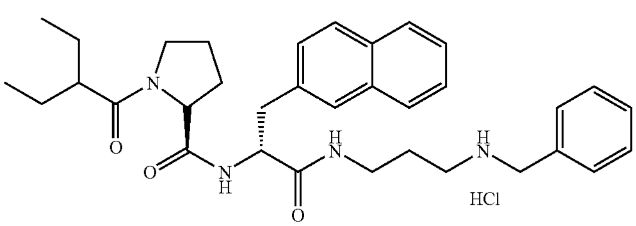 | V | 0.79(6H, t), 1.25–1.60(5H, m), 1.60–2.00(5H, m), 2.38(1H, m), 2.70–3.05(3H, m), 3.13(1H, m), 3.27(2H, m), 3.48(2H, m), 4.10(2H, m), 4.29(1H, m), 4.49(1H, m), 7.44(6H, m), 7.53(2H, m), 7.71(1H, s), 7.82(3H, m), 8.22(1H, t), 8.53(1H, t), 9.12(2H, br) | 557 |
| 168 | 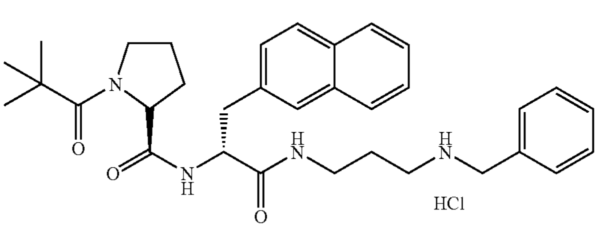 | V | 1.12(9H, s), 1.35(1H, m), 1.60–1.95(5H, m), 2.80–3.00(3H, m), 3.00–3.40(3H, m), 3.40–3.70(2H, m), 4.09(1H, m), 4.20–4.55 (2H, m), 7.42(6H, m), 7.52(2H, m), 7.70(1H, s), 7.82(3H, m), 8.15(1H, t), 8.34(1H, d), 9.07(2H, br) | 543 |

| Ex. No. | Structure | Methods | ¹H-NMR(δ ppm): | FAB-MS (M+H)⁺ |
|---|---|---|---|---|
| 169 | 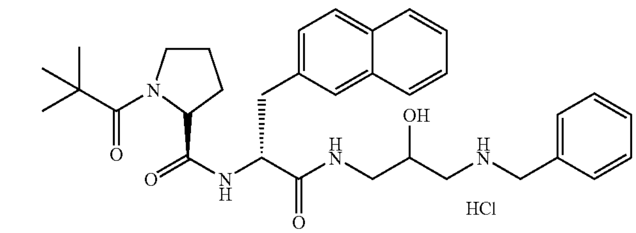 | IV | 1.10(9H, s), 1.29(1H, m), 1.66(2H, m), 1.76(1H, m), 2.75(1H, m), 2.93(2H, m), 3.05–3.70(5H, m), 3.93(1H, m), 4.13(2H, m), 4.28(1H, m), 4.54(1H, m), 7.35–7.60(8H, m), 7.70(1H, s), 7.82(3H, m), 8.18(1H, t), 8.31(1H, m), 8.85–9.15(2H, br) | 559 |
| 170 | 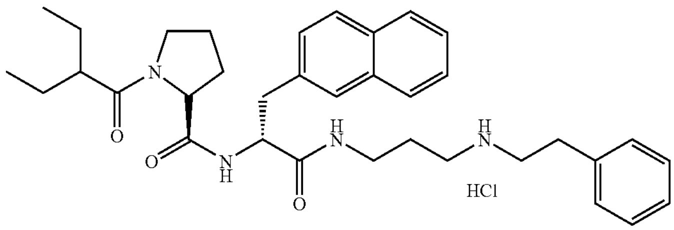 | V | 0.77(6H, t), 1.20–1.55(5H, m), 1.55–1.95(5H, m), 2.30–2.50(2H, m), 2.60–3.85 (10H, m), 4.27(1H, m), 4.48(1H, m), 7.05–7.55(8H, m), 7.69(1H, s), 7.80(3H, m), 8.17(1H, m), 8.50(1H, d), 8.78(2H, br) | 571 |
| 171 | 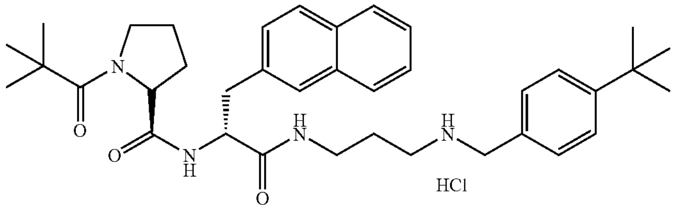 | V | 1.00–2.00(6H, m), 1.12(9H, s), 1.27(9H, s), 2.80–3.70(8H, m), 3.95–4.10(2H, m), 4.20–4.35(1H, br), 4.40–4.60 (1H, m), 7.71(1H, s), 7.75–7.90(3H, m), 8.10–8.25(1H, m), 8.43(1H, d), 9.10–9.40(2H, br) | 599 |
| 172 | 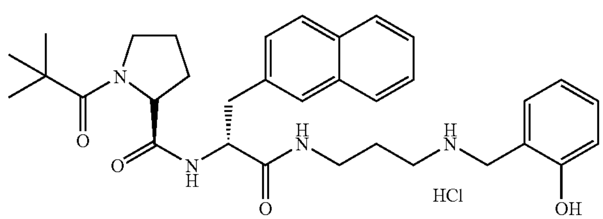 | V | 1.12(9H, s), 1.20–2.00(6H, m), 2.80–3.80(8H, m), 4.03(2H, s), 4.20–4.60(2H, m), 6.83(1H, t), 6.99(1H, d), 7.10–7.60(6H, m), 7.71(1H, s), 7.75–8.90(3H, m), 8.10–8.25(1H, m), 8.44(1H, d), 8.80–9.10(2H, br) | 559 |
| 173 | 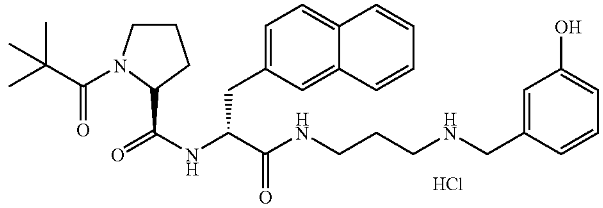 | V | 1.12(9H, s), 1.20–2.00(6H, m), 2.80–3.70(8H, m), 3.90–4.10(2H, m), 4.20–4.60 (2H, m), 6.82(1H, d), 6.93(1H, s), 9.95(1H, d), 7.20(1H, t), 7.30–7.55(3H, m), 7.71(1H, s), 7.75–7.95 (3H, m), 8.10–8.25(1H, m), 8.42(1H, d), 9.10–9.30 (2H, br), 9.60–9.85(1H, br) | 559 |
| 174 | 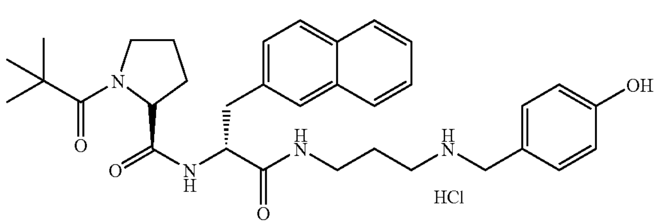 | V | 1.12(9H, s), 1.20–2.00(6H, m), 2.30–4.10(10H, m), 4.20–4.60(2H, m), 6.70–7.00 (2H, m), 7.20–8.00(9H, m), 8.05–8.25(1H, br), 8.30–8.60 (1H, m), 8.90–9.30(1H, br), 9.40–10.00(1H, br) | 559 |

-continued

| Ex. No. | Structure | Methods | ¹H-NMR(δ ppm): | FAB-MS (M+H)⁺ |
|---|---|---|---|---|
| 175 | 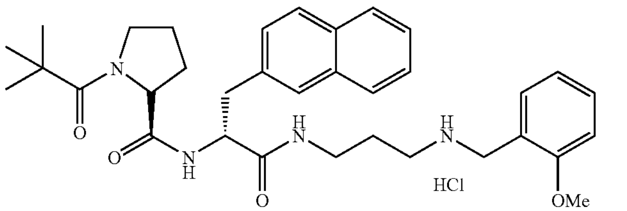 | V | 1.12(9H, s), 1.20–2.00(6H, m), 2.80–4.60(12H, m), 3.84(3H, s), 6.90–7.95(10H, m), 7.70(1H, s), 8.10–8.25 (1H, br), 8.43(1H, d), 8.90–9.20(2H, br) | 573 |
| 176 | 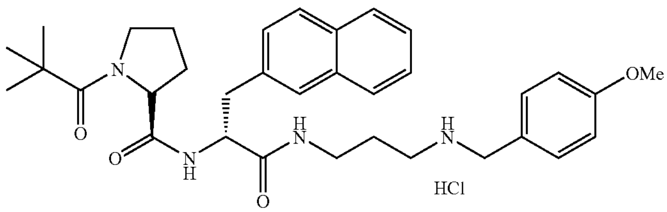 | V | 1.12(9H, s), 1.20–2.00(6H, m), 2.70–3.60(8H, m), 3.75(3H, s), 3.95–4.10(2H, m), 6.97(2H, d), 7.30–7.55 (5H, m), 7.70(1H, s), 7.75–7.90(3H, m), 8.10–8.25 (1H, m), 8.42(1H, d), 9.10–9.40(2H, br) | 573 |
| 177 | 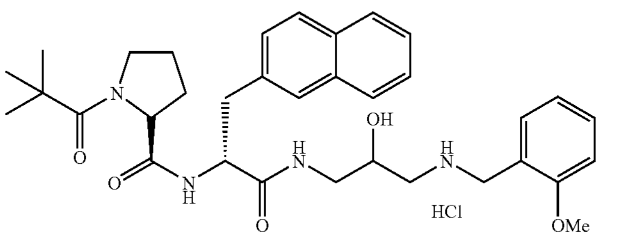 | V | 1.11(9H, s), 1.31(1H, m), 1.66(2H, m), 1.80(1H, m), 2.76(1H, m), 2.94(2H, m), 3.13(1H, m), 3.26(2H, m), 3.40–3.80(2H, m), 3.85(3H, s), 3.96(1H, m), 4.13(2H, m), 4.29(1H, m), 4.53(1H, m), 6.79(1H, t), 7.08(1H, d), 7.35–7.55(5H, m), 7.70(1H, s), 7.82(3H, m), 8.20(1H, t), 8.34(1H, m), 8.70–9.00(2H, br) | 589 |
| 178 | 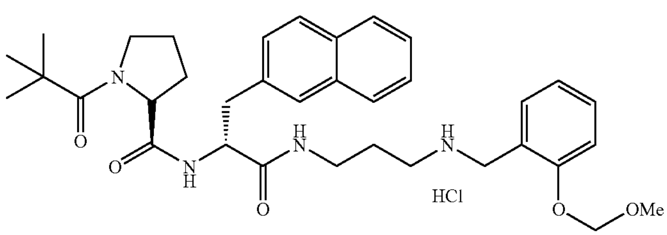 | V | 1.11(9H, s), 1.20–1.80(6H, m), 2.40–3.70(8H, m), 3.38(3H, s), 3.75(2H, s), 4.15–4.60(2H, m), 5.21(2H, s), 6.96(1H, t), 7.05(1H, d), 7.20(1H, t), 7.25–7.50(5H, m), 7.67(1H, s), 7.75–8.00 (4H, m), 8.30(1H, d) | 603 |
| 179 | 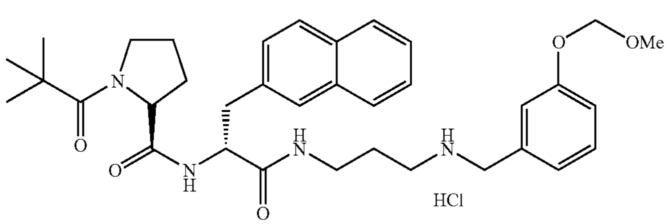 | V | 1.11(9H, s), 1.20–1.80(6H, m), 2.90(1H, dd), 3.10–3.70 (7H, m), 3.36(3H, s), 3.62(2H, s), 4.00–4.60(3H, m), 5.15(2H, s), 6.80–7.00 (3H, m), 7.20(1H, t), 7.30–7.75(3H, m), 7.67(1H, s), 7.75–7.95(4H, m), 8.29(1H, d) | 603 |
| 180 | 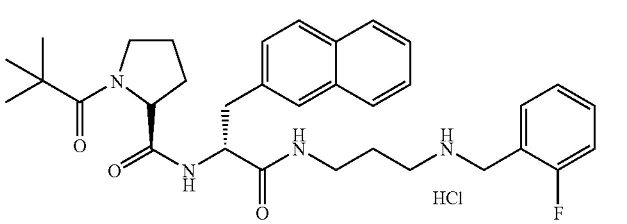 | V | 1.12(9H, m), 1.20–2.00(6H, m), 2.80–3.70(8H, m), 4.05–4.65(4H, m), 7.20–7.95 (10H, m), 7.71(1H, s), 8.10–8.25(1H, br), 8.35–8.55(1H, m), 9.20–9.60(2H, br) | 561 |

-continued

| Ex. No. | Structure | Methods | $^1$H-NMR(δ ppm): | FAB-MS $(M+H)^+$ |
|---|---|---|---|---|
| 181 | 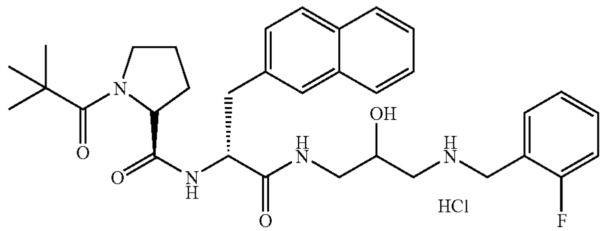 | V | 1.11(9H, m), 1.33(1H, m), 1.50–1.90(3H, m), 2.70–3.90(8H, m), 3.97(1H, m), 4.21(2H, m), 4.28(1H, m), 4.53(1H, m), 7.27(2H, m), 7.46(4H, m), 7.70(2H, m), 7.80(3H, m), 8.20(1H, t), 8.37(1H, br), 9.16(2H, br) | 577 |
| 182 | 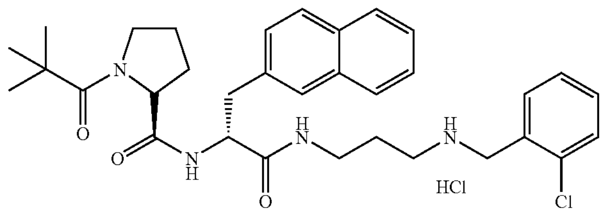 | V | 1.12(9H, s), 1.20–2.00(6H, m), 2.40–3.90(8H, m), 4.10–4.60(4H, m), 7.30–7.60(7H, m), 7.70(1H, s), 7.75–7.90(3H, m), 8.10–8.25(1H, m), 8.39(1H, d), 9.20–9.50(2H, br) | 577 579 |
| 183 | 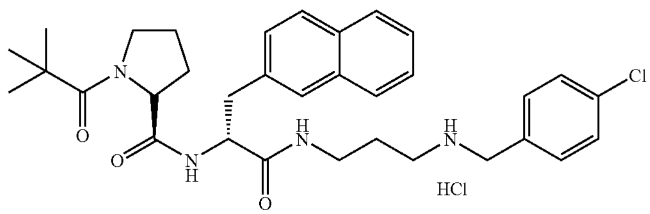 | V | 1.11(9H, s), 1.20–2.00(6H, m), 2.80–3.80(8H, m), 4.00–4.60(4H, m), 7.35–7.55(3H, m), 7.50(2H, d), 7.61(2H, d), 7.70(1H, s), 7.75–7.95(3H, m), 8.10–8.25(1H, m), 8.42(1H, d), 9.20–9.60(2H, br) | 577 579 |
| 184 | 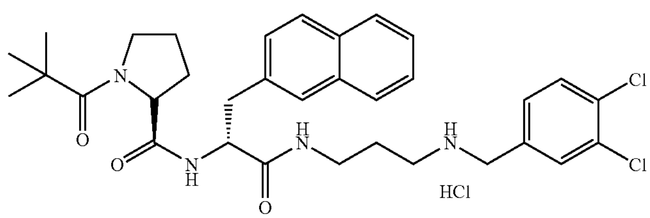 | V | 1.11(9H, s), 1.20–2.00(6H, m), 2.80–3.90(8H, m), 4.00–4.60(4H, m), 7.30–7.90(10H, m), 8.10–8.20(1H, m), 8.40(1H, d), 9.10–9.40(2H, br) | 411 413 |
| 185 | 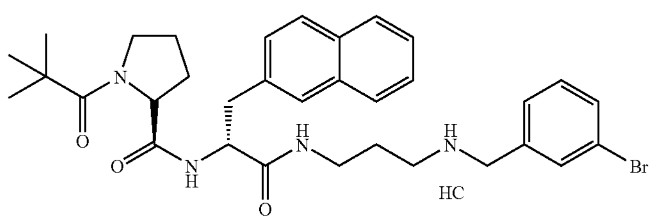 | V | 1.12(9H, s), 1.20–2.00(6H, m), 2.80–3.80(4H, m), 4.00–4.60(4H, m), 7.30–7.55(5H, m), 7.59(1H, t), 7.71(1H, s), 7.75–7.90(4H, m), 8.10–8.25(1H, m), 8.40–8.50(1H, m), 9.25–9.50(2H, br) | 621 623 |
| 186 | 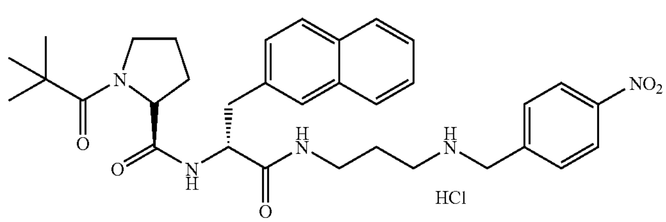 | V | 1.11(9H, s), 1.20–2.00(6H, m), 2.00(6H, m), 2.80–3.70(8H, m), 4.15–4.65(4H, m), 7.30–7.55(3H, m), 7.701H, s), 7.75–7.95(5H, m), 8.10–8.25(1H, m), 8.29(2H, d), 8.43(1H, d), 9.50–9.80(2H, br) | 588 |
| 187 | 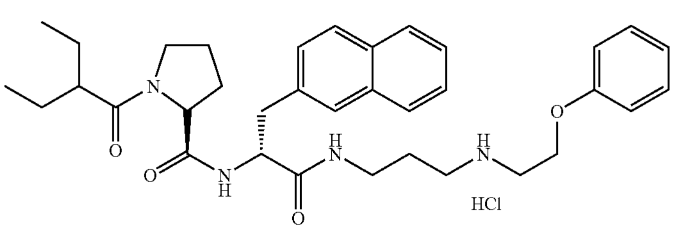 | V | 0.79(6H, t), 1.25–1.50(5H, m), 1.50–2.00(5H, m), 2.44(1H, m), 2.96(3H, m), 3.05–3.37(6H, m), 3.48(2H, m), 4.25(3H, m), 4.49(1H, m), 6.99(3H, m), 7.25–7.60(5H, m), 7.70(1H, s), 7.83(3H, m), 8.21(1H, t), 8.52(1H, d), 9.00(2H, br) | 587 |

| Ex. No. | Structure | Methods | ¹H-NMR(δ ppm): | FAB-MS (M+H)⁺ |
|---|---|---|---|---|
| 188 | 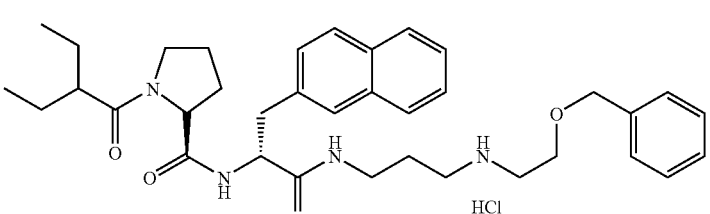 | V | 0.79(6H, t), 1.25–1.50(5H, m), 1.50–1.95(5H, m), 2.40–2.60(2H, m), 2.70–3.60(9H, m), 3.67(2H, m), 4.27(1H, m), 4.49(1H, m), 4.55(2H, s), 7.25–7.55(8H, m), 7.69(1H, s), 7.83(3H, m), 8.18(1H, t), 8.50(1H, d), 8.67(2H, br) | 601 |
| 189 | 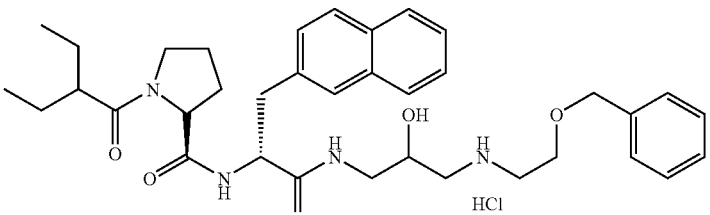 | V | 0.79(6H, t), 1.30–2.10(8H, m), 2.40–3.60(16H, m), 3.92(1H, m), 4.27(1H, m), 4.60(1H, m), 7.40–8.70 (12H, m) | 617 |
| 190 | 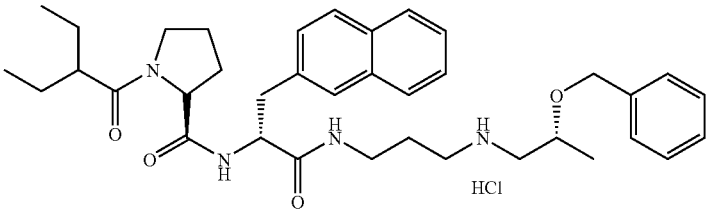 | V | 0.79(6H, t), 1.19(3H, d), 1.25–1.60(5H, m), 1.60–1.95(5H, m), 2.38(1H, m), 2.70–3.40(8H, m), 3.93(1H, m), 4.30(1H, m), 4.45–4.70(2H, m), 7.25–7.60(8H, m), 7.70(1H, s), 7.82(3H, m), 8.22(1H, t), 8.54(1H, d), 8.65(1H, br), 8.90(1H, br) | 615 |
| 191 | 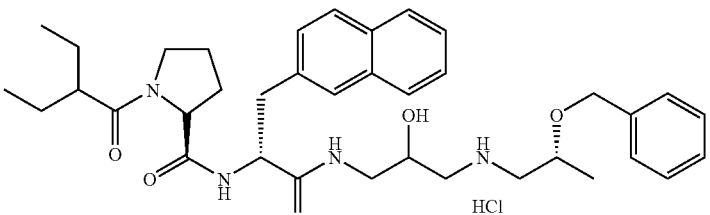 | II | 0.75–0.85(6H, m), 1.15 (1.20(3H, m), 1.25–1.55(6H, m), 1.60–1.70(2H, m), 1.75–1.95(1H, m), 2.30–2.45(2H, m), 2.75–3.30(9H, m), 3.80–3.95(1H, m), 4.20–4.30(1H, m), 4.45–4.80(3H, m), 5.75–5.85(1H, m), 7.25–7.50(7H, m), 7.65–7.90(4H, m), 8.15–8.25(1H, m), 8.40–8.65(2H, m) | 631 |
| 192 | 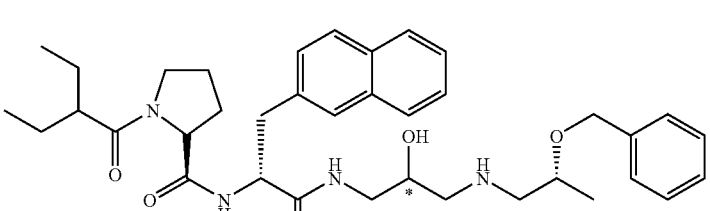 | II | 0.77(6H, t), 1.18(3H, d), 1.27–1.54(6H, m), 1.60–1.70(1H, m), 1.77–1.90(1H, m), 2.30–2.60(1H, m), 2.75–3.15(6H, m), 3.20–3.50(5H, m), 3.85–4.00(2H, m), 4.23–4.30(1H, m), 4.15–4.65(3H, m), 5.70–5.80(1H, m), 7.25–7.50(8H, m), 7.69(1H, s), 7.75–7.90(3H, ), 8.22(1H, t), 8.35–8.55(1H, m), 8.60–8.75(1H, m) | 631 |

| Ex. No. | Structure | Methods | $^1$H-NMR($\delta$ ppm): | FAB-MS $(M+H)^+$ |
|---|---|---|---|---|
| 193 | 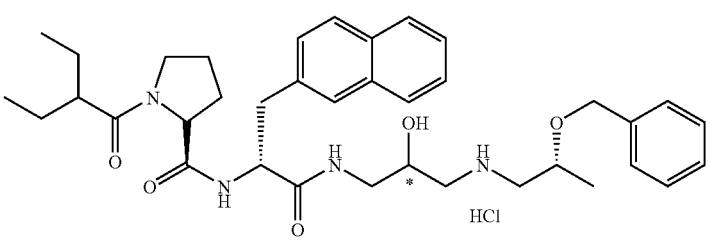 | II | 0.78(6H, dt), 1.18(3H, d), 1.27–1.54(6H, m), 1.58–1.72(1H, m), 1.75–1.93(1H, m), 2.32–2.60(1H, m), 2.74–3.32(9H, m), 3.42–3.57(2H, m), 3.85–4.00(2H, m), 4.25–4.32(1H, m), 4.42–4.65(3H, m), 5.70–5.80(1H, m), 7.25–7.50(8H, m), 7.70(1H, s), 7.75–7.90 (3H, m), 8.19(1H, t), 8.40–8.58(1H, m), 8.60–8.75(1H, m) | 631 |
| 194 | 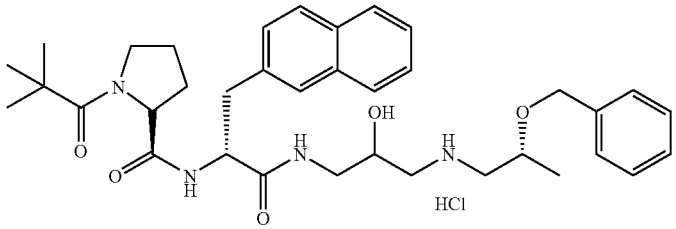 | V | 1.12(9H, s), 1.18(3H, d), 1.30(1H, m), 1.67(2H, m), 1.81, (1H, m), 2.70–3.85(9H, m), 3.94(2H, m), 4.28(1H, m), 4.45–4.70(3H, m), 7.25–7.55(8H, m), 7.69(1H, s), 7.82(3H, m), 8.18(1H, br), 8.33(1H, m), 8.40–8.80(2H, br) | 617 |
| 195 | 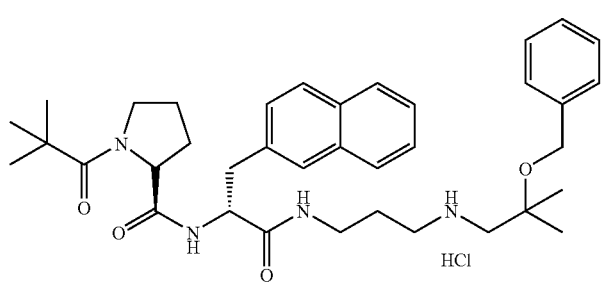 | V | 1.13(9H, s), 1.33(6H, s), 1.50–2.00(6H, m), 2.80–3.80(10H, m), 4.20–4.60(4H, m), 4.48(2H, s), 7.20–7.90(11H, m), 7.70(1H, s), 8.10–8.70 (4H, m) | 615 |
| 196 | 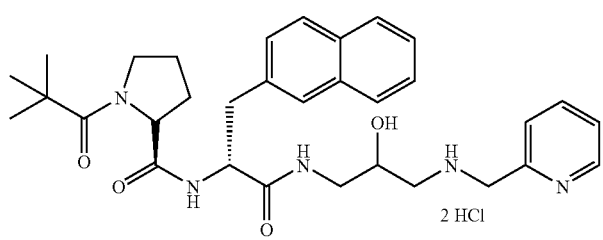 | V | 1.11(9H, s), 1.31(1H, m), 1.55–1.90(3H, m), 2.80–3.40(6H, m), 3.40–3.75(2H, m), 3.85–4.20(2H, m), 4.34(2H, m), 4.53(1H, m), 7.35–7.60(5H, m), 7.70(1H, s), 7.75–7.95(4H, m), 8.18(1H, t), 8.32(1H, m), 8.63(1H, d), 9.13(2H, br) | 560 |
| 197 | 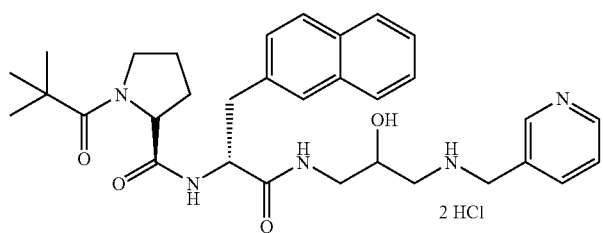 | V | 1.11(9H, s), 1.31(1H, m), 1.67(2H, m), 1.77(1H, m), 2.60–4.45(12H, m), 4.54(1H, m), 7.45(3H, m), 7.71(1H, s), 7.82(4H, m), 8.11(1H, br), 8.22(1H, t), 8.36(1H, m), 8.43(2H, br), 8.81(1H, br), 8.97(1H, br) | 560 |

-continued

| Ex. No. | Structure | Methods | $^1$H-NMR($\delta$ ppm): | FAB-MS $(M+H)^+$ |
|---|---|---|---|---|
| 198 | 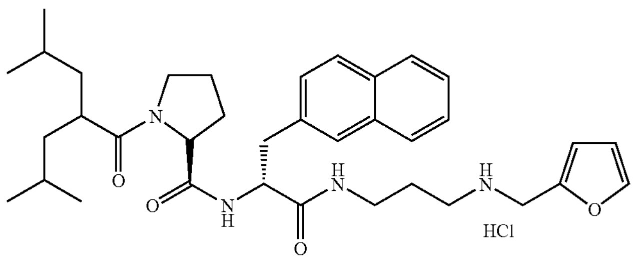 | V | 0.80(12H, m), 1.11(2H, m), 1.30–1.60(5H, m), 1.60–1.95(5H, m), 2.70–3.60(9H, m), 4.20(3H, m), 4.51(1H, m), 6.52(1H, s), 6.63(1H, d), 7.45(3H, m), 7.69(1H, s), 7.78(1H, s), 7.83(3H, m), 8.16(1H, t), 8.44(1H, d), 9.16(2H, br) | 603 |
| 199 | 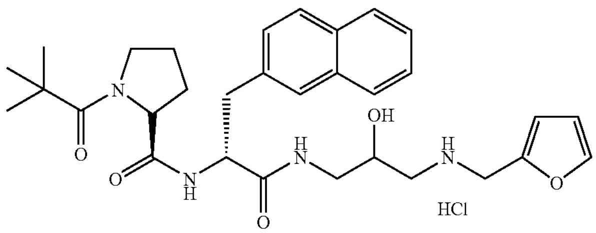 | V | 1.11(9H, s), 1.30(1H, m), 1.55–1.90(3H, m), 2.65–3.80(8H, m), 3.92(1H, m), 4.22(2H, m), 4.30(1H, m), 4.54(1H, m), 6.51(1H, s), 6.64(1H, d), 7.43(3H, m), 7.70(1H, s), 7.75(1H, s), 7.82(3H, m), 8.19(1H, t8, 8.36(1H, m), 9.15(2H, br) | 549 |
| 200 | 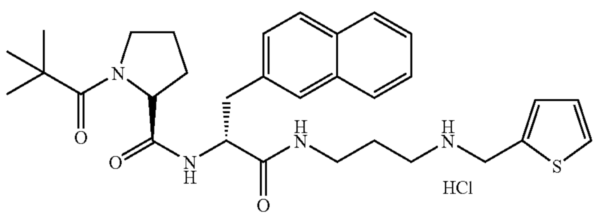 | V | 1.12(9H, s), 1.20–2.00(6H, m), 2.80–3.80(8H, m), 4.20–4.70(4H, m), 7.00–8.00(9H, m), 7.71(1H, s), 8.10–8.35(1H, br), 8.43(1H, d), 9.20–9.60 (2H, br) | 549 |
| 201 | 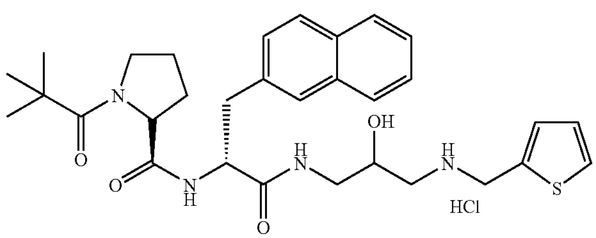 | V | 1.11(9H, s), 1.30(1H, m), 1.55–1.90(3H, m), 2.75(1H, m), 2.85–3.70 (7H, m), 3.92(1H, m), 4.28(1H, m), 4.37(2H, m), 4.54(1H, m), 7.08(1H, t), 7.31(1H, s), 7.45(3H, m), 7.62(1H, d), 7.69(1H, s), 7.83(3H, m), 8.18(1H, t), 8.31(1H, ), 9.05(2H, m) | 565 |
| 202 | 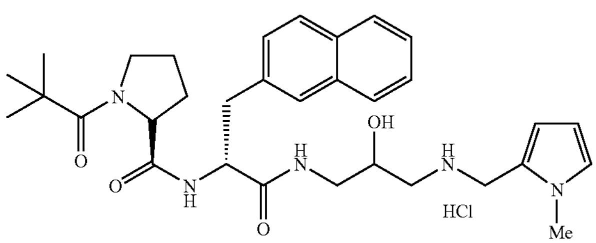 | V | 1.12(9H, s), 1.30(1H, m), 1.66(2H, m), 1.77(1H, m), 2.80(1H, m), 2.90–3.20(3H, m), 3.20–3.75(4H, m), 3.66(3H, s), 3.94(1H, m), 4.15(2H, m), 4.29(1H, m), 4.54(1H, m), 6.01(1H, m), 6.25(1H, m), 6.79(1H, m), 7.45(3H, m), 7.70(1H, s), 7.83(3H, m), 8.21(1H, t), 8.35(1H, m), 8.82(2H, br) | 562 |
| 203 | 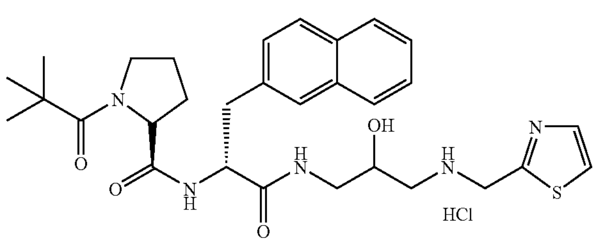 | V | 1.12(9H, s), 1.30(1H, m), 1.66(2H, m), 1.76(1H, m), 2.95(2H, m), 3.13(2H, m), 3.31(2H, m), 3.40–3.90 (2H, m), 3.97(1H, m), 4.28(1H, m), 4.59(3H, m), 7.45(3H, m), 7.70(1H, s), 7.75–8.00(5H, m), 8.19(1H, t), 8.31(1H, m), 9.30(1H, br), 9.48(1H, br) | 566 |

-continued

| Ex. No. | Structure | Methods | ¹H-NMR(δ ppm): | FAB-MS (M+H)⁺ |
|---|---|---|---|---|
| 204 | 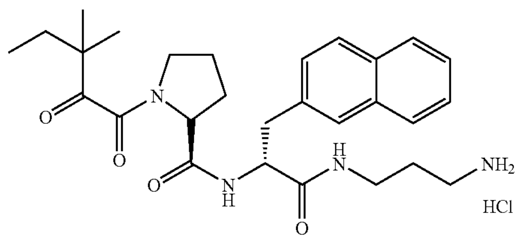 | II | 0.77(3H, t), 1.10(3H, s), 1.12(3H, s), 1.25–2.00(8H, m), 2.40–3.40(8H, m), 4.25–4.80(2H, m), 7.30–8.20 (10H, m), 7.89(1H, s), 8.52(1H, d) | 495 |
| 205 | 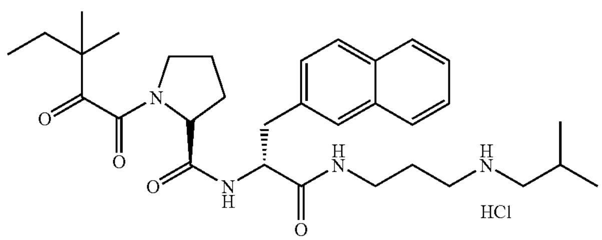 | V | 0.77(3H, t), 0.94(6H, d), 1.10(3H, s), 1.13(3H, s), 1.30–2.10(9H, m), 2.40–3.50(10H, m), 4.30–4.80(2H, m), 7.30–7.60(3H, m), 7.71(1H, s), 7.75–7.95 (3H, m), 8.10–8.90(3H, m) | 551 |
| 206 | 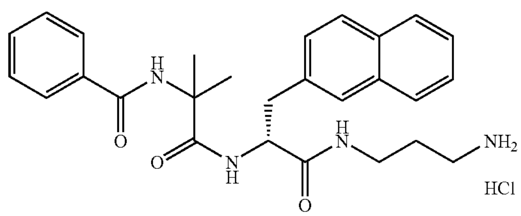 | II | 1.20(3H, s), 1.29(3H, s), 1.60–2.00(2H, m), 2.40–3.60(6H, m), 4.40–4.60(1H, m), 7.30–8.20(18H, m) | 461 |
| 207 | 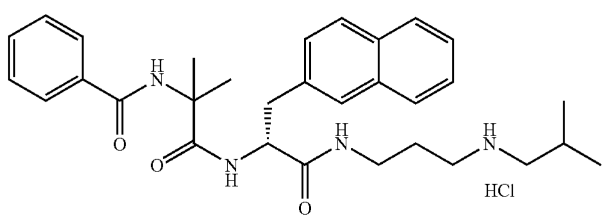 | V | 0.92(6H, d), 1.29(3H, s), 1.46(3H, s), 1.80–2.10 (3H, m), 2.30–4.00(8H, m), 4.40–4.60(1H, m), 7.30–8.10(14H, m), 7.66(1H, s), 8.55(1H, s), 8.60–8.85(2H, m) | 517 |
| 208 | 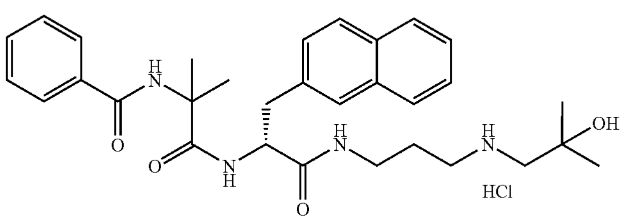 | II | 1.19(6H, s), 1.30–1.60(2H, m), 1.91(6H, s), 2.30–3.60 (8H, m), 4.40–4.60(1H, m), 5.00–5.30(1H, m), 7.20–8.10(12H, m), 8.40–8.60(2H, br), 8.56(1H, s), 11.70–12.30 (1H, br) | 533 |
| 209 | 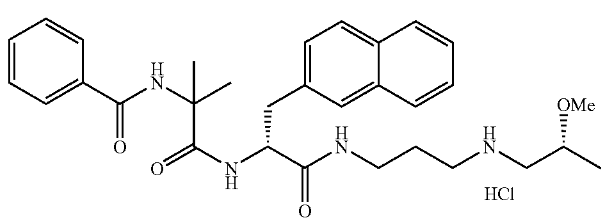 | II | 1.09(3Hd), 1.21(3H, s), 1.29(3H, s), 2.70–3.00(2H, m), 2.40–3.80(8H, m), 3.95–4.15(1H, m), 4.40–4.70(1H, m), 7.20–8.00(17H, m), | 533 |

-continued

| Ex. No. | Structure | Methods | ¹H-NMR(δ ppm): | FAB-MS (M+H)⁺ |
|---|---|---|---|---|
| 210 | 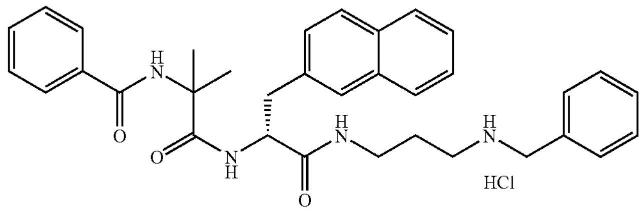 | V | 1.20(3H, s), 1.29(3H, s), 1.80–2.05(2H, m), 2.80–3.70(6H, m), 3.90–4.10(2H, m), 4.40–4.60(1H, m), 7.20–8.10(19H, m), 8.57(1H, s), 9.20–9.50(2H, br) | 551 |
| 211 | 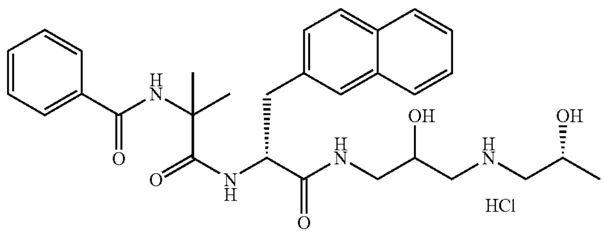 | I | 1.08(3H, d), 1.22(3H, s), 1.29(3H, s), 2.60–3.40(8H, m), 3.90–4.05(2H, m), 4.45–4.55(1H, m), 5.30(1H, bs), 5.60(1H, bs), 7.35–7.60(6H, m), 7.65(1H, s), 7.70–8.00(7H, m), 8.25–8.65(3H, m) | 535 |
| 212 | 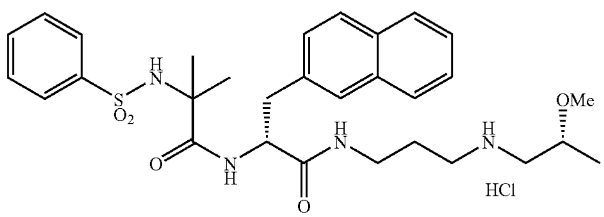 | II | 1.02(3H, s), 1.09(3H, d), 1.14(3H, s), 2.70–2.90(2H, m), 2.40–3.80(8H, m), 3.29(3H, s), 3.95–4.15(1H, m), 4.40–4.65(1H, m), 7.30–8.20(17H, m) | 569 |
| 213 | 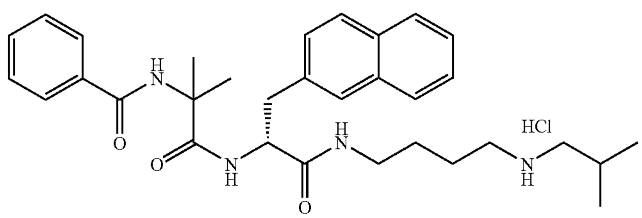 | II | 0.93(6H, d), 1.16(3H, s), 1.27(3H, s), 1.40–1.80(4H, m), 1.96(1H, dq), 2.40–3.60(8H, m), 4.40–4.65(1H, m), 7.30–8.05(14H, m), 8.50–8.85(2H, br), 8.54(1H, s) | 531 |
| 214 | 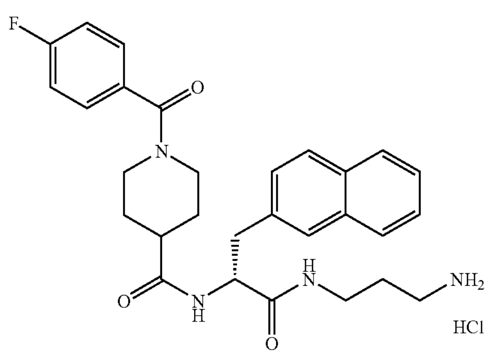 | II | 1.10–1.90(6H, m), 2.40–3.80(10H, m), 2.96(1H, dd), 4.00–4.40(1H, br), 4.55(1H, dt), 7.24(2H, t), 7.30–7.55(5H, m), 7.60–8.00(5H, m), 7.71(1H, s), 8.15–8.30(2H, m) | 505 |

| Ex. No. | Structure | Methods | ¹H-NMR(δ ppm): | FAB-MS (M+H)⁺ |
|---|---|---|---|---|
| 215 | 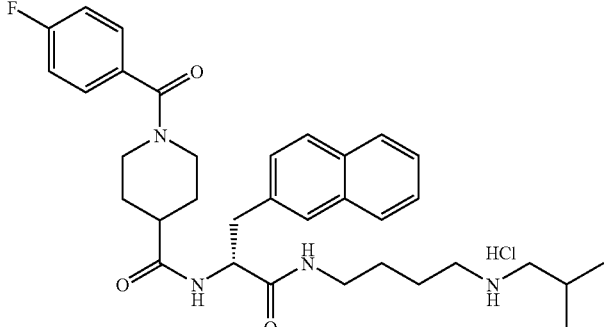 | II | 0.94(6H, d), 1.10–1.80(8H, m), 1.99(1H, dq), 2.40–3.30(13H, m), 4.45–4.75(1H, m), 7.20–7.55(4H, m), 7.25(2H, t), 7.71(1H, s), 7.70–8.95(3H, m) | 575 |
| 216 | 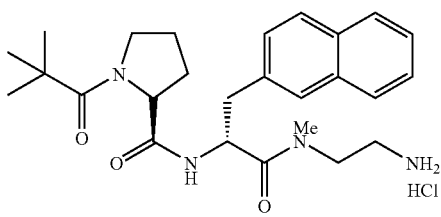 | II | 1.00–2.00(4H, m), 1.14(9H, m), 2.56(3H, s), 2.90–3.80(8H, m), 4.15–4.35(1H, m), 4.40–4.60(1H, m), 7.30–7.50(3H, m), 7.70(1H, s), 7.75–7.95 (3H, m), 8.10–8.30(1H, m), 8.52(1H, d), 8.60–9.00(2H, br) | 453 |
| 217 | 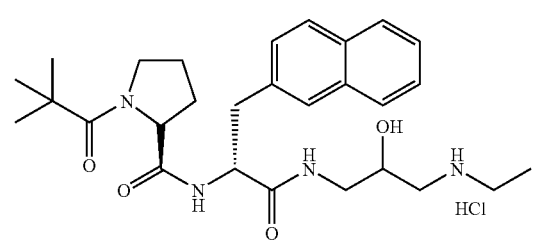 | II | 1.00–2.00(7H, m), 1.12(9H, s), 2.60–3.70(10H, m), 3.80–4.00(1H, m), 4.20–4.60(1H, m), 7.30–7.55(3H, m), 7.71(1H, s), 7.75–7.95(3H, m), 8.05–8.90(4H, m) | 497 |
| 218 | 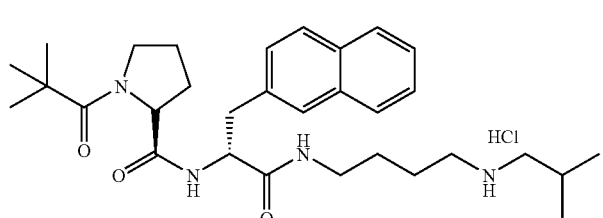 | II | 0.90–2.15(9H, m), 0.95(6H, d), 1.14(9H, s), 2.60–3.80 (10H, m), 4.20–4.35(1H, br), 4.40–4.60(1H, m), 7.30–7.55(3H, m), 7.71(1H, s), 7.75–8.10 (4H, m), 8.47(1H, d), 8.50–8.85(2H, br) | 523 |
| 219 | 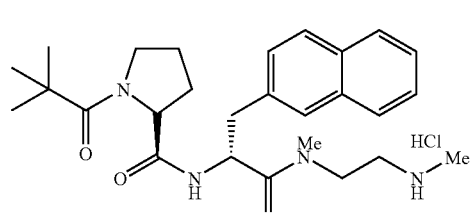 | II | 1.10(9H, s), 1.40–2.00(4H, m), 2.40–3.90(8H, m), 2.51(3H, s), 3.00(3H, s), 4.20–4.50(1H, br), 4.85–5.20(1H, m), 7.30–7.55(3H, m), 7.69(1H, s), 7.70–8.00 (3H, s), 8.10–8.40(1H, m), 8.70–9.05(2H, br) | 467 |
| 220 | 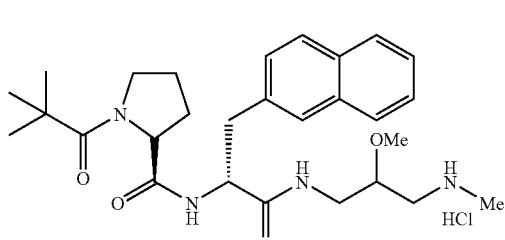 | II | 1.13(9H, s), 1.50–2.00(4H, m), 2.40–3.80(9H, m), 2.51(3H, s), 3.37(3H, s), 4.20–4.40(1H, m), 4.45–4.70(1H, m), 7.35–7.60(3H, m), 7.71(1H, s), 7.75–7.95(3H, m), 8.10–8.25(1H, m), 8.30–8.50(1H, m), 8.55–8.75(1H, br), 8.85–9.10(1H, br) | 497 |

| Ex. No. | Structure | Methods | $^1$H-NMR($\delta$ ppm): | FAB-MS $(M+H)^+$ |
|---|---|---|---|---|
| 221 | 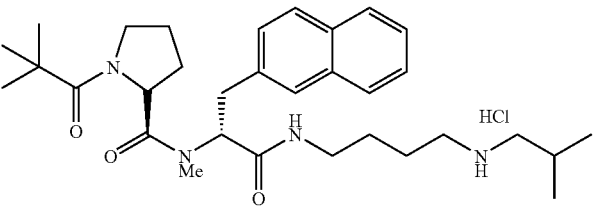 | II | 0.95(6H, d), 1.00–1.80(7H, m), 1.13(9H, s), 1.90–2.20 (2H, m), 2.70–3.80(10H, m), 2.98(3H, s), 4.50–4.65(1H, m), 5.45(1H, dd), 7.30–7.90 (6H, m), 7.68(1H, s), 7.80(1H, d), 8.60–8.90 (2H, br) | 537 |
| 222 | 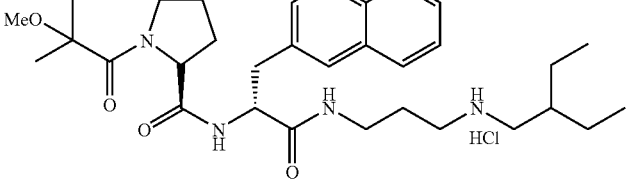 | V | 0.84(6H, t), 1.00–2.10(11H, m), 1.25(3H, s), 1.27(3H, s), 2.45–3.90(10H, m), 3.11(3H, s), 4.33(1H, t), 7.30–7.60(3H, m), 7.71(1H, s), 7.75–7.95 (3H, m), 8.17(1H, t), 8.55(1H, d), 8.60–8.90 (2H, br) | 553 |
| 223 | 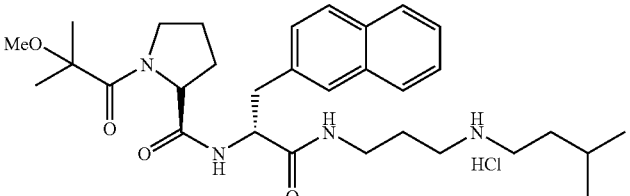 | V | 0.89(6H, d), 1.00–2.00(9H, m), 1.25(3H, s), 1.27(3H, s), 2.45–3.95(10H, m), 3.11(3H, s), 4.31(1H, t), 7.30–7.60(3H, m), 7.70(1H, s), 7.75–8.00 (3H, m), 8.05–8.25(1H, m), 8.49(1H, m), 8.70–8.90(2H, br) | 539 |
| 224 | 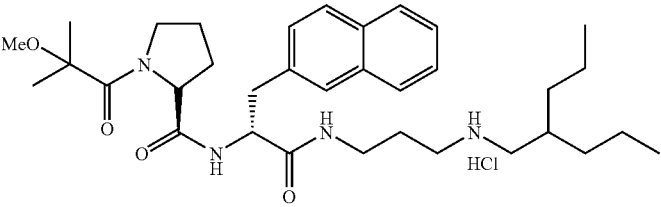 | V | 0.88(6H, s), 1.00–2.00(13H, m), 1.25(3H, s), 1.27(3H, s), 3.70–3.90(1H, m), 4.20–4.60(1H, m), 7.30–7.55(3H, m), 7.70(1H, s), 7.75–7.95 (3H, m), 8.05–8.20 (1H, m), 8.40–8.70(3H, m) | 581 |
| 225 | 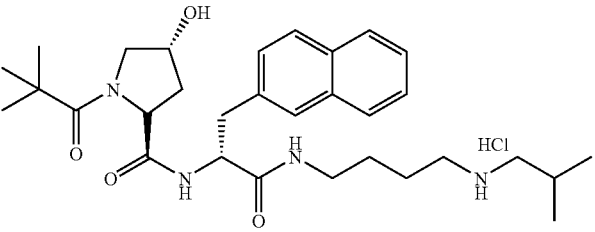 | II | 0.95(6H, d), 1.14(9H, s), 1.30–1.80(6H, m), 1.98(1H, dq), 2.60–2.80(11H, m), 4.15–4.25(1H, m), 4.30–4.50(1H, m), 7.30–7.55(3H, m), 7.71(1H, s), 7.75–8.10(4H, m), 8.50–8.80(3H, m) | 539 |
| 226 | 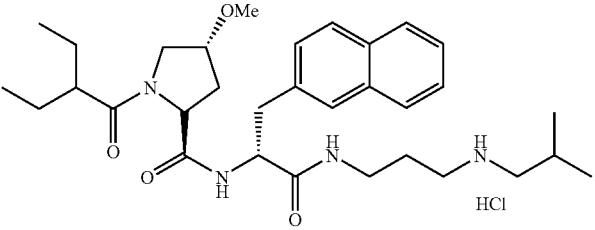 | II | 0.78(3H, t), 0.80(3H, t), 0.95(6H, d), 1.30–2.20(9H, m), 2.40–3.90(11H, m), 4.33(1H, t), 4.35–4.60 (1H, m), 7.30–7.55(3H, m), 7.72(1H, s), 7.75–7.95 (3H, m), 8.10–8.30(1H, m), 8.60–8.90(3H, m) | 553 |

| Ex. No. | Structure | Methods | ¹H-NMR(δ ppm): | FAB-MS (M+H)⁺ |
|---|---|---|---|---|
| 227 | 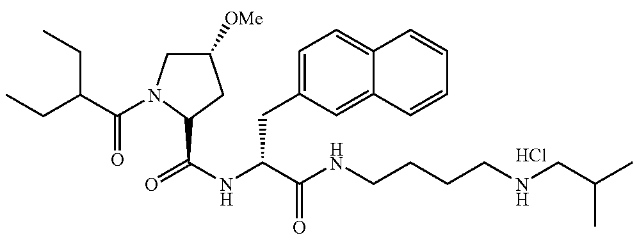 | II | 0.70–1.00(6H, m), 0.95(6H, d), 1.30–2.15(11H, m), 2.30–4.00(12H, m), 4.30–4.60(1H, m), 4.33(1H, t), 7.30–7.60(3H, m), 7.72(1H, s), 7.70–8.20 (4H, m), 8.60–8.90(3H, m) | 567 |
| 228 | 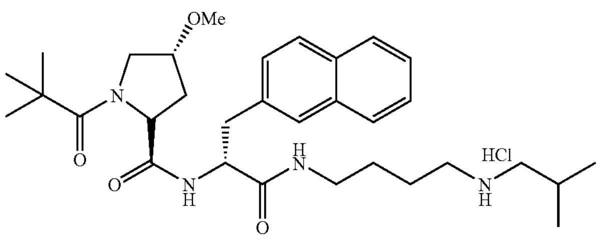 | II | 0.95(6H, d), 1.14(9H, s), 1.20–2.20(7H, m), 2.60–4.00(11H, m), 3.15(3H, m), 4.20–4.60 (2H, m), 7.30–7.60(3H, m), 7.71(1H, s), 7.75–8.10 (4H, m), 8.50–8.90(3H, m) | 553 |
| 229 | 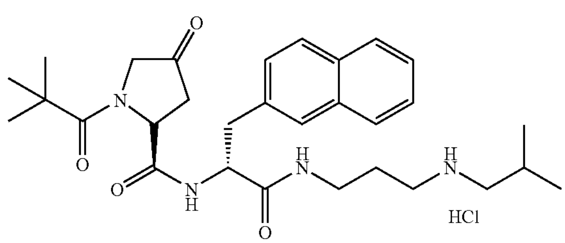 | II | 0.94(6H, d), 1.14(9H, s), 1.70–2.10(3H, m), 2.50–3.50(10H, m), 3.96(1H, d), 4.18(1H, d), 4.45–4.65(1H, m), 4.87(1H, d), 7.38(1H, d), 7.40–7.55(2H, m), 7.69(1H, s), 7.75–7.95 (2H, m), 7.82(1H, d), 8.05–8.20(1H, m), 8.35–8.60(2H, br), 8.63(1H, d) | 523 |
| 230 | 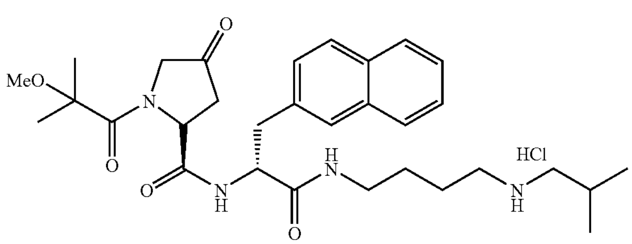 | II | 0.95(6H, d), 1.00–2.20(5H, m), 1.24(3H, s), 1.29(3H, s), 2.40–2.50(10H, m), 3.10(3H, s), 3.93(1H, d), 4.10–4.40(1H, m), 4.45–4.70(1H, m), 4.80–5.00(1H, m), 7.30–7.55(3H, m), 7.68(1H, s), 7.70–8.10(4H, m), 8.40–9.00(3H, m) | 553 |
| 231 | 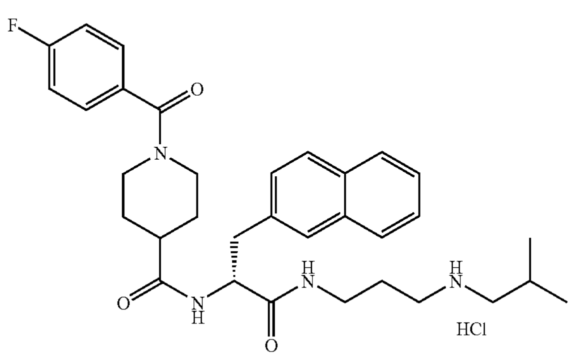 | II | 0.93(6H, d), 1.10–1.80(4H, m), 1.85–2.15(1H, m), 2.40–3.60(13H, m), 3.80–4.05(1H, m), 4.50–4.70(1H, m), 5.50–5.80(1H, br), 7.10–7.60(7H, m), 7.73(1H, s), 8.10–8.35 (2H, m), 8.40–8.70(2H.m) | 577 |

-continued

| Ex. No. | Structure | Methods | ¹H-NMR(δ ppm): | FAB-MS (M+H)⁺ |
|---|---|---|---|---|
| 232 | 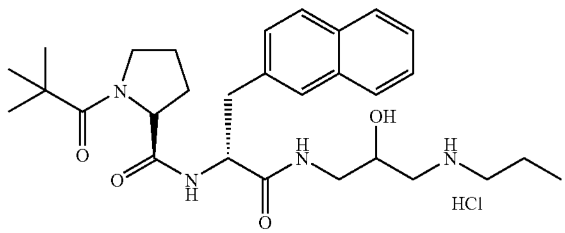 | IV | 0.89(3H, t), 1.00–2.00(6H, m), 1.13(9H, s), 2.65–3.70 (10H, m), 3.80–4.00(1H, m), 4.20–4.40(1H, m), 4.45–4.65(1H, m), 5.60–5.75(1H, m), 7.30–7.50(3H, m), 7.71(1H, s), 7.75–7.90(3H, m), 8.05–8.45(2H, m), 8.50–8.90(2H, br) | 511 |
| 233 | 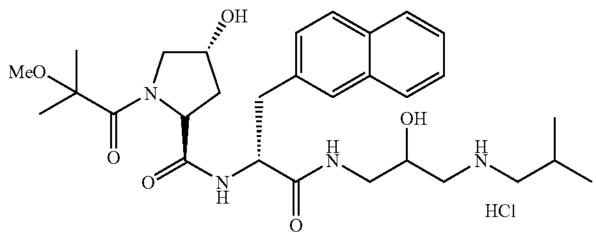 | II | 0.94(6H, d), 1.00–1.50(1H, m), 1.25(3H, s), 1.27(3H, s), 1.70–2.20(2H, m), 3.10(3H, s), 3.80–4.10 (1H.m), 3.86(1H, d), 4.16(1H, s), 4.42(1H, t), 4.45–4.65(1H, m), 7.30–7.55(3H, m), 7.71(1H, s), 7.75–7.95 (3H, m), 8.10–8.25(1H, m), 8.40–8.70(3H, m), | 557 |
| 234 | 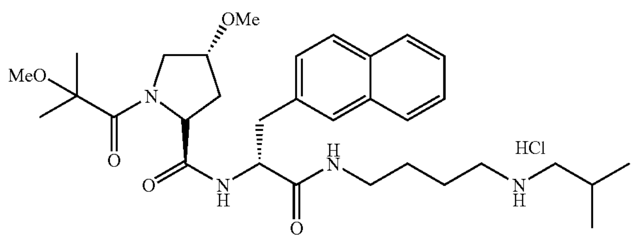 | II | 0.95(6H, d), 1.10–2.20(7H, m), 1.26(6H, m), 2.60–3.60 (9H, m), 3.03(3H, s), 3.07(3H, s), 3.65–3.80(1H, br), 3.98(1H, d), 4.64(1H, t), 5.43(1H, dd), 7.30–7.60(3H, m), 7.37(1H, d) | 583 |
| 235 | 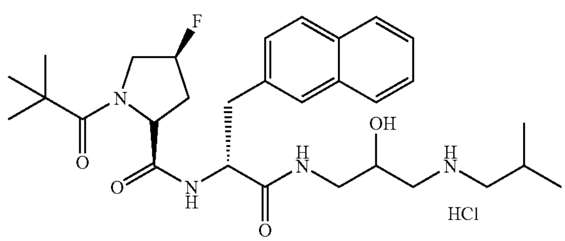 | II | 0.93(6H, d), 1.13(9H, s), 1.70–2.40(3H, m), 2.60–4.10(11H, m), 4.40–4.70(2H, m), 5.00–5.15(1H, br), 5.25–5.40(1H, br), 7.30–7.55(3H, m), 7.70(1H, s), 7.75–7.90 (3H, m), 8.02(1H, d), 8.15–8.30(1H, m), 8.45–8.70(2H, br) | 543 |
| 236 | 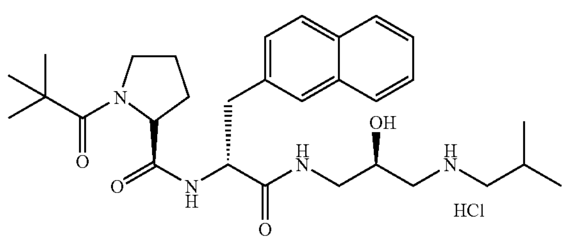 | II | 0.93(6H, d), 1.12(9H, s), 1.33(1H, m), 1.67(2H, m), 1.78(1H, m), 1.99(1H, m), 2.72(3H, m), 2.98(2H, m), 3.17(1H, m), 3.23–3.60(4H, m), 3.94(1H, m), 4.28(1H, m), 4.55(1H, m), 5.68(1H, d), 7.45(3H, m), 7.70(1H, s), 7.82(3H, m), 8.19(1H, t), 8.32(1H, d), 8.47(2H, br) | 525 |
| 237 | 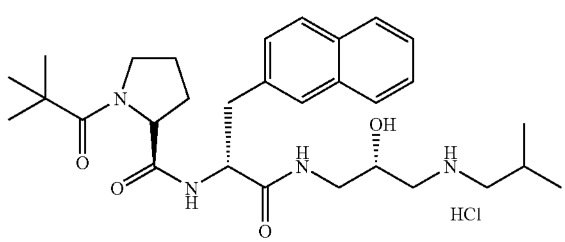 | II | 0.94(6H, d), 1.13(9H, s), 1.33(1H, m), 1.67(1H, m), 1.78(1H, m), 1.99(1H, m), 2.72(3H, m), 2.98(2H, m), 3.17(1H, m), 3.23–3.60(4H, m), 3.94(1H, m), 4.28(1H, m), 4.55(1H, m), 5.69(1H, d), 7.45(3H, m), 7.70(1H, s), 7.82(3H, m), 8.20(1H, t), 8.37(1H, d), 8.55(2H, br) | 525 |

| Ex. No. | Structure | Methods | $^1$H-NMR($\delta$ ppm): | FAB-MS $(M+H)^+$ |
|---|---|---|---|---|
| 238 | 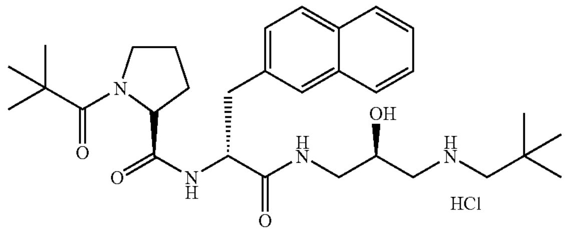 | II | 1.00(9H, s), 1.12(9H, s), 1.33(1H, m), 1.68(2H, m), 1.78(1H, m), 2.70–2.90(3H, m), 2.98(1H, m), 3.21–3.40 (2H, m), 3.40–3.70(2H, m), 4.00(1H, m), 4.28(1H, m), 4.55(1H, m), 5.73(1H, d), 7.45(3H, m), 7.71(1H, s), 7.82(3H, m), 8.20(1H, t), 8.20–8.40(1H, br), 8.35(1H, d), 8.35–8.50(1H, br) | 539 |
| 239 | 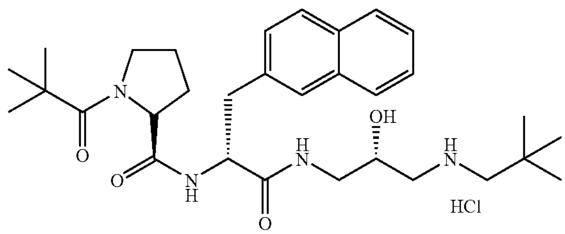 | II | 1.00(9H, s), 1.13(9H, s), 1.33(1H, m), 1.68(2H, m), 1.78(1H, m), 2.70–2.90(2H, m), 2.98–3.20(2H, m), 3.25–3.40(2H, m), 3.45–3.70(2H, m), 4.00(1H, m), 4.28(1H, m), 4.55(1H, m), 5.72(1H, d), 7.45(3H, m), 7.71(1H, s), 7.82(3H, m), 8.20(1H, t), 8.39(1H, d), 8.20–8.50 (2H, br) | 539 |

What is claimed is:

1. A compound having a formula:

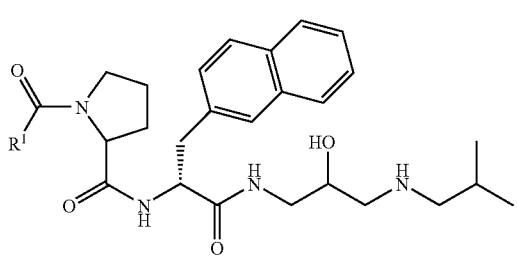

(1a)

wherein
R$^1$ is substituted or unsubstituted alkyl, substituted or unsubstituted cycloalkyl, substituted or unsubstituted alkoxy, substituted or unsubstituted aryl, or substituted or unsubstituted amino, and
pharmaceutically acceptable salts thereof.

2. A compound and pharmaceutically acceptable salts according to claim 1:
wherein R$^1$ is C$_{1-11}$ alkyl which may be substituted by substituted or unsubstituted cycloalkyl, substituted or unsubstituted alkoxy, substituted or unsubstituted aryl, and/or hydroxy; C$_{3-6}$ cycloalkyl which may be substituted by substituted or unsubstituted alkyl, substituted or unsubstituted alkoxy, substituted or unsubstituted aryl, and/or hydroxy; C$_{1-11}$ alkoxy which may be substituted by substituted or unsubstituted cycloalkyl, substituted or unsubstituted aryl, and/or hydroxy; aryl which may be substituted by substituted or unsubstituted alkyl, substituted or unsubstituted alkoxy, and/or hydroxy; or, amino which may be substituted by substituted or unsubstituted alkyl, and/or substituted or unsubstituted aryl.

3. A compound and pharmaceutically acceptable salts according to claim 2: wherein R$^1$ is C$_{1-11}$ alkyl which may be substituted by cycloalkyl, alkoxy, arylalkoxy, aryl and/or halogenated aryl; C$_{3-6}$ cycloalkyl which may be substituted by alkyl; C$_{1-5}$ alkoxy which may be substituted by aryl; aryl which may be substituted by alkyl, alkoxy and/or halogen; or, di(C$_{1-6}$ alkyl)amino.

4. A compound and pharmaceutically acceptable salts according to claim 3: wherein R$^1$ is selected from the group consisting of

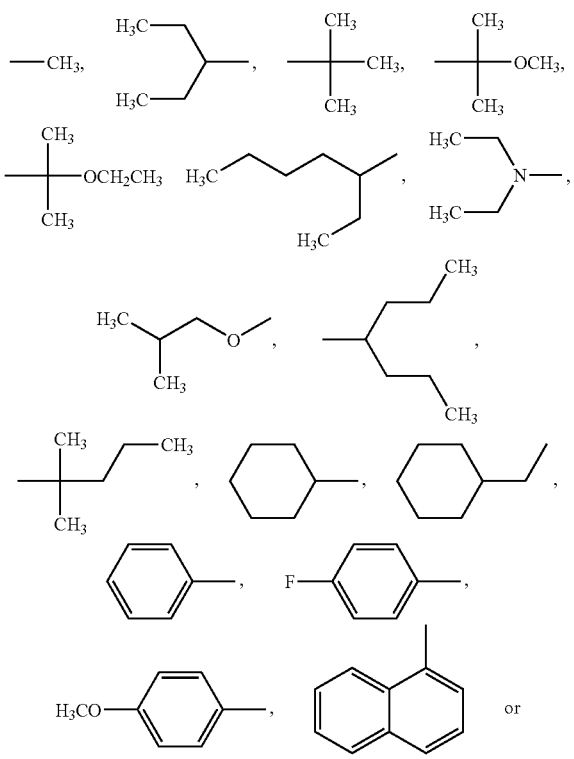

-continued

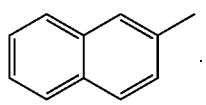

5. A composition which comprises an inert carrier and an effective amount of a compound according to claim 1.

6. A method for increasing levels of endogenous growth hormones in a human or an animal which comprises administering to such human or animal an effective amount of a compound according to claim 1.

7. A method to increase the rate and growth of animals, the method comprising administering to a subject in need thereof an effective amount of a compound according to claim 1.

8. A method to increase the milk production of animals, the method comprising administering to a subject in need thereof an effective amount of a compound according to claim 1.

9. A method to increase the wool production of animals, the method comprising administering to a subject in need thereof an effective amount of a compound according to claim 1.

* * * * *